US008785489B2

(12) United States Patent  
Abeywardane et al.

(10) Patent No.: US 8,785,489 B2  
(45) Date of Patent: Jul. 22, 2014

(54) HETEROARYL SUBSTITUTED INDOLE COMPOUNDS USEFUL AS MMP-13 INHIBITORS

(75) Inventors: Asitha Abeywardane, Danbury, CT (US); Bennett Farmer, Ridgefield, CT (US); Neil Alexander Farrow, Ridgefield, CT (US); Donghong Amy Gao, Hopewell Junction, NY (US); Alexander Heim-Riether, Biberach an der Riss (DE); Lana Louise Smith Keenan, Poughquag, NY (US); Ingo Andreas Mugge, New Haven, CT (US); Steven John Taylor, Southbury, CT (US); Zhaoming Xiong, Brookfield, CT (US); Yang Yu, Clark, NJ (US); Qiang Zhang, Woodbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 161 days.

(21) Appl. No.: 13/123,048

(22) PCT Filed: Oct. 13, 2009

(86) PCT No.: PCT/US2009/060436  
§ 371 (c)(1),  
(2), (4) Date: Jun. 7, 2011

(87) PCT Pub. No.: WO2010/045188  
PCT Pub. Date: Apr. 22, 2010

(65) Prior Publication Data  
US 2011/0275631 A1 Nov. 10, 2011

Related U.S. Application Data

(60) Provisional application No. 61/106,207, filed on Oct. 17, 2008.

(51) Int. Cl.  
*A61K 31/5377* (2006.01)  
*A61K 31/506* (2006.01)  
*A61K 31/497* (2006.01)  
*A61K 31/454* (2006.01)  
*A61K 31/444* (2006.01)  
*A61K 31/4439* (2006.01)  
*A61K 31/427* (2006.01)  
*A61K 31/422* (2006.01)  
*A61K 31/4178* (2006.01)  
*A61K 31/4155* (2006.01)  
*A61K 31/404* (2006.01)  
*C07D 413/14* (2006.01)  
*C07D 413/04* (2006.01)  
*C07D 409/14* (2006.01)  
*C07D 409/04* (2006.01)  
*C07D 405/14* (2006.01)  
*C07D 405/04* (2006.01)  
*C07D 403/14* (2006.01)  
*C07D 403/04* (2006.01)  
*C07D 401/14* (2006.01)  
*C07D 401/04* (2006.01)  
*C07D 487/04* (2006.01)  
*C07D 405/12* (2006.01)  
*C07D 417/14* (2006.01)  
*C07D 471/04* (2006.01)  
*C07D 209/42* (2006.01)

(52) U.S. Cl.  
CPC ........... *A61K 31/427* (2013.01); *A61K 31/4155* (2013.01); *C07D 401/04* (2013.01); *C07D 409/14* (2013.01); *A61K 31/454* (2013.01); *A61K 31/422* (2013.01); *C07D 405/14* (2013.01); *C07D 405/04* (2013.01); *C07D 403/14* (2013.01); *C07D 487/04* (2013.01); *A61K 31/4439* (2013.01); *C07D 405/12* (2013.01); *A61K 31/497* (2013.01); *C07D 409/04* (2013.01); *C07D 417/14* (2013.01); *C07D 413/14* (2013.01); *C07D 401/14* (2013.01); *A61K 31/404* (2013.01); *C07D 471/04* (2013.01); *C07D 209/42* (2013.01); *C07D 403/04* (2013.01); *A61K 31/444* (2013.01); *C07D 413/04* (2013.01); *A61K 31/506* (2013.01); *A61K 31/4178* (2013.01); *A61K 31/5377* (2013.01)  
USPC ........... 514/415; 514/256; 514/333; 514/339; 514/364; 514/365; 514/378; 514/397; 514/406; 514/414; 514/419; 514/235.2; 544/333; 544/138; 544/238; 546/256; 546/269.1; 546/272.7; 546/275.1; 546/275.4; 546/277.4; 546/278.1; 548/131; 548/181; 548/247; 548/312.1; 548/364.7; 548/466; 548/467; 548/492

(58) Field of Classification Search  
CPC .. C07D 413/14; C07D 413/04; C07D 409/14; C07D 409/04; C07D 405/14; C07D 405/04; C07D 403/14; C07D 403/04; C07D 401/14; C07D 401/04; A61K 31/5377; A61K 31/506; A61K 31/497; A61K 31/454; A61K 31/444; A61K 31/4439; A61K 31/427; A61K 31/422; A61K 31/4178; A61K 31/4155; A61K 31/404  
USPC ......... 514/256, 333, 339, 364, 365, 378, 397, 514/406, 414, 419, 415, 235.2; 544/333, 544/138, 238; 546/256, 269.1, 272.7, 546/275.1, 275.4, 277.4, 278.1; 548/131, 548/181, 247, 312.1, 364.7, 466, 467, 492  
See application file for complete search history.

(56) References Cited

U.S. PATENT DOCUMENTS

| 2004/0063686 A1 | 4/2004 | Johnson et al. | |
|---|---|---|---|
| 2005/0203127 A1 | 9/2005 | Cezanne et al. | |
| 2006/0235037 A1* | 10/2006 | Purandare et al. | 514/278 |
| 2007/0213333 A1 | 9/2007 | Shoda et al. | |
| 2008/0039442 A1 | 2/2008 | Blom et al. | |
| 2011/0275625 A1 | 11/2011 | Farrow et al. | |
| 2006/0235037 A1* | 10/2006 | Purandare et al. | 514/278 |
| 2007/0213333 A1 | 9/2007 | Shoda et al. | |
| 2008/0039442 A1 | 2/2008 | Blom et al. | |
| 2011/0275625 A1 | 11/2011 | Farrow et al. | |

US 8,785,489 B2

Page 2

FOREIGN PATENT DOCUMENTS

| EP | 1820795 A1 | 8/2007 |
| WO | 0033836 A1 | 6/2000 |
| WO | 0210146 A1 | 2/2002 |
| WO | 0216348 A1 | 2/2002 |
| WO | WO 03093297 A2 * | 11/2003 |
| WO | 2006008133 A2 | 1/2006 |
| WO | 2006086705 A1 | 8/2006 |
| WO | 2006113458 A1 | 10/2006 |
| WO | 2007024600 A2 | 3/2007 |
| WO | WO 2008152099 A2 * | 12/2008 |
| WO | 2010045188 A1 | 4/2010 |
| WO | 2010045190 A1 | 4/2010 |
| WO | 2010056585 A2 | 5/2010 |

OTHER PUBLICATIONS

Djidel et al. Heterocycles 2005, 65, 1679-1683.*
Chemical Abstract: Accession No. 1977:163054, Gverdtsiteli, Solvatrochromium and ultraviolet spectra of several carboxylic acids of indole homlogs, vol. 83, No. 3, 1976, p. 609-6012.*
Scriven et al. Journal of the Chemical Society, Perkin Transactions 1: Organic and Bio-Organic Chemistry (1972-1999) 1979, 1, 53-59.*
International Search Report and Written Opinion for PCT/EP2009/060436 mailed Feb. 3, 2010.
Fukuda, Y. et al., "The Novel Cyclopropapyrroloindole(CPI) Bisalkylators Bearning Methoxycarbonyl and Trifluoromethyl Groups." Bioorganice and Medicinal Chemistry Letters 8 , 1998, p. 1387-1390.

* cited by examiner

*Primary Examiner* — Joseph Kosack
*Assistant Examiner* — Matthew Coughlin
(74) *Attorney, Agent, or Firm* — Michael P. Morris; Anthony P. Bottino

(57) ABSTRACT

Disclosed are compounds and compositions of the formula I as described herein which are inhibitors of MMP-13. Also disclosed are methods of using and making compounds of the formula I.

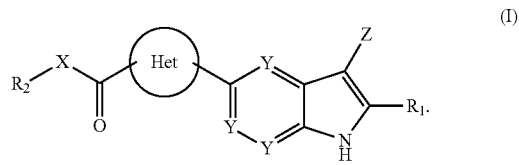

11 Claims, No Drawings

HETEROARYL SUBSTITUTED INDOLE COMPOUNDS USEFUL AS MMP-13 INHIBITORS

APPLICATION DATA

This application claims benefit to U.S. provisional application Ser. No. 61/106,207 filed Oct. 17, 2008.

BACKGROUND OF THE INVENTION

1. Technical Field

The invention relates to MMP-13 metalloprotease inhibiting compounds.

2. Background Information

Matrix metalloproteinases (MMPs) are zinc-dependent endopeptidases. MMPs function to degrade extracellular matrix proteins and are involved in the cleavage of cell surface receptors, growth factors, cell-adhesion molecules, cytokines and chemokines, as well as other MMPs and unrelated proteases. MMPs are also thought to play a major role on cellular processes such as proliferation, migration (adhesion/dispersion), differentiation, angiogenesis, apoptosis and host defense. (Hu J. et al. Nat. Rev. Drug Discov. 2007, 6:480-498; Ramnath N. and Creaven P. J. Curr. Onco. Rep. 2004, 6:96-102). MMPs are therefore targets for therapeutic diseases including rheumatoid arthritis, osteoarthritis, osteoporosis, peridontitis, atherosclerosis, congestive heart failure, multiple sclerosis and tumor metastasis.

The mammalian MMP family includes more than 20 members that share common structural attributes: a propeptide domain, a catalytic domain and a C-terminal hemopexin-like domain (except for MMP-7 and MMP-26). The function of MMPs in health and disease is regulated in multiple ways. MMPs are secreted as inactive proproteins which are activated when the propeptide domain is cleaved by extracellular proteinases or destabilized by protein-protein interactions. The activity of MMPs is also regulated by tissue inhibitors of metalloproteinases (TIMPs) which bind to the catalytic site of MMPs. The production of MMPs is also regulated at the level of transcription by specific signals that are temporally limited and spatially confined. (Parks W. C. et al Nat. Rev. Immunol. 2004 4:617-629).

The collagenase subset of the matrix metalloproteinase family, comprising MMP-1 (collagenase 1), MMP-8 (collagenase 2), MMP-13 (collagenase 3) and more recently MMP-14, catalyzes the initial cleavage of collagen types I, II, III, V and X (Parks W. C. et al Nat. Rev. Immunol. 2004, 4:617-629). MMP-13 cleaves type II collagen more efficiently than types I and III and is capable of cleaving multiple extracellular matrix proteins in addition to fibrillar collagens (Leeman M. F. et al Crit. Rev. Biochem. Mol. Biol. 2003, 37: 149-166). MMP-13 is the most effective catalyst of collagen type II degradation, the committed step in articular cartilage degradation and progressive joint damage associated with RA and osteoarthritis (OA). In the case of collagen type II (90-95% of articular cartilage), the triple helix is cleaved by MMP-13 at position G775/L776 at least an order of magnitude faster than by MMP-1 and MMP-8 (Billinghurst, R. C. et al. J. Clin. Invest. 1997, 99, 1534-1545). Cleavage of collagen type II triple helix at position G775/L776 by MMP-13 triggers the initial unfolding of the molecule, rendering it susceptible to catalytic degradation by additional members of the MMP family. The superior catalytic efficiency of MMP-13 for collagen type II degradation, coupled with increased expression of MMP-13 in synovial fibroblasts and chondrocytes associated with rheumatoid arthritis (RA) and osteoarthritis (OA) pathology, is consistent with MMP-13 being responsible for catalyzing the committed step in cartilage degradation associated with RA and OA (Mitchell, P. G. et al. J. Clin. Invest. 1996, 97, 761-768; Moore, B. A. et al, Biochim. Biophys. Acta 2000, 1502, 307-318).

Furthermore, transient adenoviral expression of MMP-13 in mouse knee chondrocytes and synoviocytes induces a transient arthritic condition, including recruitment of inflammatory cells, and up-regulation of inflammatory cytokine mRNA (Oronen, K. et al. Ann, Rheum. Dis, 2004, 63, 656-664). Transgenic mice with a constitutively active form of human MMP-13 in cartilage exhibit augmented cleavage of type II collagen leading to an osteoarthritic-like phenotype with marked cartilage degradation and synovial hyperplasia (Neuhold, L. A. et al J. Clin. Invest. 2001, 107, 35-44). These in vivo validation studies further support the role of MMP-13 in RA and OA pathogenesis.

BRIEF SUMMARY OF THE INVENTION

It has been found that compounds of the present invention are inhibitors of MMP-13.

It is therefore an object of the invention to provide compounds and compositions of the formula I as described herein below which are inhibitors of MMP-13.

It is a further object of the invention to provide methods of using and making compounds of the formula I which are inhibitors of MMP-13.

DETAILED DESCRIPTION OF THE INVENTION

In the broadest generic embodiment, there is provided a compound of the formula (I):

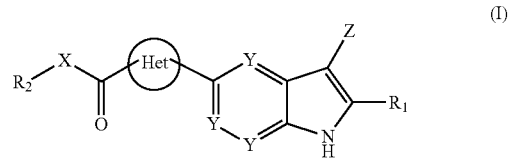

(I)

Het is a ring chosen from phenyl, heteroaryl and heterocycle each optionally substituted by one to three $C_{1-5}$ alkyl, $C_{1-5}$ alkoxy, $C_{1-5}$ acyl, $C_{1-5}$ acylamino, amino, cyano, hydroxyl or halogen;

X is —O— or —N($R_3$)—;

Y is N or C

Z is H or F $R_1$ is chosen from $C_{1-5}$ alkyl, $C_{1-5}$ alkoxy$C_{1-5}$ alkyl, $C_{1-5}$ alkoxy, $C_{1-5}$ alkoxycarbonyl-$(CH_2)_n$—, HOC(=O)—$(CH_2)_n$—, hydroxy$C_{1-5}$ alkyl, —C(O)N$R_4R_5$ and $Ar_1$;

$R_2$ is chosen from hydrogen, $Ar_2$—$(CH_2)_n$—, heterocycle, or $C_{1-5}$ alkyl;

$R_3$ is chosen from hydrogen and $C_{1-5}$ alkyl;

each $R_4$ and $R_5$ is independently chosen from hydrogen, $C_{1-5}$ acyl, $C_{1-5}$ alkyl, $C_{1-5}$ alkoxy, hydroxyl, carbocycle-$(CH_2)_n$—, heteroaryl-$(CH_2)_n$— and heterocycle-$(CH_2)_n$—;

$Ar_1$ is chosen from carbocycle, heteroaryl and heterocycle wherein $Ar_1$ is optionally substituted by one to three $C_{1-5}$ alkyl, $C_{1-5}$ alkoxy, $C_{1-5}$ acyl, $C_{1-5}$ acylamino, amino, cyano, hydroxyl or halogen;

$Ar_2$ is chosen from carbocycle, heteroaryl and heterocycle wherein $Ar_2$ is optionally substituted by one to three heteroaryl, $C_{1-5}$ alkyl, $C_{1-5}$ alkoxy-$(CH_2)_n$—, $C_{1-5}$ alkoxycarbonyl-(CH$_2$)$_n$—, carboxy-(CH$_2$)$_n$—, C$_{1-5}$ acyl, C$_{1-5}$ acylamino, amino, cyano, hydroxyl, sulfonyl, sulfoxide, thio, oxo or halogen;

each n is independently 0-2;

or a pharmaceutically acceptable salt thereof.

In another embodiment, there is provided a compound of the formula (II) according the embodiment described immediately above, and wherein

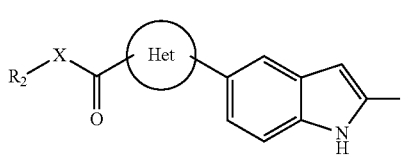

(II)

X is —N(R$_3$)—;

Het is a ring chosen from oxazolyl, isoxazolyl, oxadiazolyl, thiazolyl, isothiazolyl, pyrazolyl, pyrrolyl, imidazolyl, pyridinyl, pyrimidinyl, pyridazinyl and pyrazinyl each optionally substituted by one to three C$_{1-5}$ alkyl, C$_{1-5}$ alkoxy, C$_{1-5}$ acyl, C$_{1-5}$ acylamino, amino, cyano, hydroxyl or halogen;

R$_1$ is chosen from C$_{1-5}$ alkoxy C$_{1-5}$ alkyl, C$_{1-5}$ alkoxycarbonyl-(CH$_2$)$_n$— and Ar$_1$;

R$_2$ is chosen from Ar$_2$—(CH$_2$)$_n$—, heterocycle, or C$_{1-5}$ alkyl;

Ar$_1$ is chosen from phenyl, oxazolyl, 4,5-dihydro-oxazolyl, isoxazolyl, oxadiazolyl, thiazolyl, pyrazolyl, pyrrolyl, imidazolyl, pyridinyl, pyrimidinyl, pyridazinyl and pyrazinyl wherein Ar$_1$ is optionally substituted by one to three C$_{1-5}$ alkyl, C$_{1-5}$ alkoxy, C$_{1-5}$ acyl, C$_{1-5}$ acylamino, amino, cyano, hydroxyl or halogen;

Ar$_2$ is chosen from phenyl, oxazolyl, isoxazolyl, oxadiazolyl, furanyl, thiophenyl, triazolyl, thiadiazolyl, isothiazolyl, thiazolyl, pyrazolyl, pyrrolyl, imidazolyl, pyridinyl, pyrimidinyl, pyridazinyl and pyrazinyl wherein Ar$_2$ is optionally substituted by one to three C$_{1-5}$ alkyl, C$_{1-5}$ alkoxy-(CH$_2$)$_n$—, C$_{1-5}$ alkoxycarbonyl-(CH$_2$)$_n$—, carboxy-(CH$_2$)$_n$—, C$_{1-5}$ acyl, C$_{1-5}$ acylamino, amino, cyano, hydroxyl, oxo or halogen;

or a pharmaceutically acceptable salt thereof.

In another embodiment, there is provided a compound of the formula (I) or formula (II) and wherein Het is a ring chosen from phenyl, heteroaryl and heterocycle each optionally substituted by one to three C$_{1-5}$ alkyl, C$_{1-5}$ alkoxy, C$_{1-5}$ acyl, C$_{1-5}$ acylamino, amino, cyano, hydroxyl or halogen;

X is —O— or —N(R$_3$)—;

R$_1$ is chosen from C$_{1-5}$ alkyl, C$_{1-5}$ alkoxyC$_{1-5}$ alkyl, C$_{1-5}$ alkoxy, C$_{1-5}$ alkoxycarbonyl-(CH$_2$)$_n$—, HOC(=O)—(CH$_2$)$_n$—, hydroxyC$_{1-5}$ alkyl, —C(O)NR$_4$R$_5$ and Ar$_1$;

R$_2$ is chosen from hydrogen, Ar$_2$—(CH$_2$)$_n$— heterocycle, or C$_{1-5}$ alkyl;

R$_3$ is chosen from hydrogen and C$_{1-5}$ alkyl;

each R$_4$ and R$_5$ is independently chosen from hydrogen, C$_{1-5}$ acyl, C$_{1-5}$ alkyl, C$_{1-5}$ alkoxy, hydroxyl, carbocycle-(CH$_2$)$_n$—, heteroaryl-(CH$_2$)$_n$— and heterocycle-(CH$_2$)$_n$—;

Ar$_1$ is chosen from carbocycle, heteroaryl and heterocycle wherein Ar$_1$ is optionally substituted by one to three C$_{1-5}$ alkyl, C$_{1-5}$ alkoxy, C$_{1-5}$ acyl, C$_{1-5}$ acylamino, amino, cyano, hydroxyl or halogen;

Ar$_2$ is chosen from carbocycle, heteroaryl and heterocycle wherein Ar$_2$ is optionally substituted by one to three heteroaryl, C$_{1-5}$ alkyl, C$_{1-5}$ alkoxy-(CH$_2$)$_n$—, C$_{1-5}$ alkoxycarbonyl-(CH$_2$)$_n$—, carboxy-(CH$_2$)$_n$—, C$_{1-5}$ acyl, C$_{1-5}$ acylamino, amino, cyano, hydroxyl, sulfonyl, sulfoxide, thio, oxo or halogen;

each n is independently 0-2.

In another embodiment, there is provided a compound of the formula (I) or formula (II) according the embodiment described immediately above, and wherein X is —N(R$_3$)—;

Het is a ring chosen from oxazolyl, isoxazolyl, oxadiazolyl, thiazolyl, isothiazolyl, pyrazolyl, pyrrolyl, imidazolyl, pyridinyl, pyrimidinyl, pyridazinyl and pyrazinyl each optionally substituted by one to three C$_{1-5}$ alkyl, C$_{1-5}$ alkoxy, C$_{1-5}$ acyl, C$_{1-5}$ acylamino, amino, cyano, hydroxyl or halogen;

R$_1$ is chosen from C$_{1-5}$ alkoxyC$_{1-5}$ alkyl, C$_{1-5}$ alkoxycarbonyl-(CH$_2$)$_n$— and Ar$_1$;

R$_2$ is chosen from Ar$_2$—(CH$_2$)$_n$—;

Ar$_1$ is chosen from phenyl, oxazolyl, 4,5-dihydro-oxazolyl, isoxazolyl, oxadiazolyl, thiazolyl, pyrazolyl, pyrrolyl, imidazolyl, pyridinyl, pyrimidinyl, pyridazinyl and pyrazinyl wherein Ar$_1$ is optionally substituted by one to three C$_{1-5}$ alkyl, C$_{1-5}$ alkoxy, C$_{1-5}$ acyl, C$_{1-5}$ acylamino, amino, cyano, hydroxyl or halogen;

Ar$_2$ is chosen from phenyl, oxazolyl, isoxazolyl, oxadiazolyl, thiazolyl, pyrazolyl, pyrrolyl, imidazolyl, pyridinyl, pyrimidinyl, pyridazinyl and pyrazinyl wherein Ar$_2$ is optionally substituted by one to three C$_{1-5}$ alkyl, C$_{1-5}$ alkoxy-(CH$_2$)$_n$—, C$_{1-5}$ alkoxycarbonyl-(CH$_2$)$_n$—, carboxy-(CH$_2$)$_n$—, C$_{1-5}$ acyl, C$_{1-5}$ acylamino, amino, cyano, hydroxyl, oxo or halogen.

In another embodiment, there is provided a compound of the formula (I) or formula (II) according the embodiment described immediately above, and wherein Het is a ring chosen from pyrazolyl, imidazolyl and pyridinyl each optionally substituted by one to three C$_{1-5}$ alkyl, C$_{1-5}$ alkoxy, C$_{1-5}$ acyl, C$_{1-5}$ acylamino, amino, cyano, hydroxyl or halogen;

Ar$_1$ is chosen from phenyl, oxazolyl, 4,5-dihydro-oxazolyl, isoxazolyl, oxadiazolyl, pyrazolyl, imidazolyl, pyridinyl and pyrimidinyl wherein Ar$_1$ is optionally substituted by one to two C$_{1-5}$ alkyl or halogen;

Ar$_2$ is chosen from phenyl, pyridinyl, pyrimidinyl, pyridazinyl and pyrazinyl wherein Ar$_2$ is optionally substituted by one to three C$_{1-5}$ alkyl, C$_{1-5}$ alkoxy, C$_{1-5}$ alkoxycarbonyl, carboxy, or halogen.

In another embodiment, there is provided a compound of the formula (I) or formula (II) according the embodiment described immediately above, and wherein Het is a ring chosen from pyrazolyl, imidazolyl and pyridinyl each optionally substituted by C$_{1-5}$ alkyl, C$_{1-5}$ alkoxy or halogen;

R$_1$ is chosen from C$_{1-2}$ alkoxyC$_{1-2}$ alkyl, C$_{1-2}$ alkoxycarbonyl and Ar$_1$;

R$_2$ is chosen from Ar$_2$—CH$_2$—;

Ar$_1$ is chosen from phenyl, 4,5-dihydro-oxazolyl, oxadiazolyl, pyrazolyl, pyridinyl and pyrimidinyl wherein Ar$_1$ is optionally substituted by one to two C$_{1-3}$ alkyl or halogen;

Ar$_2$ is chosen from phenyl and pyridinyl wherein Ar$_2$ is optionally substituted by one to two C$_{1-5}$ alkyl, C$_{1-5}$ alkoxy, C$_{1-5}$ alkoxycarbonyl, hydroxyl, oxo, carboxy, or halogen.

In another embodiment, there is provided a compound of the formula (I) or formula (II) according the embodiment described immediately above, and wherein Het is chosen from

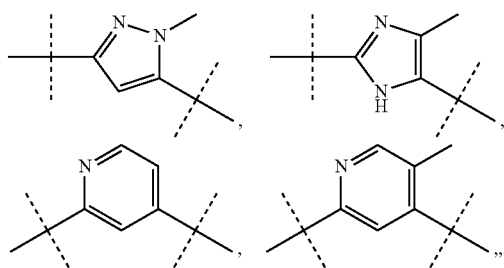

R₂ is chosen from

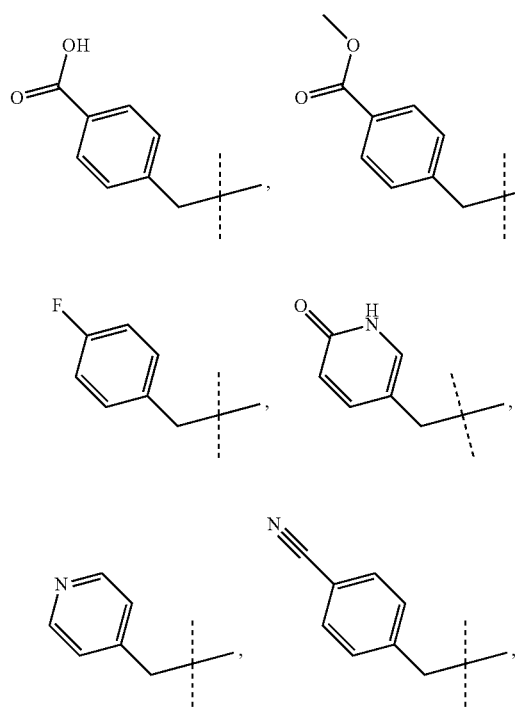

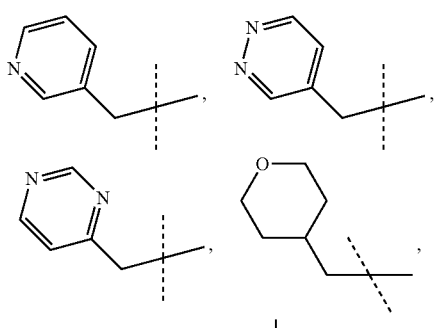

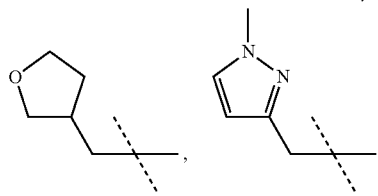

R₁ is chosen from

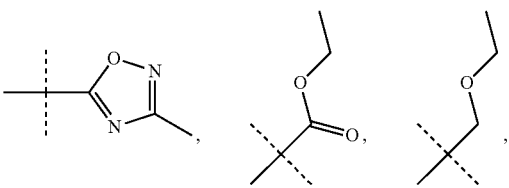

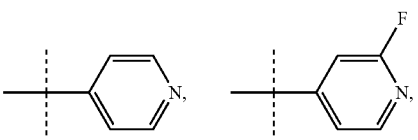

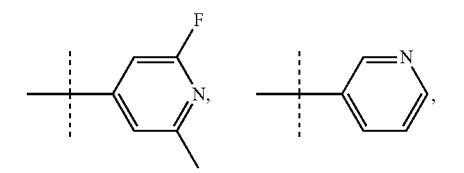

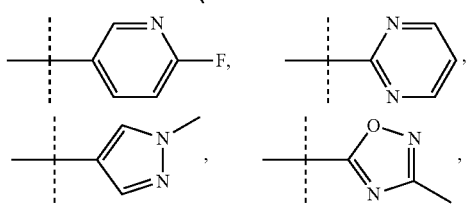

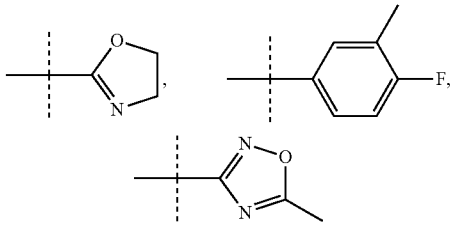

In another embodiment, there is provided a compound of the formula (I) or formula (II) according the first generic embodiment, wherein R₂ is hydrogen or $C_{1-4}$ alkyl;

R₁ is chosen from $C_{1-5}$ alkoxy$C_{1-5}$ alkyl, $C_{1-5}$ alkoxycarbonyl- and

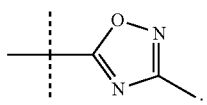

In another embodiment, there is provided a compound of the formula (I) or formula (II) according the embodiment described immediately above, and wherein X is —O—;

R₁ is $C_{1-5}$ alkoxycarbonyl-.

In another embodiment, the invention provides compounds in Table I which can be made in view of the general schemes, examples and methods known in the art.

TABLE I

| | |
|---|---|
| 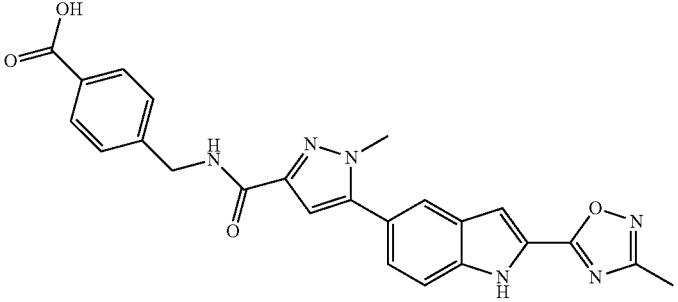 [SMILES: Cc1noc(-c2cc3cc(-c4cc(C(=O)NCc5ccc(C(=O)O)cc5)nn4C)ccc3[nH]2)n1] | 4-[({1-Methyl-5-[2-(3-methyl-1,2,4-oxadiazol-5-yl)-1H-indol-5-yl]-1H-pyrazole-3-carbonyl}-amino)-methyl]-benzoic acid |
| 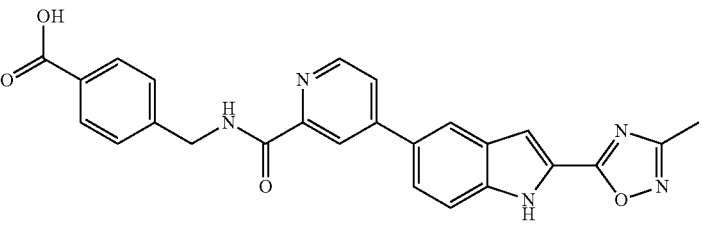 [SMILES: Cc1noc(-c2cc3cc(-c4ccnc(C(=O)NCc5ccc(C(=O)O)cc5)c4)ccc3[nH]2)n1] | 4-[({4-[2-(3-Methyl-1,2,4-oxadiazol-5-yl)-1H-indol-5-yl]-pyridine-2-carbonyl}-amino)-methyl]-benzoic acid |
| 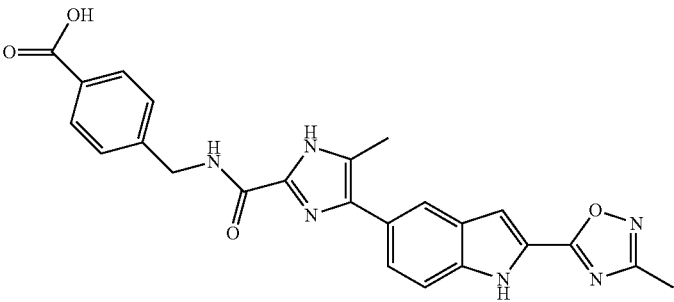 [SMILES: Cc1noc(-c2cc3cc(-c4nc(C(=O)NCc5ccc(C(=O)O)cc5)[nH]c4C)ccc3[nH]2)n1] | 4-[({5-Methyl-4-[2-(3-methyl-1,2,4-oxadiazol-5-yl)-1H-indol-5-yl]-1H-imidazole-2-carbonyl}-amino)-methyl]-benzoic acid |
| 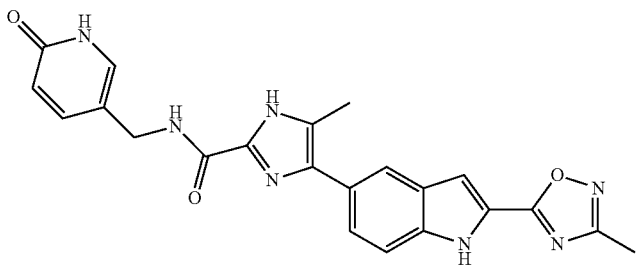 [SMILES: Cc1noc(-c2cc3cc(-c4nc(C(=O)NCc5ccc(=O)[nH]c5)[nH]c4C)ccc3[nH]2)n1] | 5-Methyl-4-[2-(3-methyl-1,2,4-oxadiazol-5-yl)-1H-indol-5-yl]-1H-imidazole-2-carboxylic acid (6-oxo-1,6-dihydro-pyridin-3-ylmethyl)-amide |
| 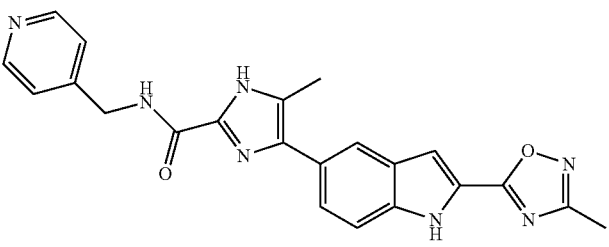 | 5-Methyl-4-[2-(3-methyl-1,2,4-oxadiazol-5-yl)-1H-indol-5-yl]-1H-imidazole-2-carboxylic acid (pyridin-4-ylmethyl)-amide |
| 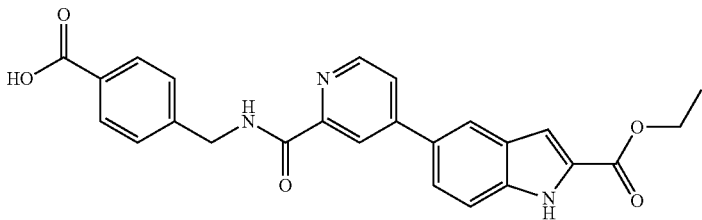 [SMILES: CCOC(=O)c1cc2cc(-c3ccnc(C(=O)NCc4ccc(C(=O)O)cc4)c3)ccc2[nH]1] | 5-[2-(4-Carboxy-benzylcarbamoyl)-pyridin-4-yl]-1H-indole-2-carboxylic acid ethyl ester |

TABLE I-continued

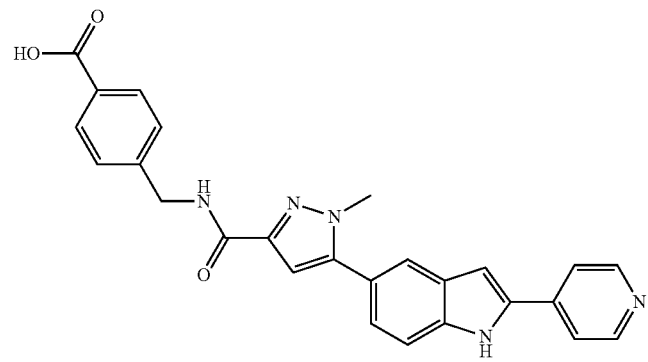 [SMILES: Cn1nc(C(=O)NCc2ccc(C(=O)O)cc2)cc1-c1ccc2[nH]c(-c3ccncc3)cc2c1]

4-({[1-Methyl-5-(2-pyridin-4-yl-1H-indol-5-yl)-1H-pyrazole-3-carbonyl]-amino}-methyl)-benzoic acid

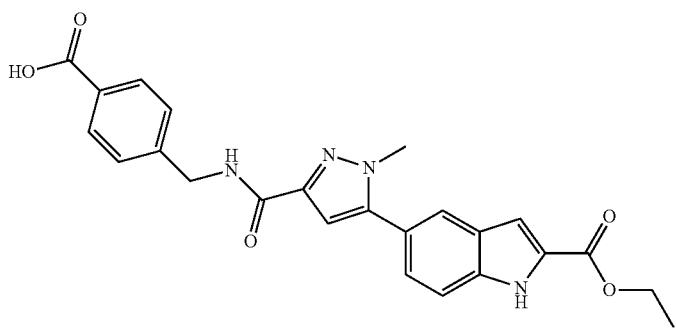 [SMILES: CCOC(=O)c1cc2cc(-c3cc(C(=O)NCc4ccc(C(=O)O)cc4)nn3C)ccc2[nH]1]

5-[5-(4-Carboxy-benzylcarbamoyl)-2-methyl-2H-pyrazol-3-yl]-1H-indole-2-carboxylic acid ethyl ester

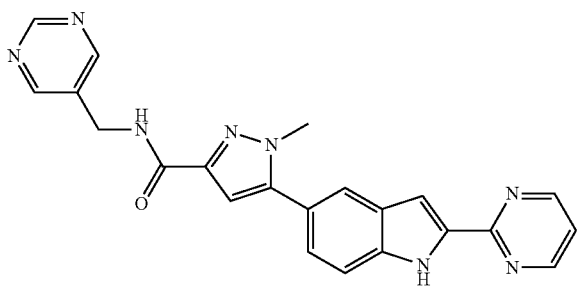 [SMILES: Cn1nc(C(=O)NCc2cncnc2)cc1-c1ccc2[nH]c(-c3ncccn3)cc2c1]

4-({[1-Methyl-5-(2-pyrimidin-2-yl-1H-indol-5-yl)-1H-pyrazole-3-carbonyl]-amino}-methyl)-benzoic acid

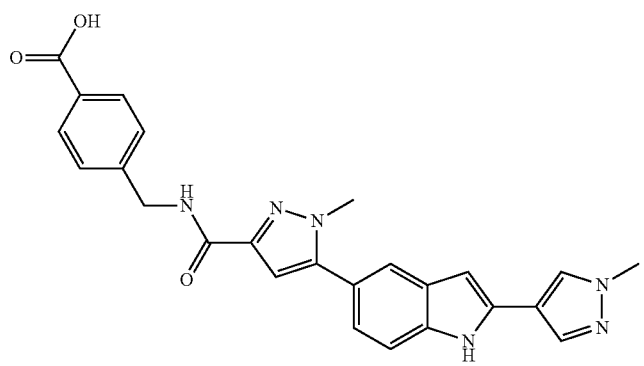 [SMILES: Cn1cc(-c2cc3cc(-c4cc(C(=O)NCc5ccc(C(=O)O)cc5)nn4C)ccc3[nH]2)cn1]

4-[({1-Methyl-5-[2-(1-methyl-1H-pyrazol-4-yl)-1H-indol-5-yl]-1H-pyrazole-3-carbonyl}-amino)-methyl]-benzoic acid

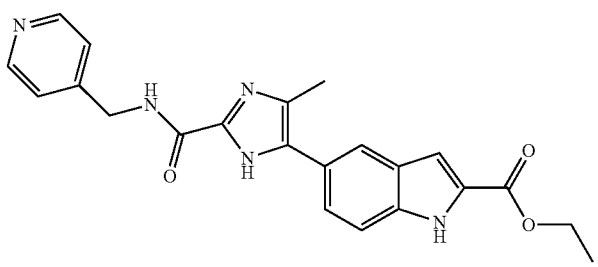 [SMILES: CCOC(=O)c1cc2cc(-c3[nH]c(C(=O)NCc4ccncc4)nc3C)ccc2[nH]1]

5-{5-Methyl-2-[(pyridin-4-ylmethyl)-carbamoyl]-3H-imidazol-4-yl}-1H-indole-2-carboxylic acid ethyl ester TABLE I-continued

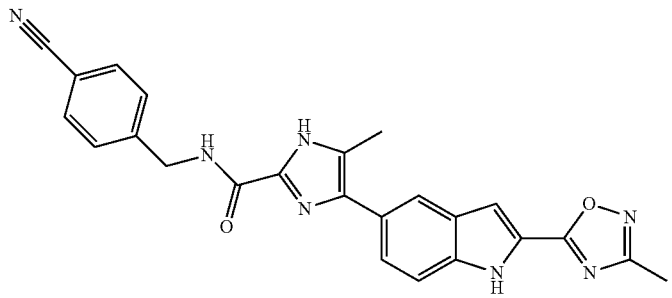 [SMILES: Cc1noc(-c2cc3cc(-c4nc(C(=O)NCc5ccc(C#N)cc5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid 4-cyano-benzylamide

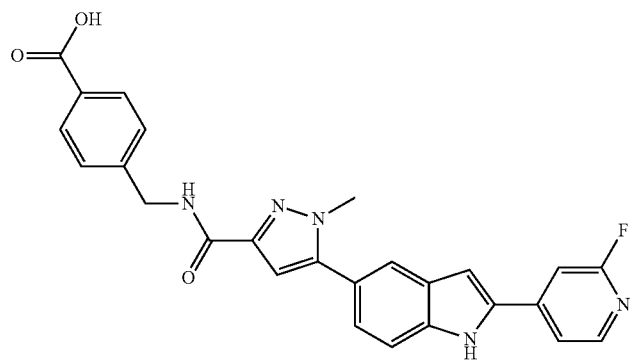 [SMILES: Cn1nc(C(=O)NCc2ccc(C(=O)O)cc2)cc1-c1ccc2[nH]c(-c3ccnc(F)c3)cc2c1]

4-[({5-[2-(2-Fluoro-pyridin-4-yl)-1H-indol-5-yl]-1-methyl-1H-pyrazole-3-carbonyl}-amino)-methyl]-benzoic acid

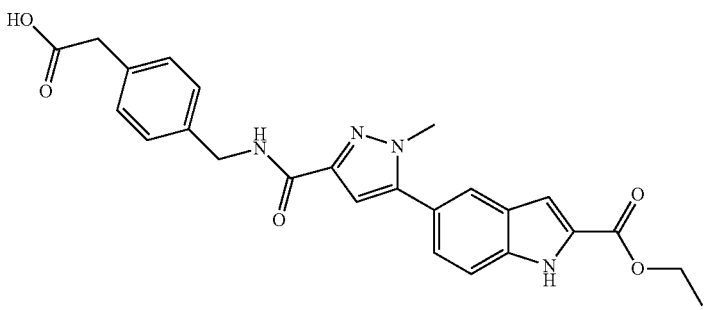 [SMILES: CCOC(=O)c1cc2cc(-c3cc(C(=O)NCc4ccc(CC(=O)O)cc4)nn3C)ccc2[nH]1]

5-[5-(4-Carboxymethyl-benzylcarbamoyl)-2-methyl-2H-pyrazol-3-yl]-1H-indole-2-carboxylic acid ethyl ester

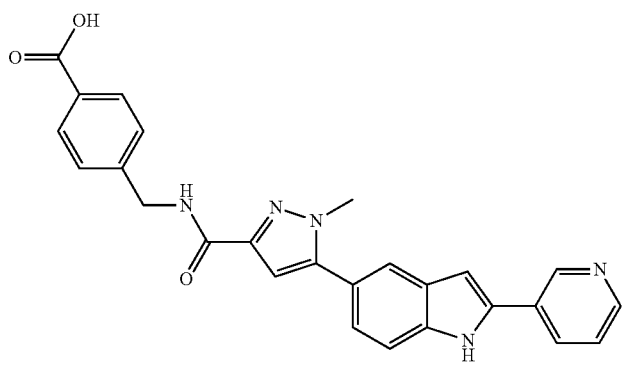 [SMILES: Cn1nc(C(=O)NCc2ccc(C(=O)O)cc2)cc1-c1ccc2[nH]c(-c3cccnc3)cc2c1]

4-({[1-Methyl-5-(2-pyridin-3-yl-1H-indol-5-yl)-1H-pyrazole-3-carbonyl]-amino}-methyl)-benzoic acid

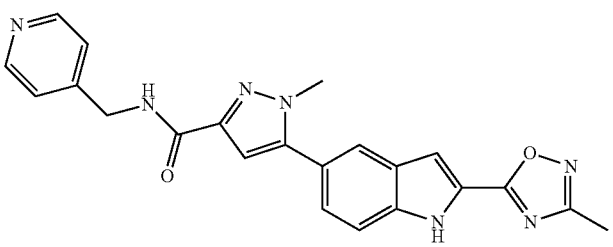 [SMILES: Cc1noc(-c2cc3cc(-c4cc(C(=O)NCc5ccncc5)nn4C)ccc3[nH]2)n1]

1-Methyl-5-[2-(3-methyl-1,2,4-oxadiazol-5-yl)-1H-indol-5-yl]-1H-pyrazole-3-carboxylic acid (pyridin-4-ylmethyl)-amide TABLE I-continued

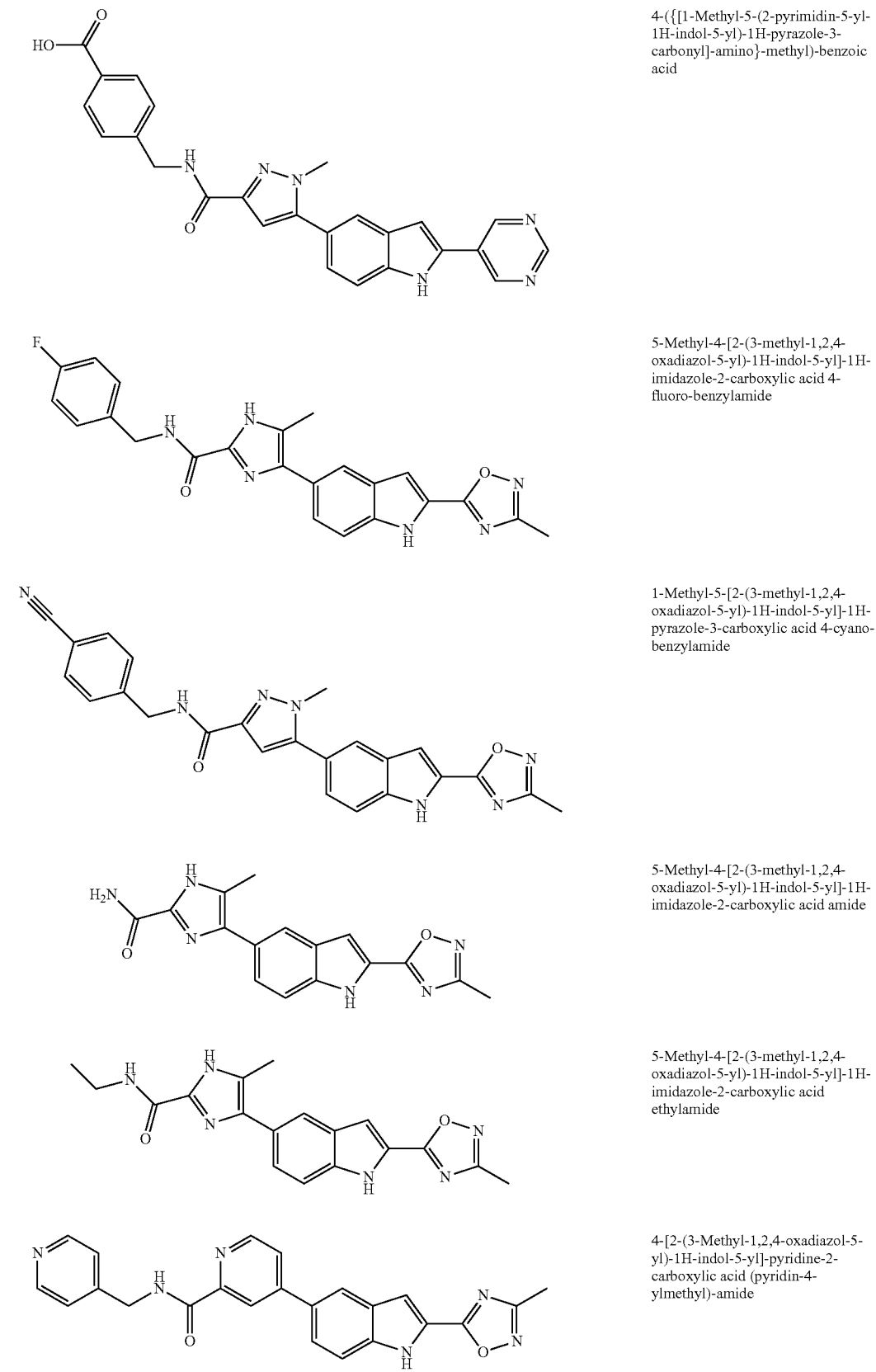

4-({[1-Methyl-5-(2-pyrimidin-5-yl-1H-indol-5-yl)-1H-pyrazole-3-carbonyl]-amino}-methyl)-benzoic acid 5-Methyl-4-[2-(3-methyl-1,2,4-oxadiazol-5-yl)-1H-indol-5-yl]-1H-imidazole-2-carboxylic acid 4-fluoro-benzylamide 1-Methyl-5-[2-(3-methyl-1,2,4-oxadiazol-5-yl)-1H-indol-5-yl]-1H-pyrazole-3-carboxylic acid 4-cyano-benzylamide 5-Methyl-4-[2-(3-methyl-1,2,4-oxadiazol-5-yl)-1H-indol-5-yl]-1H-imidazole-2-carboxylic acid amide 5-Methyl-4-[2-(3-methyl-1,2,4-oxadiazol-5-yl)-1H-indol-5-yl]-1H-imidazole-2-carboxylic acid ethylamide 4-[2-(3-Methyl-1,2,4-oxadiazol-5-yl)-1H-indol-5-yl]-pyridine-2-carboxylic acid (pyridin-4-ylmethyl)-amide TABLE I-continued

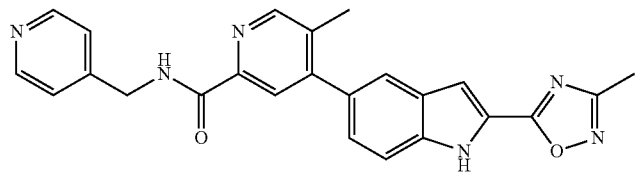 [SMILES: Cc1noc(-c2cc3cc(-c4cc(C(=O)NCc5ccncc5)ncc4C)ccc3[nH]2)n1]

5-Methyl-4-[2-(3-methyl-1,2,4-oxadiazol-5-yl)-1H-indol-5-yl]-pyridine-2-carboxylic acid (pyridin-4-ylmethyl)-amide

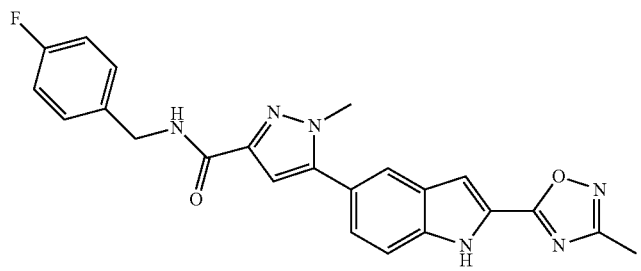 [SMILES: Cc1noc(-c2cc3cc(-c4cc(C(=O)NCc5ccc(F)cc5)nn4C)ccc3[nH]2)n1]

1-Methyl-5-[2-(3-methyl-1,2,4-oxadiazol-5-yl)-1H-indol-5-yl]-1H-pyrazole-3-carboxylic acid 4-fluoro-benzylamide

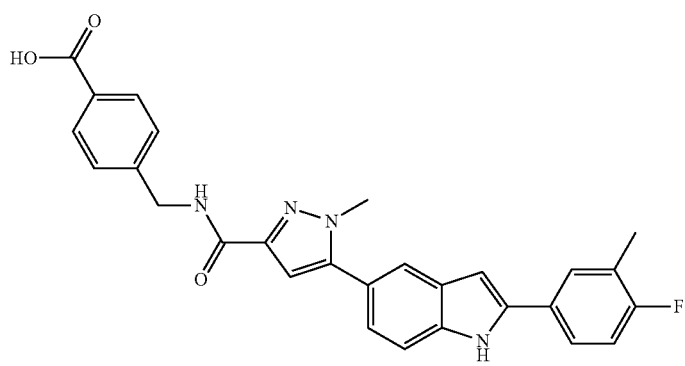 [SMILES: Cc1cc(-c2cc3cc(-c4cc(C(=O)NCc5ccc(C(=O)O)cc5)nn4C)ccc3[nH]2)ccc1F]

4-[({5-[2-(4-Fluoro-3-methyl-phenyl)-1H-indol-5-yl]-1-methyl-1H-pyrazole-3-carbonyl}-amino)-methyl]-benzoic acid

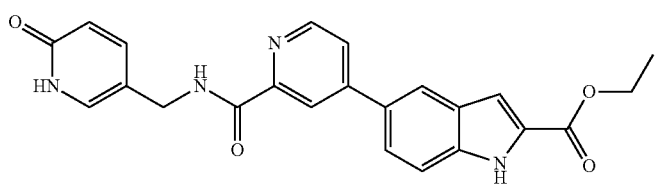 [SMILES: CCOC(=O)c1cc2cc(-c3ccnc(C(=O)NCc4ccc(=O)[nH]c4)c3)ccc2[nH]1]

5-{2-[(6-Oxo-1,6-dihydro-pyridin-3-ylmethyl)-carbamoyl]-pyridin-4-yl}-1H-indole-2-carboxylic acid ethyl ester

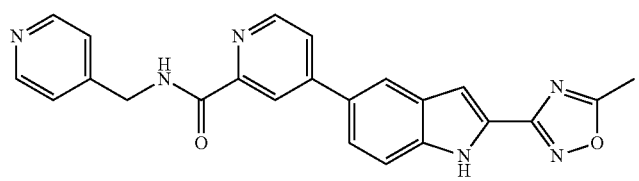 [SMILES: Cc1nc(-c2cc3cc(-c4ccnc(C(=O)NCc5ccncc5)c4)ccc3[nH]2)no1]

4-[2-(5-Methyl-1,2,4-oxadiazol-3-yl)-1H-indol-5-yl]-pyridine-2-carboxylic acid (pyridin-4-ylmethyl)-amide

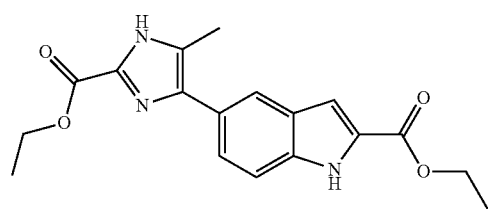 [SMILES: CCOC(=O)c1cc2cc(-c3nc(C(=O)OCC)[nH]c3C)ccc2[nH]1]

5-(2-Ethoxycarbonyl-5-methyl-1H-imidazol-4-yl)-1H-indole-2-carboxylic acid ethyl ester TABLE I-continued

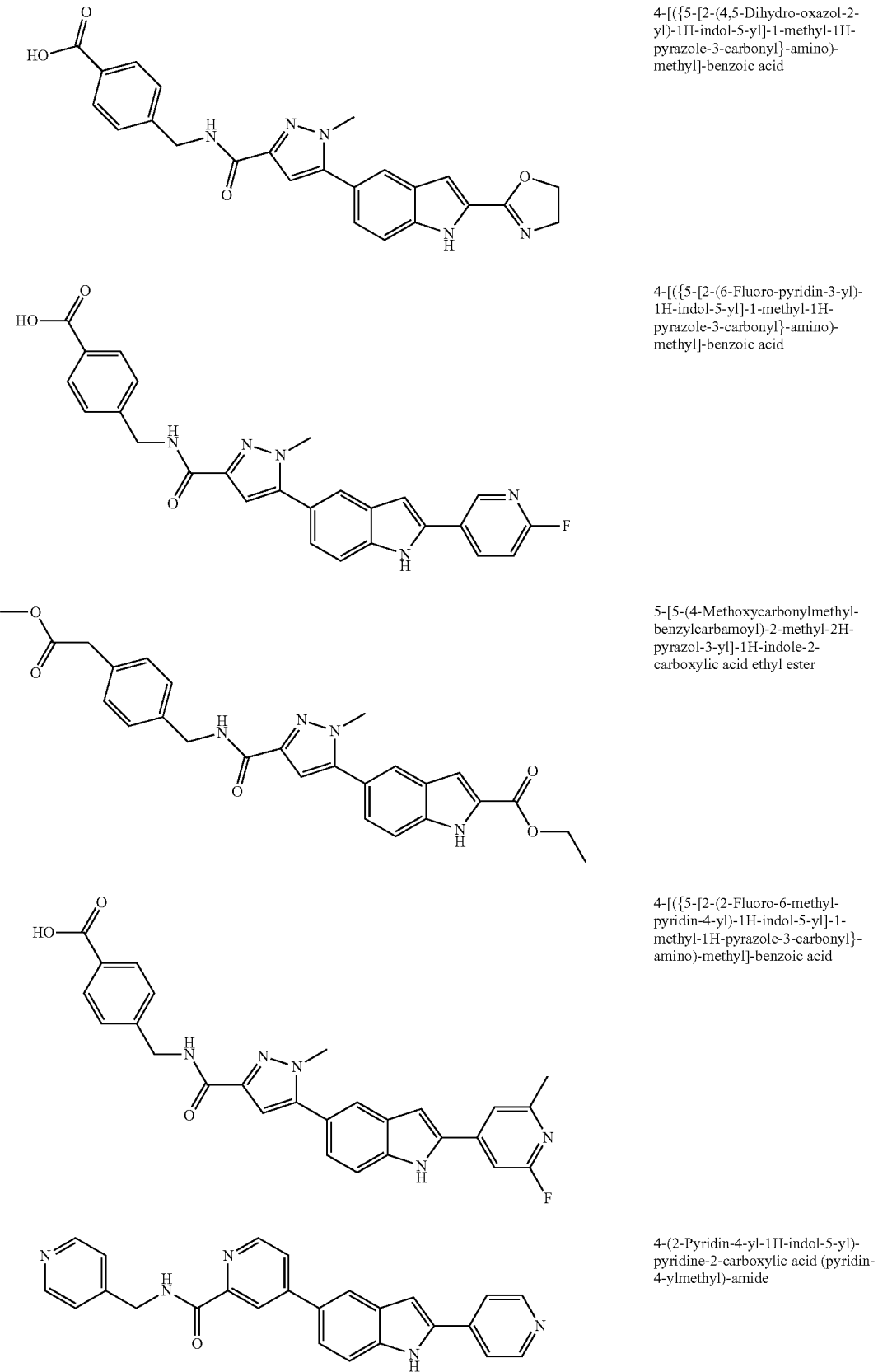

4-[({5-[2-(4,5-Dihydro-oxazol-2-yl)-1H-indol-5-yl]-1-methyl-1H-pyrazole-3-carbonyl}-amino)-methyl]-benzoic acid 4-[({5-[2-(6-Fluoro-pyridin-3-yl)-1H-indol-5-yl]-1-methyl-1H-pyrazole-3-carbonyl}-amino)-methyl]-benzoic acid 5-[5-(4-Methoxycarbonylmethyl-benzylcarbamoyl)-2-methyl-2H-pyrazol-3-yl]-1H-indole-2-carboxylic acid ethyl ester 4-[({5-[2-(2-Fluoro-6-methyl-pyridin-4-yl)-1H-indol-5-yl]-1-methyl-1H-pyrazole-3-carbonyl}-amino)-methyl]-benzoic acid 4-(2-Pyridin-4-yl-1H-indol-5-yl)-pyridine-2-carboxylic acid (pyridin-4-ylmethyl)-amide TABLE I-continued

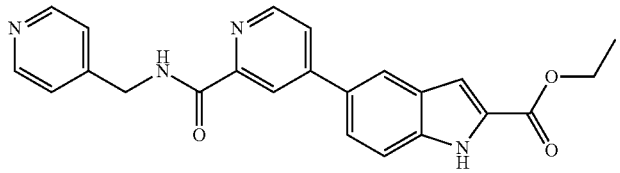 [SMILES: CCOC(=O)c1cc2cc(-c3ccnc(C(=O)NCc4ccncc4)c3)ccc2[nH]1]

5-{2-[(Pyridin-4-ylmethyl)-carbamoyl]-pyridin-4-yl}-1H-indole-2-carboxylic acid ethyl ester

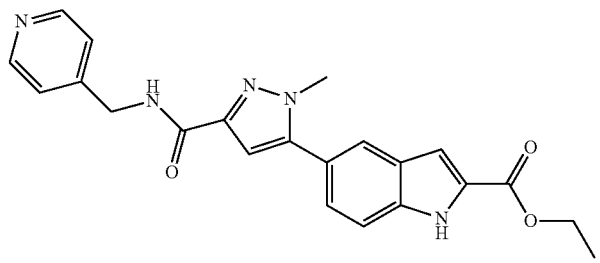 [SMILES: CCOC(=O)c1cc2cc(-c3cc(C(=O)NCc4ccncc4)nn3C)ccc2[nH]1]

5-{2-Methyl-5-[(pyridin-4-ylmethyl)-carbamoyl]-2H-pyrazol-3-yl}-1H-indole-2-carboxylic acid ethyl ester

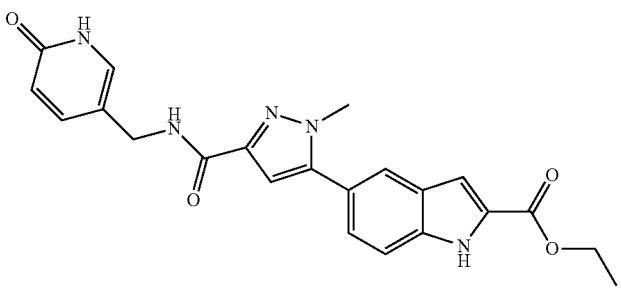 [SMILES: CCOC(=O)c1cc2cc(-c3cc(C(=O)NCc4ccc(=O)[nH]c4)nn3C)ccc2[nH]1]

5-{2-Methyl-5-[(6-oxo-1,6-dihydro-pyridin-3-ylmethyl)-carbamoyl]-2H-pyrazol-3-yl}-1H-indole-2-carboxylic acid ethyl ester

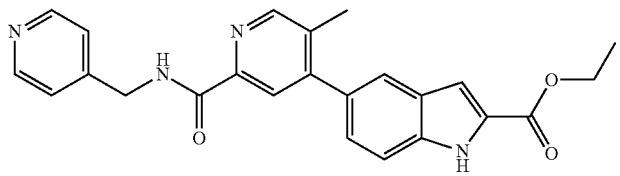 [SMILES: CCOC(=O)c1cc2cc(-c3cc(C(=O)NCc4ccncc4)ncc3C)ccc2[nH]1]

5-{5-Methyl-2-[(pyridin-4-ylmethyl)-carbamoyl]-pyridin-4-yl}-1H-indole-2-carboxylic acid ethyl ester

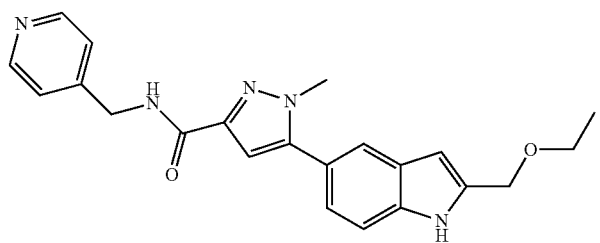 [SMILES: CCOCc1cc2cc(-c3cc(C(=O)NCc4ccncc4)nn3C)ccc2[nH]1]

4-({[5-(2-Ethoxymethyl-1H-indol-5-yl)-1-methyl-1H-pyrazole-3-carbonyl]-amino}-methyl)-4-pyridine

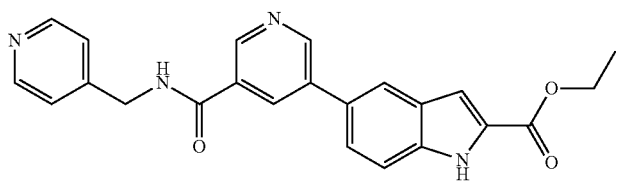 [SMILES: CCOC(=O)c1cc2cc(-c3cncc(C(=O)NCc4ccncc4)c3)ccc2[nH]1]

5-{5-[(Pyridin-4-ylmethyl)-carbamoyl]-pyridin-3-yl}-1H-indole-2-carboxylic acid ethyl ester

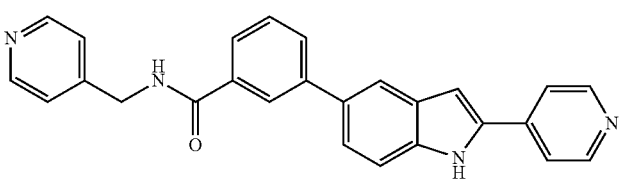 [SMILES: O=C(NCc1ccncc1)c1cccc(-c2ccc3[nH]c(-c4ccncc4)cc3c2)c1]

3-(2-Pyridin-4-yl-1H-indol-5-yl)-N-pyridin-4-ylmethyl-benzamide

TABLE I-continued

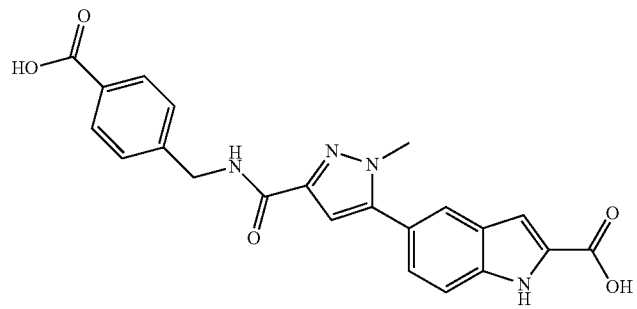 [SMILES: Cn1nc(C(=O)NCc2ccc(C(=O)O)cc2)cc1-c1ccc2[nH]c(C(=O)O)cc2c1]

5-[5-(4-Carboxy-benzylcarbamoyl)-2-methyl-2H-pyrazol-3-yl]-1H-indole-2-carboxylic acid

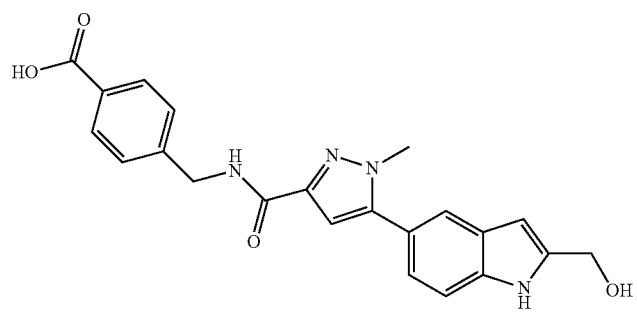 [SMILES: Cn1nc(C(=O)NCc2ccc(C(=O)O)cc2)cc1-c1ccc2[nH]c(CO)cc2c1]

4-({[5-(2-Hydroxymethyl-1H-indol-5-yl)-1-methyl-1H-pyrazole-3-carbonyl]-amino}-methyl)-benzoic acid

5-{2-[(Pyridin-4-ylmethyl)-carbamoyl]-pyridin-4-yl}-1H-indole-2-carboxylic acid methoxy-amide

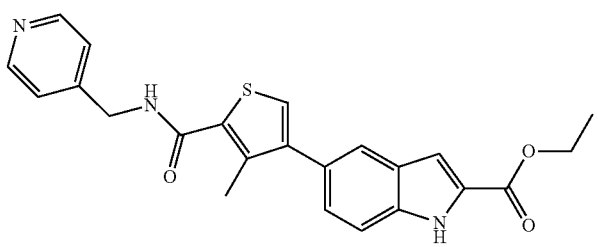

5-{4-Methyl-5-[(pyridin-4-ylmethyl)-carbamoyl]-thiophen-3-yl}-1H-indole-2-carboxylic acid ethyl ester

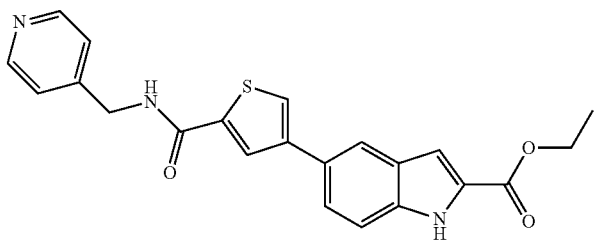 [SMILES: CCOC(=O)c1cc2cc(-c3csc(C(=O)NCc4ccncc4)c3)ccc2[nH]1]

5-{5-[(Pyridin-4-ylmethyl)-carbamoyl]-thiophen-3-yl}-1H-indole-2-carboxylic acid ethyl ester

5-{2-[(Pyridin-4-ylmethyl)-carbamoyl]-pyridin-4-yl}-1H-indole-2-carboxylic acid tert-butyl ester TABLE I-continued

| Structure | Name |
|---|---|
| (structure) | 5-{2-[(Pyridin-4-ylmethyl)-carbamoyl]-pyridin-4-yl}-1H-indole-2-carboxylic acid (2-hydroxy-ethyl)-amide |
| (structure) | 5-{2-[(Pyridin-4-ylmethyl)-carbamoyl]-pyridin-4-yl}-1H-indole-2-carboxylic acid |
| (structure) | 5-(4-Carbamoyl-pyridin-2-yl)-1H-indole-2-carboxylic acid ethyl ester |
| (structure) | 5-{3-[(1,3-Benzodioxol-5-ylmethyl)-carbamoyl]-phenyl}-1H-indole-2-carboxylic acid ethyl ester |
| (structure) | 5-[2-(4-Fluoro-3-methyl-benzylcarbamoyl)-pyridin-4-yl]-1H-indole-2-carboxylic acid ethyl ester |
| (structure) | 5-[2-(4-Benzyloxycarbonyl-benzylcarbamoyl)-pyridin-4-yl]-1H-indole-2-carboxylic acid ethyl ester |
| (structure) | 5-{2-[(Pyridin-4-ylmethyl)-carbamoyl]-pyridin-4-yl}-1H-indole-2-carboxylic acid pyridin-4-ylamide |
| (structure) | 5-{2-[(Pyridin-4-ylmethyl)-carbamoyl]-pyridin-4-yl}-1H-indole-2-carboxylic acid methoxy-methyl-amide |

TABLE I-continued

| | |
|---|---|
| 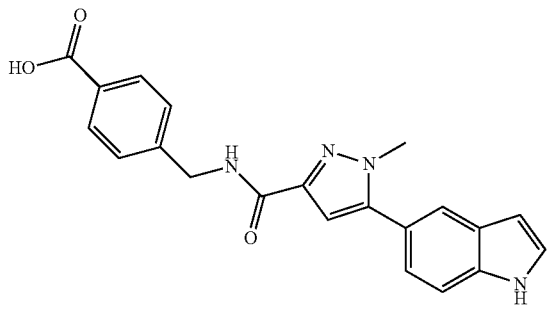 [SMILES: Cn1nc(C(=O)NCc2ccc(C(=O)O)cc2)cc1-c1ccc2[nH]ccc2c1] | 4-({[5-(1H-Indol-5-yl)-1-methyl-1H-pyrazole-3-carbonyl]-amino}-methyl)-benzoic acid |
| 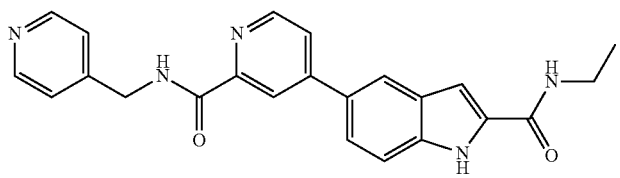 [SMILES: CCNC(=O)c1cc2cc(-c3ccnc(C(=O)NCc4ccncc4)c3)ccc2[nH]1] | 5-{2-[(Pyridin-4-ylmethyl)-carbamoyl]-pyridin-4-yl}-1H-indole-2-carboxylic acid ethylamide |
| 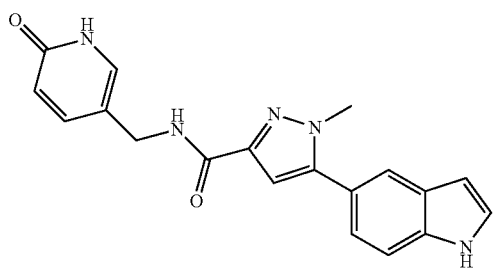 [SMILES: Cn1nc(C(=O)NCc2ccc(=O)[nH]c2)cc1-c1ccc2[nH]ccc2c1] | 5-(1H-Indol-5-yl)-1-methyl-1H-pyrazole-3-carboxylic acid (6-oxo-1,6-dihydro-pyridin-3-ylmethyl)-amide |
| 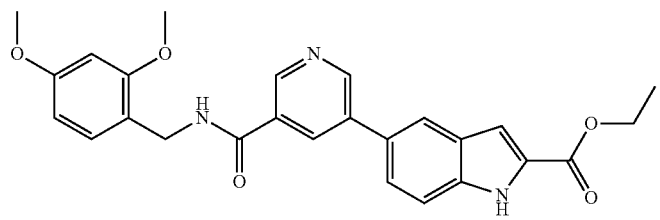 [SMILES: CCOC(=O)c1cc2cc(-c3cncc(C(=O)NCc4ccc(OC)cc4OC)c3)ccc2[nH]1] | 5-[5-(2,4-Dimethoxy-benzylcarbamoyl)-pyridin-3-yl]-1H-indole-2-carboxylic acid ethyl ester |
| 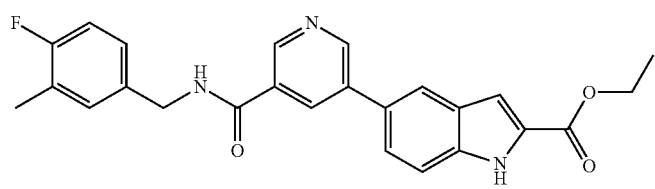 [SMILES: CCOC(=O)c1cc2cc(-c3cncc(C(=O)NCc4ccc(F)c(C)c4)c3)ccc2[nH]1] | 5-[5-(4-Fluoro-3-methyl-benzylcarbamoyl)-pyridin-3-yl]-1H-indole-2-carboxylic acid ethyl ester |
| 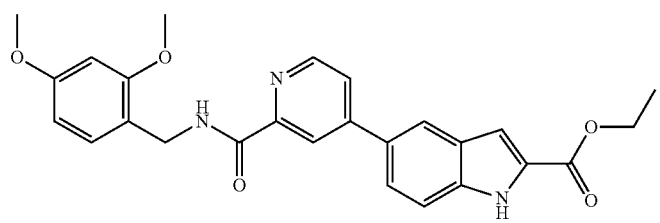 [SMILES: CCOC(=O)c1cc2cc(-c3ccnc(C(=O)NCc4ccc(OC)cc4OC)c3)ccc2[nH]1] | 5-[2-(2,4-Dimethoxy-benzylcarbamoyl)-pyridin-4-yl]-1H-indole-2-carboxylic acid ethyl ester |
| 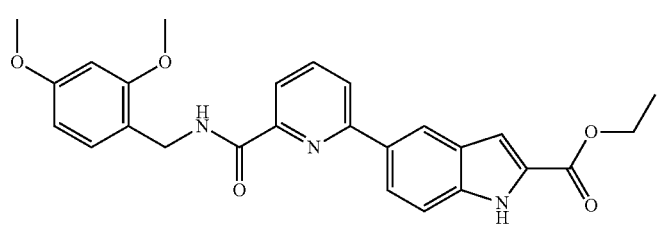 | 5-[6-(2,4-Dimethoxy-benzylcarbamoyl)-pyridin-2-yl]-1H-indole-2-carboxylic acid ethyl ester |

TABLE I-continued

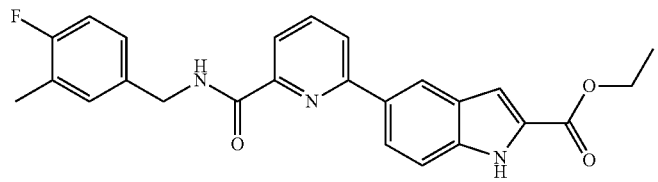 [SMILES: CCOC(=O)c1cc2cc(-c3cccc(C(=O)NCc4ccc(F)c(C)c4)n3)ccc2[nH]1]

5-[6-(4-Fluoro-3-methyl-benzylcarbamoyl)-pyridin-2-yl]-1H-indole-2-carboxylic acid ethyl ester

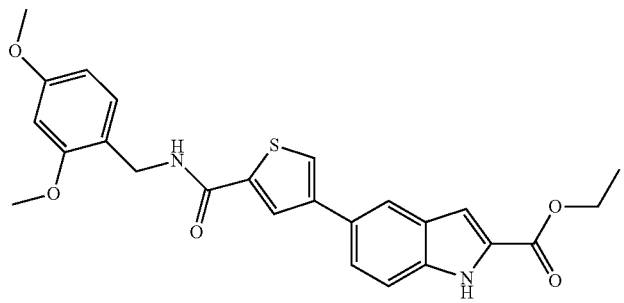 [SMILES: CCOC(=O)c1cc2cc(-c3csc(C(=O)NCc4ccc(OC)cc4OC)c3)ccc2[nH]1]

5-[5-(2,4-Dimethoxy-benzylcarbamoyl)-thiophen-3-yl]-1H-indole-2-carboxylic acid ethyl ester

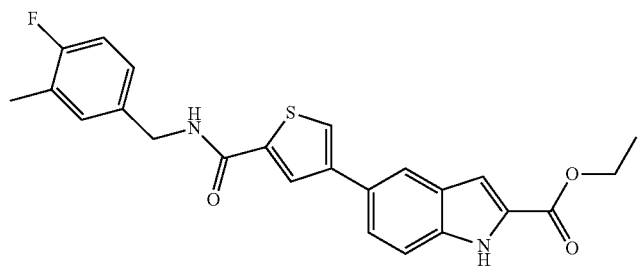 [SMILES: CCOC(=O)c1cc2cc(-c3csc(C(=O)NCc4ccc(F)c(C)c4)c3)ccc2[nH]1]

5-[5-(4-Fluoro-3-methyl-benzylcarbamoyl)-thiophen-3-yl]-1H-indole-2-carboxylic acid ethyl ester

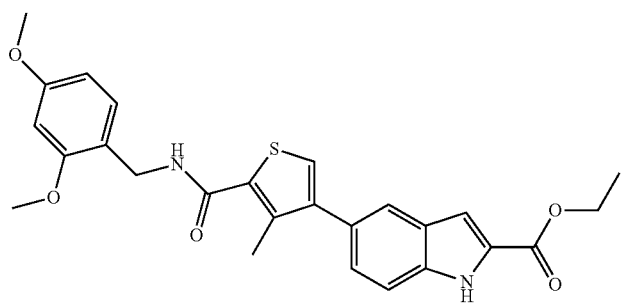 [SMILES: CCOC(=O)c1cc2cc(-c3csc(C(=O)NCc4ccc(OC)cc4OC)c3C)ccc2[nH]1]

5-[5-(2,4-Dimethoxy-benzylcarbamoyl)-4-methyl-thiophen-3-yl]-1H-indole-2-carboxylic acid ethyl ester

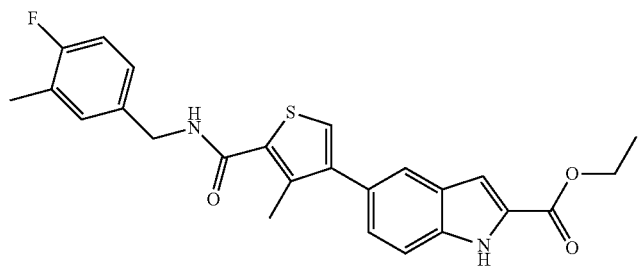 [SMILES: CCOC(=O)c1cc2cc(-c3csc(C(=O)NCc4ccc(F)c(C)c4)c3C)ccc2[nH]1]

5-[5-(4-Fluoro-3-methyl-benzylcarbamoyl)-4-methyl-thiophen-3-yl]-1H-indole-2-carboxylic acid ethyl ester

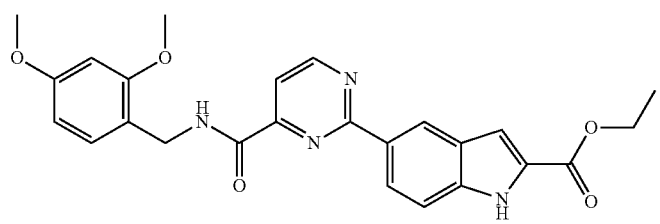 [SMILES: CCOC(=O)c1cc2cc(-c3nccc(C(=O)NCc4ccc(OC)cc4OC)n3)ccc2[nH]1]

5-[4-(2,4-Dimethoxy-benzylcarbamoyl)-pyrimidin-2-yl]-1H-indole-2-carboxylic acid ethyl ester TABLE I-continued

| Structure | Name |
|---|---|
| 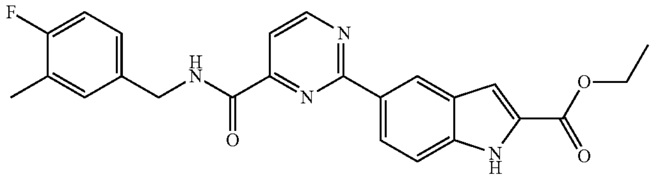 | 5-[4-(4-Fluoro-3-methyl-benzylcarbamoyl)-pyrimidin-2-yl]-1H-indole-2-carboxylic acid ethyl ester |
| 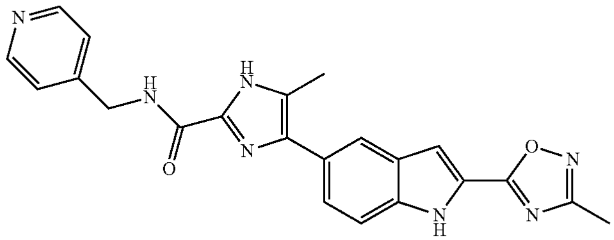 | 5-Methyl-4-[2-(3-methyl-1,2,4-oxadiazol-5-yl)-1H-indol-5-yl]-1H-imidazole-2-carboxylic acid (pyridin-4-ylmethyl)-amide |
| 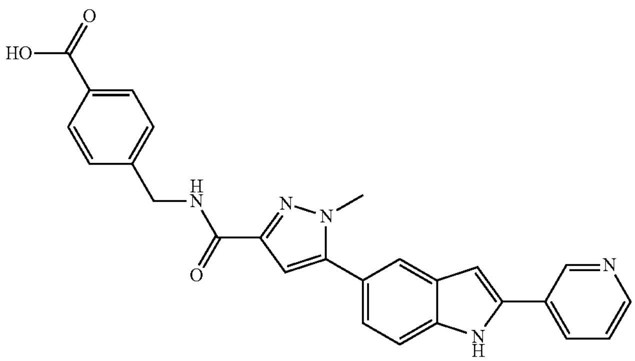 [SMILES: Cn1nc(C(=O)NCc2ccc(C(=O)O)cc2)cc1-c1ccc2[nH]c(-c3cccnc3)cc2c1] | 4-({[1-Methyl-5-(2-pyridin-3-yl-1H-indol-5-yl)-1H-pyrazole-3-carbonyl]-amino}-methyl)-benzoic acid |
| 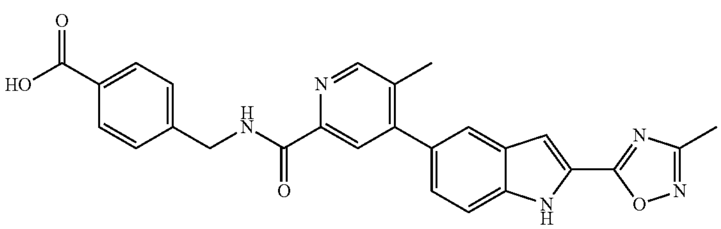 [SMILES: Cc1noc(-c2cc3cc(-c4cc(C(=O)NCc5ccc(C(=O)O)cc5)ncc4C)ccc3[nH]2)n1] | 4-[({5-Methyl-4-[2-(3-methyl-1,2,4-oxadiazol-5-yl)-1H-indol-5-yl]-pyridin-2-carbonyl}-amino)-methyl]-benzoic acid |
| 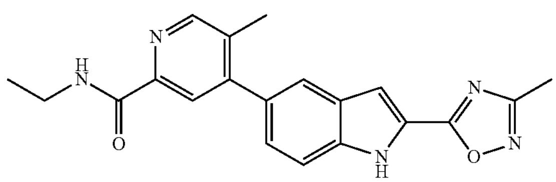 [SMILES: CCNC(=O)c1cc(-c2ccc3[nH]c(-c4nc(C)no4)cc3c2)c(C)cn1] | 5-Methyl-4-[2-(3-methyl-1,2,4-oxadiazol-5-yl)-1H-indol-5-yl]-pyridine-2-carboxylic acid ethylamide |
| 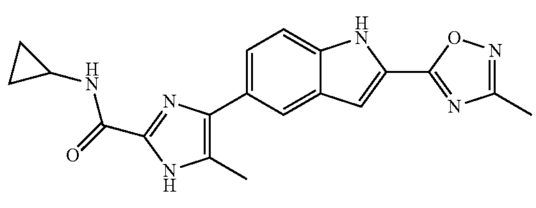 [SMILES: Cc1noc(-c2cc3cc(-c4nc(C(=O)NC5CC5)[nH]c4C)ccc3[nH]2)n1] | N-cyclopropyl-5-methyl-4-[2-(3-methyl-1,2,4-oxadiazol-5-yl)-1H-indol-5-yl]-1H-imidazole-2-carboxamide |
| 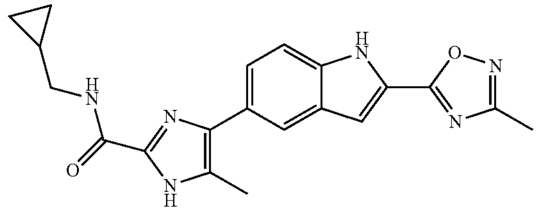 [SMILES: Cc1noc(-c2cc3cc(-c4nc(C(=O)NCC5CC5)[nH]c4C)ccc3[nH]2)n1] | N-(cyclopropylmethyl)-5-methyl-4-[2-(3-methyl-1,2,4-oxadiazol-5-yl)-1H-indol-5-yl]-1H-imidazole-2-carboxamide |

TABLE I-continued

| | |
|---|---|
| 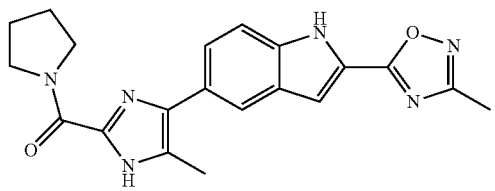 [SMILES: Cc1noc(-c2cc3cc(-c4nc(C(=O)N5CCCC5)[nH]c4C)ccc3[nH]2)n1] | {5-methyl-4-[2-(3-methyl-1,2,4-oxadiazol-5-yl)-1H-indol-5-yl]-1H-imidazol-2-yl}(pyrrolidin-1-yl)methanone |
| 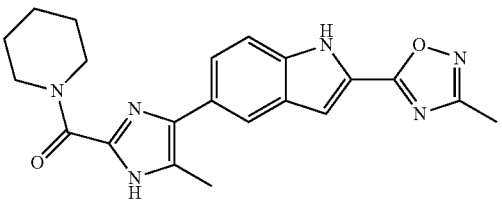 [SMILES: Cc1noc(-c2cc3cc(-c4nc(C(=O)N5CCCCC5)[nH]c4C)ccc3[nH]2)n1] | {5-methyl-4-[2-(3-methyl-1,2,4-oxadiazol-5-yl)-1H-indol-5-yl]-1H-imidazol-2-yl}(piperidin-1-yl)methanone |
| 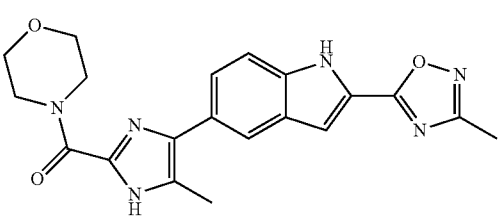 [SMILES: Cc1noc(-c2cc3cc(-c4nc(C(=O)N5CCOCC5)[nH]c4C)ccc3[nH]2)n1] | {5-methyl-4-[2-(3-methyl-1,2,4-oxadiazol-5-yl)-1H-indol-5-yl]-1H-imidazole-2-yl}(morpholin-4-yl)methanone |
| 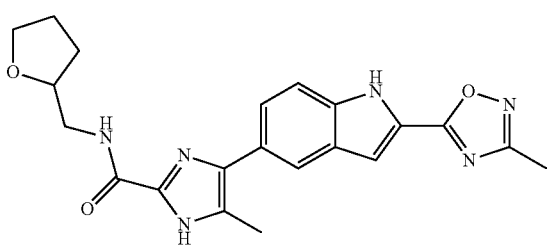 [SMILES: Cc1noc(-c2cc3cc(-c4nc(C(=O)NCC5CCCO5)[nH]c4C)ccc3[nH]2)n1] | 5-methyl-4-[2-(3-methyl-1,2,4-oxadiazol-5-yl)-1H-indol-5-yl]-N-(tetrahydrofuran-2-ylmethyl)-1H-imidazole-2-carboxamide |
| 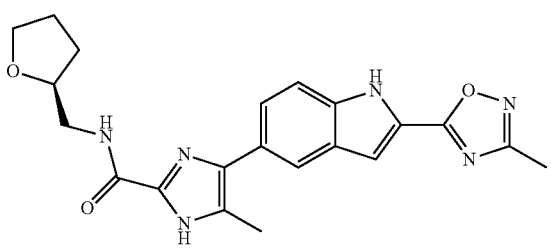 [SMILES: Cc1noc(-c2cc3cc(-c4nc(C(=O)NC[C@@H]5CCCO5)[nH]c4C)ccc3[nH]2)n1] | 5-methyl-4-[2-(3-methyl-1,2,4-oxadiazol-5-yl)-1H-indol-5-yl]-N-[(2S)-tetrahydrofuran-2-ylmethyl]-1H-imidazole-2-carboxamide |
| 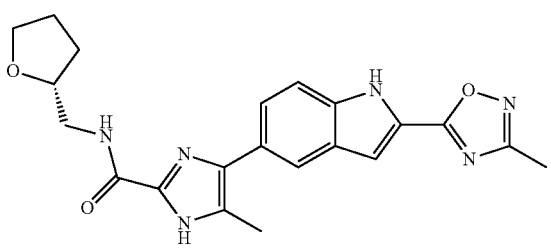 | 5-methyl-4-[2-(3-methyl-1,2,4-oxadiazol-5-yl)-1H-indol-5-yl]-N-[(2R)-tetrahydrofuran-2-ylmethyl]-1H-imidazole-2-carboxamide |
| 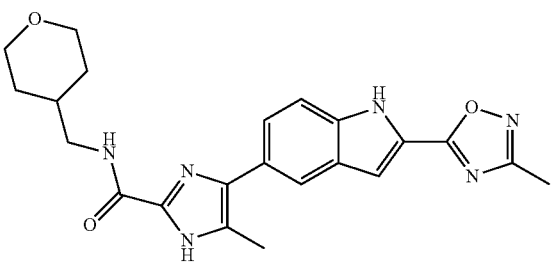 [SMILES: Cc1noc(-c2cc3cc(-c4nc(C(=O)NCC5CCOCC5)[nH]c4C)ccc3[nH]2)n1] | 5-methyl-4-[2-(3-methyl-1,2,4-oxadiazol-5-yl)-1H-indol-5-yl]-N-(tetrahydro-2H-pyran-4-ylmethyl)-1H-imidazole-2-carboxamide |

TABLE I-continued

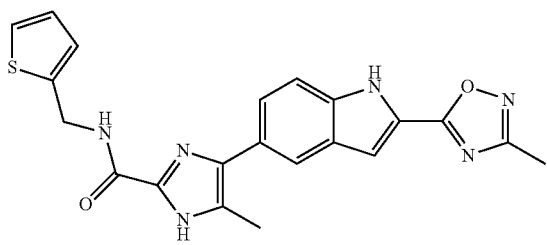 [SMILES: Cc1noc(-c2cc3cc(-c4nc(C(=O)NCc5cccs5)[nH]c4C)ccc3[nH]2)n1]

5-methyl-4-[2-(3-methyl-1,2,4-oxadiazol-5-yl)-1H-indol-5-yl]-N-(thiophen-2-ylmethyl)-1H-imidazole-2-carboxamide

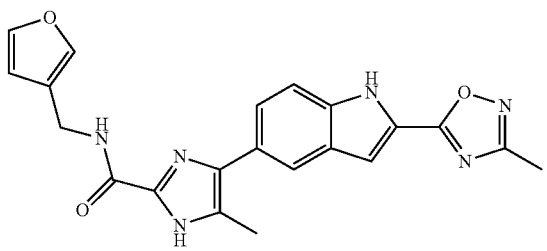 [SMILES: Cc1noc(-c2cc3cc(-c4nc(C(=O)NCc5ccoc5)[nH]c4C)ccc3[nH]2)n1]

N-(furan-3-ylmethyl)-5-methyl-4-[2-(3-methyl-1,2,4-oxadiazol-5-yl)-1H-inol-5-yl]-1H-imidazole-2-carboxamide

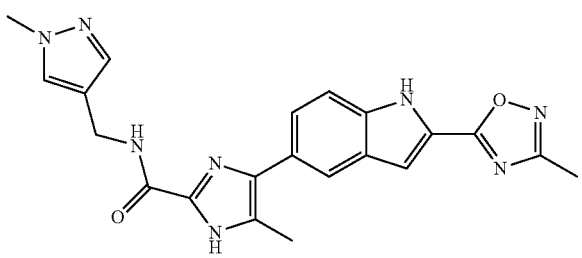

5-methyl-4-[2-(3-methyl-1,2,4-oxadiazol-5-yl)-1H-inol-5-yl]-N-[(1-methyl-1H-pyrazol-4-yl)methyl]-1H-imidazole-2-carboxamide

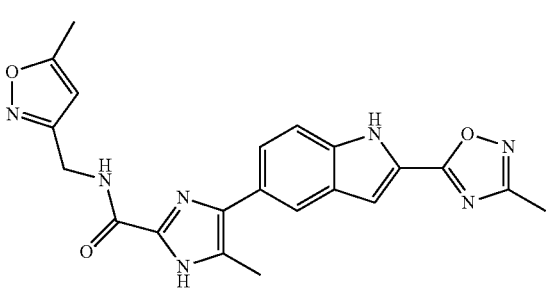 [SMILES: Cc1noc(-c2cc3cc(-c4nc(C(=O)NCc5cc(C)on5)[nH]c4C)ccc3[nH]2)n1]

5-methyl-N-[(5-methylisoxazol-3-yl)methyl]-4-[2-(3-methyl-1,2,4-oxadiazol-5-yl)-1H-indol-5-yl]-1H-imidazole-2-carboxamide

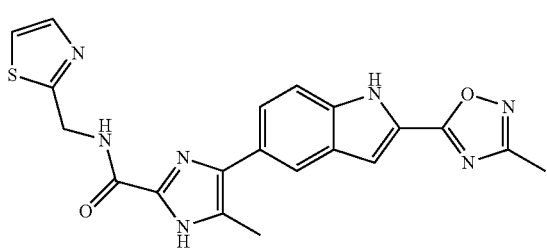 [SMILES: Cc1noc(-c2cc3cc(-c4nc(C(=O)NCc5nccs5)[nH]c4C)ccc3[nH]2)n1]

5-methyl-4-[2-(3-methyl-1,2,4-oxadiazol-5-yl)-1H-indol-5-yl]-N-(1,3-thiazol-2-ylmethyl)-1H-imidazole-2-carboxamide

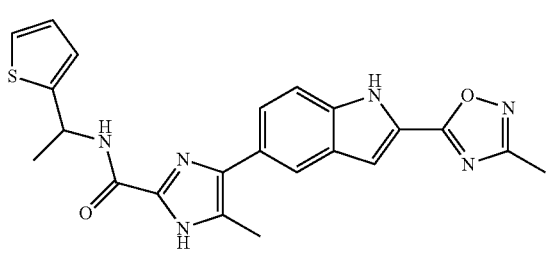 [SMILES: Cc1noc(-c2cc3cc(-c4nc(C(=O)NC(C)c5cccs5)[nH]c4C)ccc3[nH]2)n1]

5-methyl-4-[2-(3-methyl-1,2,4-oxadiazol-5-yl)-1H-indol-5-yl]-N-[1-(thiophen-2-yl)ethyl]-1H-imidazole-5-carboxamide TABLE I-continued

| | |
|---|---|
| 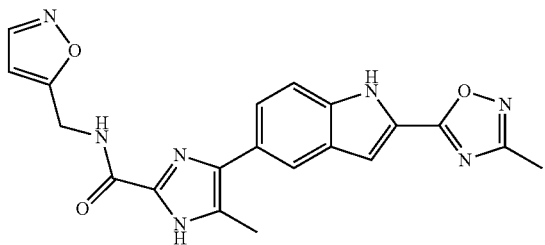 [SMILES: Cc1noc(-c2cc3cc(-c4nc(C(=O)NCc5ccno5)[nH]c4C)ccc3[nH]2)n1] | N-(isoxazol-5-ylmethyl)-5-methyl-4-[2-(3-methyl-1,2,4-oxadiazol-5-yl)-1H-indol-5-yl]-1H-imidazole-2-carboxamide |
| 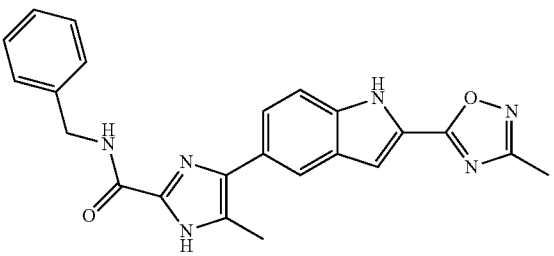 [SMILES: Cc1noc(-c2cc3cc(-c4nc(C(=O)NCc5ccccc5)[nH]c4C)ccc3[nH]2)n1] | N-benzyl-5-methyl-4-[2-(3-methyl-1,2,4-oxadiazol-5-yl)-1H-indol-5-yl]-1H-imidazole-2-carboxamide |
| 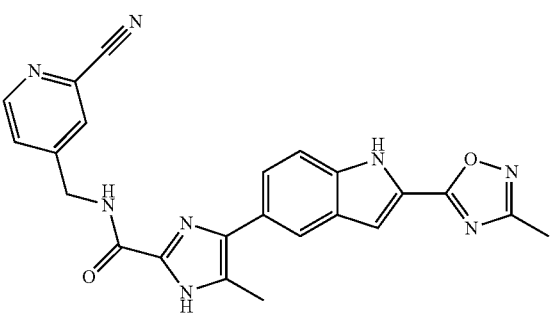 [SMILES: Cc1noc(-c2cc3cc(-c4nc(C(=O)NCc5ccnc(C#N)c5)[nH]c4C)ccc3[nH]2)n1] | N-[(2-cyanopyridin-4-yl)methyl]-5-methyl-4-[2-(3-methyl-1,2,4-oxadiazol-5-yl)-1H-indol-5-yl]-1H-imidazole-2-carboxamide |
| 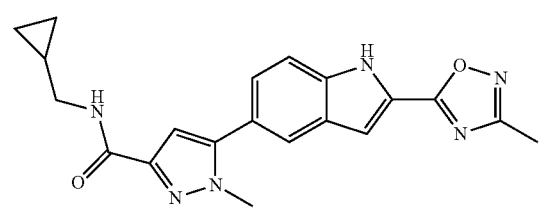 [SMILES: Cc1noc(-c2cc3cc(-c4cc(C(=O)NCC5CC5)nn4C)ccc3[nH]2)n1] | N-(cyclopropylmethyl)-1-methyl-5-[2-(3-methyl-1,2,4-oxadiazol-5-yl)-1H-indol-5-yl]-1H-pyrazole-3-carboxamide |
| 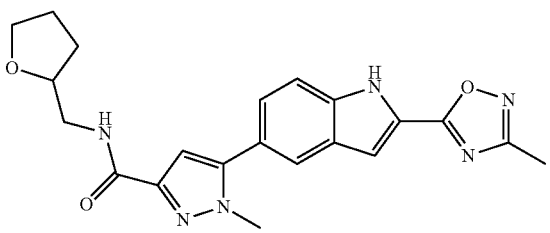 [SMILES: Cc1noc(-c2cc3cc(-c4cc(C(=O)NCC5CCCO5)nn4C)ccc3[nH]2)n1] | 1-methyl-5-[2-(3-methyl-1,2,4-oxadiazol-5-yl)-1H-indol-5-yl]-N-(tetrahydrofuran-2-ylmethyl)-1H-pyrazole-3-carboxamide |
| 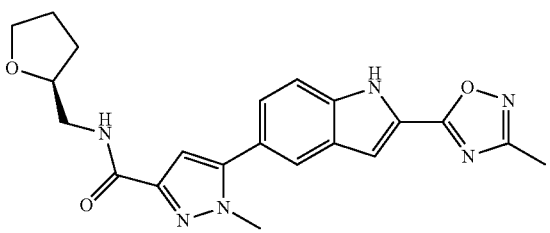 [SMILES: Cc1noc(-c2cc3cc(-c4cc(C(=O)NC[C@@H]5CCCO5)nn4C)ccc3[nH]2)n1] | 1-methyl-5-[2-(3-methyl-1,2,4-oxadiazol-5-yl)-1H-indol-5-yl]-N-[(2S)-tetrahydrofuran-2-ylmethyl]-1H-pyrazole-3-carboxamide |

TABLE I-continued

| | |
|---|---|
| 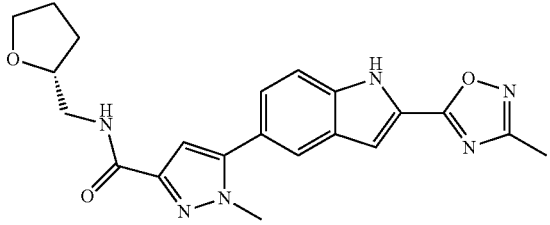 | 1-methyl-5-[2-(3-methyl-1,2,4-oxadiazol-5-yl)-1H-indol-5-yl]-N-[(2R)-tetrahydrofuran-2-ylmethyl]-1H-pyrazole-3-carboxamide |
| 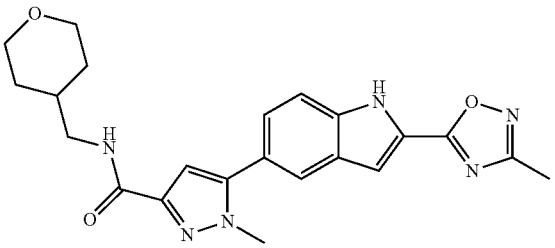 [SMILES: Cc1noc(-c2cc3cc(-c4cc(C(=O)NCC5CCOCC5)nn4C)ccc3[nH]2)n1] | 1-methyl-5-[2-(3-methyl-1,2,4-oxadiazol-5-yl)-1H-indol-5-yl]-N-(tetrahydro-2H-pyran-4-ylmethyl)-1H-pyrazole-3-carboxamide |
| 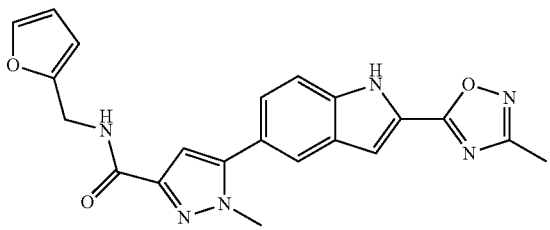 [SMILES: Cc1noc(-c2cc3cc(-c4cc(C(=O)NCc5ccco5)nn4C)ccc3[nH]2)n1] | N-(furan-2-ylmethyl)-1-methyl-5-[2-(3-methyl-1,2,4-oxadiazol-5-yl)-1H-indol-5-yl]-1H-pyrazole-3-carboxamide |
| 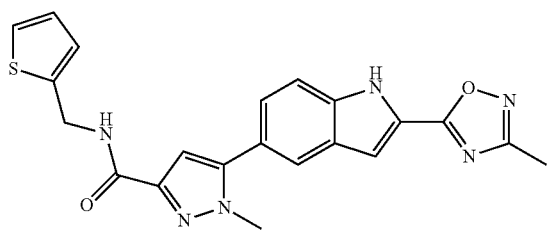 [SMILES: Cc1noc(-c2cc3cc(-c4cc(C(=O)NCc5cccs5)nn4C)ccc3[nH]2)n1] | 1-methyl-5-[2-(3-methyl-1,2,4-oxadiazol-5-yl)-1H-indol-5-yl]-N-(thiophen-2-ylmethyl)-1H-pyrazole-3-carboxamide |
| 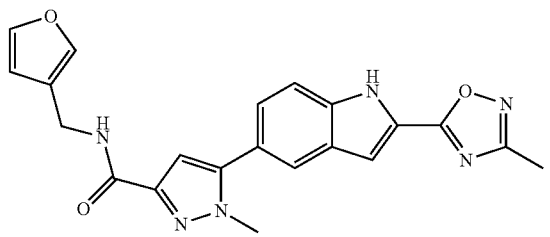 [SMILES: Cc1noc(-c2cc3cc(-c4cc(C(=O)NCc5ccoc5)nn4C)ccc3[nH]2)n1] | N-(furan-3-ylmethyl)-1-methyl-5-[2-(3-methyl-1,2,4-oxadiazol-5-yl)-1H-indol-5-yl]-1H-pyrazole-3-carboxamide |
| 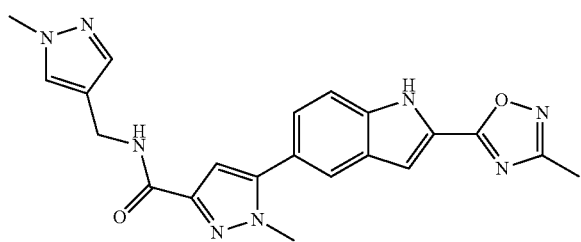 | 1-methyl-5-[2-(3-methyl-1,2,4-oxadiazol-5-yl)-1H-indol-5-yl]-N-[(1-methyl-1H-pyrazol-4-yl)methyl]-1H-pyrazole-3-carboxamide |

TABLE I-continued

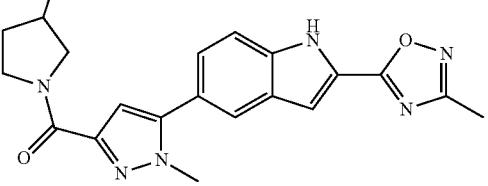

{1-methyl-5-[2-(3-methyl-1,2,4-oxadiazol-5-yl)-1H-indol-5-yl]-1H-pyrazol-3-yl}[3-(pyridin-4-yl)pyrrolidin-1-yl]methanone

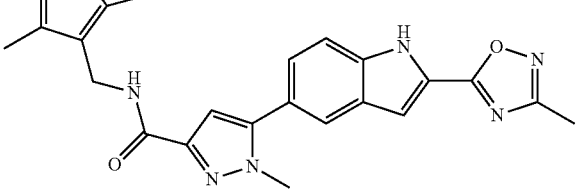

1-methyl-5-[2-(3-methyl-1,2,4-oxadiazol-5-yl)-1H-indol-5-yl]-N-[(1,3,5-trimethyl-1H-pyrazol-4-yl)methyl]-1H-pyrazole-3-carboxamide

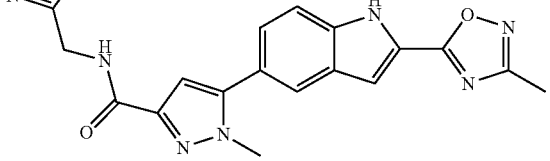

1-methyl-N-[(5-methylisoxazol-3-yl)methyl]-5-[2-(3-methyl-1,2,4-oxadiazol-5-yl)-1H-indol-5-yl]-1H-pyrazole-3-carboxamide

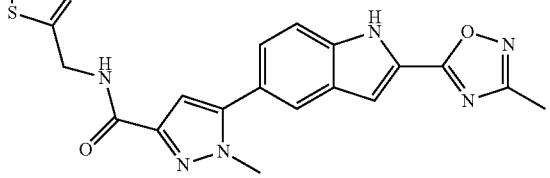

1-methyl-5-[2-(3-methyl-1,2,4-oxadiazol-5-yl)-1H-indol-5-yl]-N-(1,3-thiazol-2-ylmethyl)-1H-pyrazole-3-carboxamide

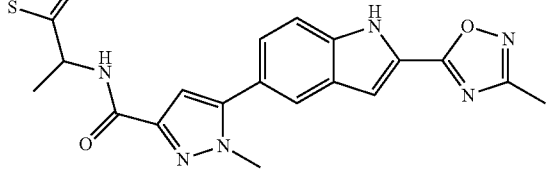

1-methyl-5-[2-(3-methyl-1,2,4-oxadiazol-5-yl)-1H-inol-5-yl]-N-[1-(thiophen-2-yl)ethyl]-1H-pyrazole-3-carboxamide

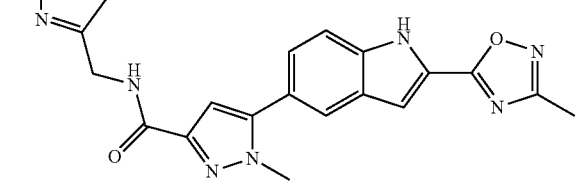

1-methyl-5-[2-(3-methyl-1,2,4-oxadiazol-5-yl)-1H-indol-5-yl]-N-[(1-methyl-1H-pyrazol-3-yl)methyl]-1H-pyrazole-3-carboxamide TABLE I-continued

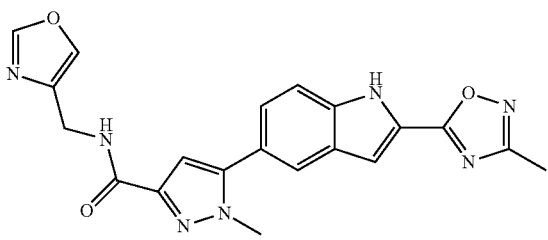 [SMILES: Cc1noc(-c2cc3cc(-c4cc(C(=O)NCc5cocn5)nn4C)ccc3[nH]2)n1]

1-methyl-5-[2-(3-methyl-1,2,4-oxadiazol-5-yl)-1H-indol-5-yl]-N-(1,3-oxadiazol-4-ylmethyl)-1H-pyrazole-3-carboxamide

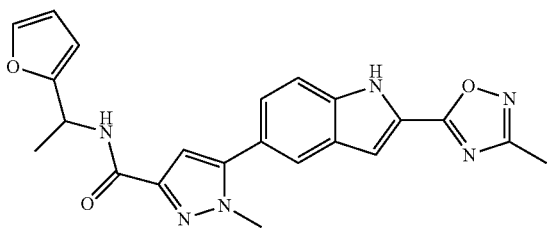 [SMILES: Cc1noc(-c2cc3cc(-c4cc(C(=O)NC(C)c5ccco5)nn4C)ccc3[nH]2)n1]

N-[1-(furan-2-yl)ethyl]-1-methyl-5-[2-(3-methyl-1,2,4-oxadiazol-5-yl)-1H-indol-5-yl]-1H-pyrazole-3-carboxamide

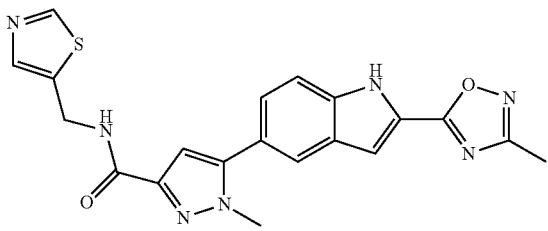 [SMILES: Cc1noc(-c2cc3cc(-c4cc(C(=O)NCc5cncs5)nn4C)ccc3[nH]2)n1]

1-methyl-5-[2-(3-methyl-1,2,4-oxadiazol-5-yl)-1H-indol-5-yl]-N-(1,3-thiazol-5-ylmethyl)-1H-pyrazole-3-carboxamide

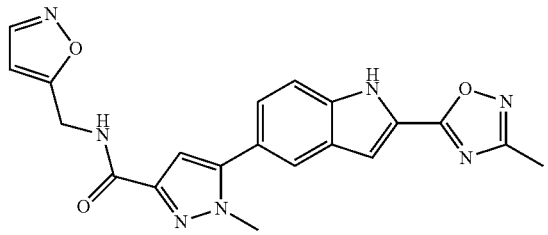 [SMILES: Cc1noc(-c2cc3cc(-c4cc(C(=O)NCc5ccno5)nn4C)ccc3[nH]2)n1]

N-(isoxazol-5-ylmethyl)-1-methyl-5-[2-(3-methyl-1,2,4-oxadiazol-5-yl)-1H-indol-5-yl]-1H-pyrazole-3-carboxamide

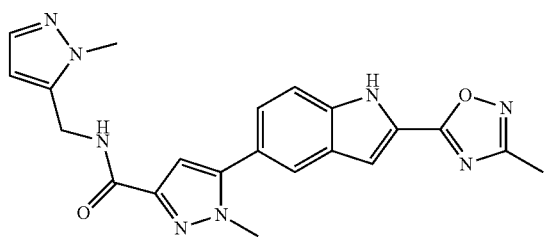 [SMILES: Cc1noc(-c2cc3cc(-c4cc(C(=O)NCc5ccnn5C)nn4C)ccc3[nH]2)n1]

1-methyl-5-[2-(3-methyl-1,2,4-oxadiazol-5-yl)-1H-indol-5-yl]-N-[(1-methyl-1H-pyrazol-5-yl)methyl]-1H-pyrazole-3-carboxamide

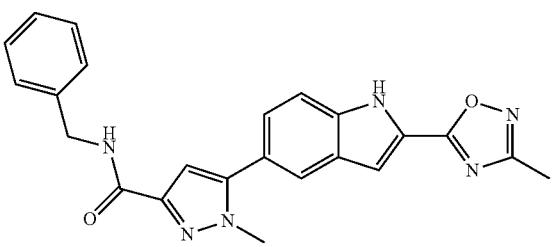 [SMILES: Cc1noc(-c2cc3cc(-c4cc(C(=O)NCc5ccccc5)nn4C)ccc3[nH]2)n1]

N-benzyl-1-methyl-5-[2-(3-methyl-1,2,4-oxadiazol-5-yl)-1H-indol-5-yl]-1H-pyrazole-3-carboxamide TABLE I-continued

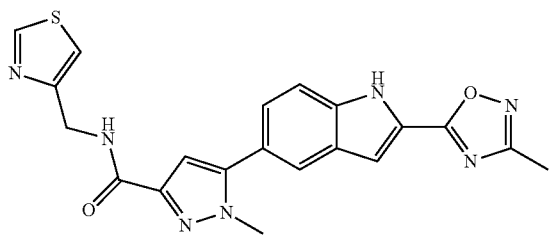 [SMILES: Cc1noc(-c2cc3cc(-c4cc(C(=O)NCc5cscn5)nn4C)ccc3[nH]2)n1]

1-methyl-5-[2-(3-methyl-1,2,4-oxadiazol-5-yl)-1H-indol-5-yl]-N-(1,3-thiazol-4-ylmethyl)-1H-pyrazole-3-carboxamide

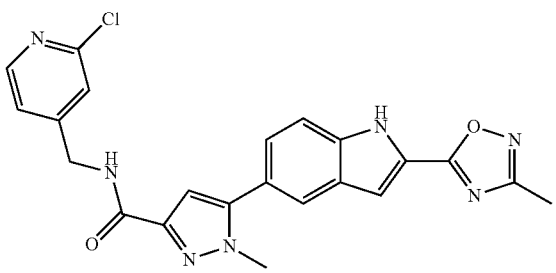 [SMILES: Cc1noc(-c2cc3cc(-c4cc(C(=O)NCc5ccnc(Cl)c5)nn4C)ccc3[nH]2)n1]

N-[(2-chloropyridin-4-yl)methyl]-1-methyl-5-[2-(3-methyl-1,2,4-oxadiazol-5-yl)-1H-indol-5-yl]-1H-pyrazole-3-carboxamide

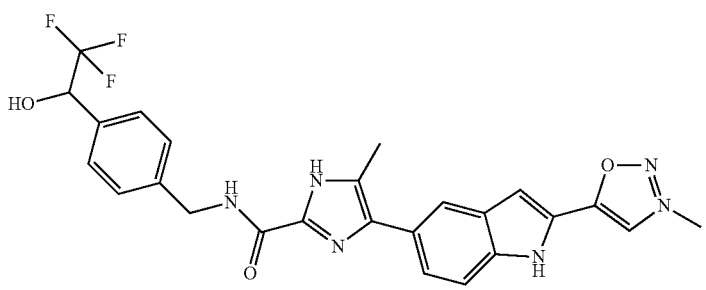

5-Methyl-4-[2-(3-methyl-1,2,4-oxadiazol-5-yl)-1H-indol-5-yl]-1H-imidazole-2-carboxylic acid 4-(2,2,2-trifluoro-1-hydroxy-ethyl)-benzylamide

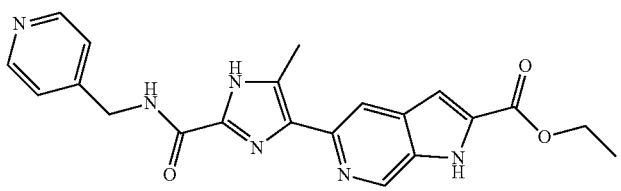 [SMILES: CCOC(=O)c1cc2cc(-c3nc(C(=O)NCc4ccncc4)[nH]c3C)ncc2[nH]1]

5-{5-Methyl-2-[(pyridin-4-ylmethyl)-carbamoyl]-1H-imidazol-4-yl}-1H-pyrrolo[2,3-c]pyridine-2-carboxylic acid ethyl ester

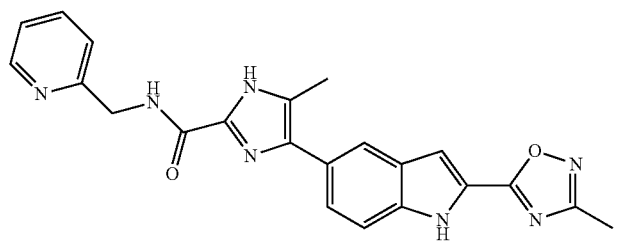 [SMILES: Cc1noc(-c2cc3cc(-c4nc(C(=O)NCc5ccccn5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid (pyridin-2-ylmethyl)-amide

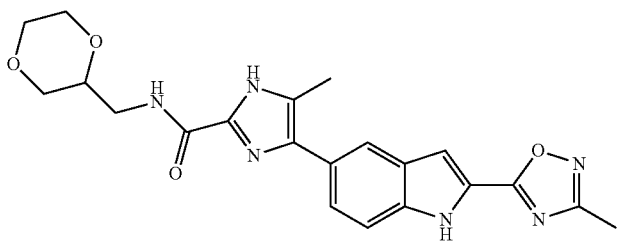 [SMILES: Cc1noc(-c2cc3cc(-c4nc(C(=O)NCC5COCCO5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid (1,4-dioxinan-2-ylmethyl)-amide TABLE I-continued

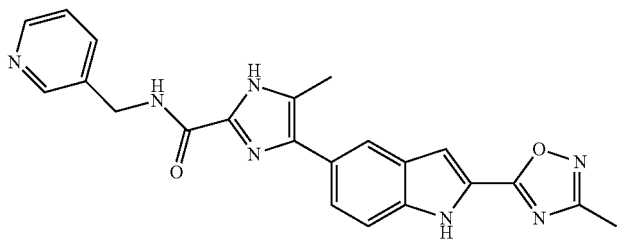 [SMILES: Cc1noc(-c2cc3cc(-c4nc(C(=O)NCc5cccnc5)[nH]c4C)ccc3[nH]2)n1]

5-Methyl-4-[2-(3-methyl-1,2,4-oxadiazol-5-yl)-1H-indol-5-yl]-1H-imidazole-2-carboxlic acid (pyridin-3-ylmethyl)-amide

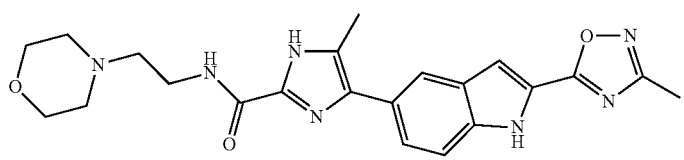 [SMILES: Cc1noc(-c2cc3cc(-c4nc(C(=O)NCCN5CCOCC5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid (2-morpholin-4-yl-ethyl)-amide

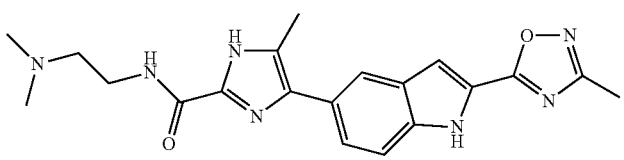

5-Methyl-4-[2-(3-methyl-1,2,4-oxadiazol-5-yl)-1H-indol-5-yl]-1H-imidazole-2-carboxylic acid (2-dimethylamino-ethyl)-amide

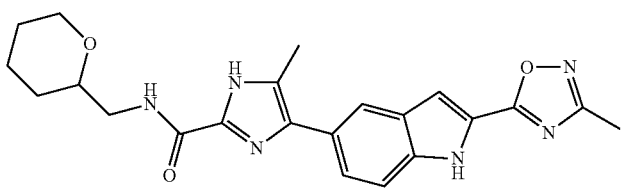 [SMILES: Cc1noc(-c2cc3cc(-c4nc(C(=O)NCC5CCCCO5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid (tetrahydro-pyran-2-ylmethyl)-amide

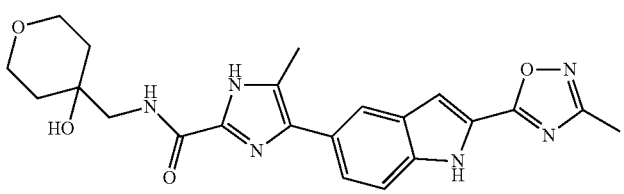 [SMILES: Cc1noc(-c2cc3cc(-c4nc(C(=O)NCC5(O)CCOCC5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid (4-hydroxy-tetrahydro-pyran-4-ylmethyl)-amide

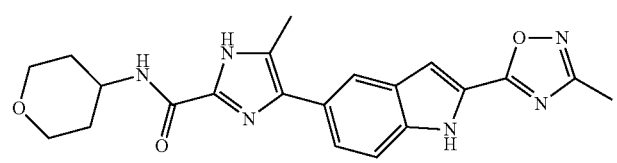 [SMILES: Cc1noc(-c2cc3cc(-c4nc(C(=O)NC5CCOCC5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid (tetrahydro-pyran-4-yl)-amide

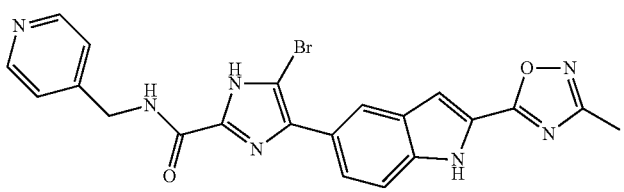 [SMILES: Cc1noc(-c2cc3cc(-c4nc(C(=O)NCc5ccncc5)[nH]c4Br)ccc3[nH]2)n1]

5-Bromo-4-[2-(3-methyl-1,2,4-oxadiazol-5-yl)-1H-indol-5-yl]-1H-imidazole-2-carboxylic acid (pyridin-4-ylmethyl)-amide

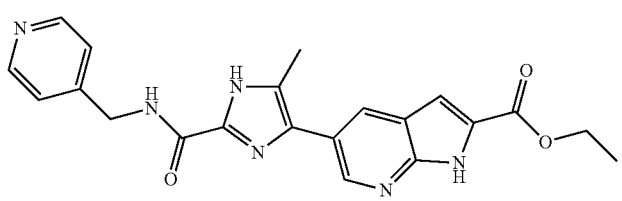 [SMILES: CCOC(=O)c1cc2cc(-c3nc(C(=O)NCc4ccncc4)[nH]c3C)cnc2[nH]1]

5-{5-Methyl-2-[(pyridin-4-ylmethyl)-carbamoyl]-3H-imidazol-4-yl}-1H-pyrrolo[2,3-b]pyridine-2-carboxylic acid ethyl ester TABLE I-continued

| | |
|---|---|
| 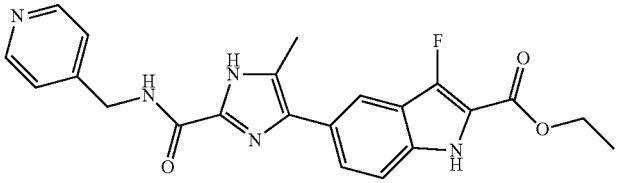 [SMILES: CCOC(=O)c1[nH]c2ccc(-c3nc(C(=O)NCc4ccncc4)[nH]c3C)cc2c1F] | 3-Fluoro-5-{5-methyl-2-[(pyridin-4-ylmethyl)-carbamoyl]-3H-imidazol-4-yl}-1H-indole-2-carboxylic acid ethyl ester |
| 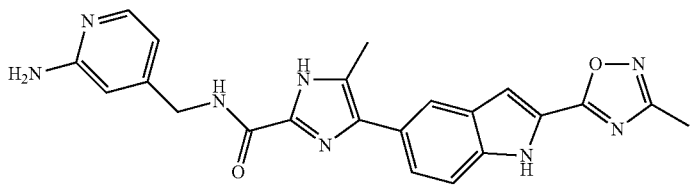 [SMILES: Cc1noc(-c2cc3cc(-c4nc(C(=O)NCc5ccnc(N)c5)[nH]c4C)ccc3[nH]2)n1] | 4-Methyl-5-[2-(3-methyl-[1,2,4]oxadiazol-5-yl)-1H-indol-5-yl]-1H-imidazole-2-carboxylic acid (2-amino-pyridin-4-ylmethyl)-amide |
| 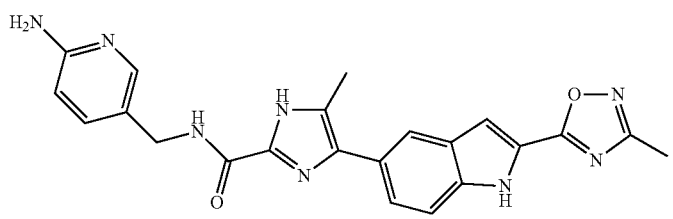 [SMILES: Cc1noc(-c2cc3cc(-c4nc(C(=O)NCc5ccc(N)nc5)[nH]c4C)ccc3[nH]2)n1] | 4-Methyl-5-[2-(3-methyl-[1,2,4]oxadiazol-5-yl)-1H-indol-5-yl]-1H-imidazole-2-carboxylic acid (6-amino-pyridin-3-ylmethyl)-amide |
| 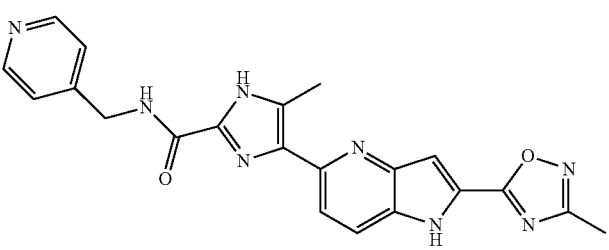 [SMILES: Cc1noc(-c2cc3nc(-c4nc(C(=O)NCc5ccncc5)[nH]c4C)ccc3[nH]2)n1] | 5-Methyl-4-[2-(3-methyl-1,2,4-oxadiazol-5-yl)-1H-pyrrolo[3,2-b]pyridin-5-yl]-1H-imidazole-2-carboxylic acid (pyridin-4-ylmethyl)-amide |
| 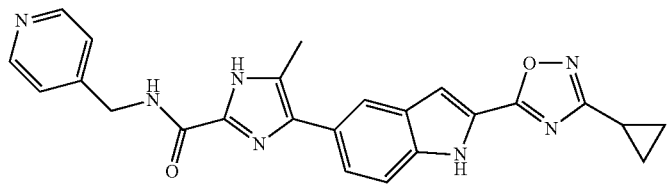 [SMILES: Cc1[nH]c(C(=O)NCc2ccncc2)nc1-c1ccc2[nH]c(-c3nc(C4CC4)no3)cc2c1] | 4-[2-(3-Cyclopropyl-1,2,4-oxadiazol-5-yl)-1H-indol-5-yl]-5-methyl-1H-imidazole-2-carboxylic acid (pyridin-4-ylmethyl)-amide |
| 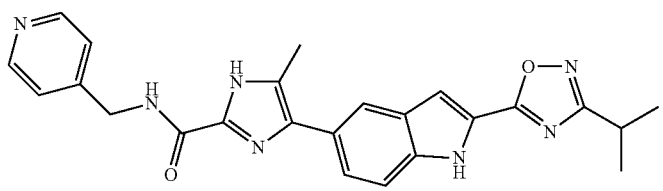 [SMILES: Cc1[nH]c(C(=O)NCc2ccncc2)nc1-c1ccc2[nH]c(-c3nc(C(C)C)no3)cc2c1] | 4-[2-(3-Isopropyl-1,2,4-oxadiazol-5-yl)-1H-indol-5-yl]-5-methyl-1H-imidazole-2-carboxylic acid (pyridin-4-ylmethyl)-amide |
| 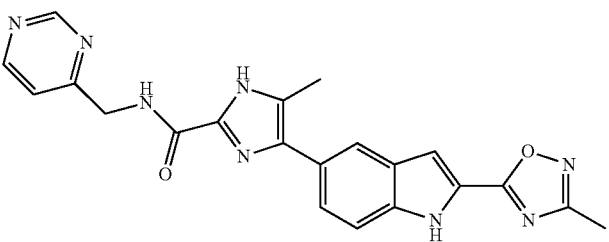 [SMILES: Cc1noc(-c2cc3cc(-c4nc(C(=O)NCc5ccncn5)[nH]c4C)ccc3[nH]2)n1] | 5-Methyl-4-[2-(3-methyl-1,2,4-oxadiazol-5-yl)-1H-indol-5-yl]-1-H-imidazole-2-carboxylic acid (pyrimidin-4-ylmethyl)-amide |

TABLE I-continued

| Structure | Name |
|---|---|
| (structure) | 5-Methyl-4-[2-(3-methyl-1,2,4-oxadiazol-5-yl)-1H-indol-5-yl]-1H-imidazole-2-carboxylic acid (pyridazin-4-ylmethyl)-amide |
| (structure) | 5-Methyl-4-[2-(3-methyl-1,2,4-oxadiazol-5-yl)-1H-indol-5-yl]-1H-imidazole-2-carboxylic acid (5-methyl-1,2,4-oxadiazol-3-ylmethyl)-amide |
| (structure) | 5-Methyl-4-[2-(3-methyl-1,2,4-oxadiazol-5-yl)-1H-indol-5-yl]-1H-imidazole-2-carboxylic acid (6,7-dihydro-5H-pyrrolo[2,1-c]-1,2,4-triazol-3-ylmethyl)-amide |
| (structure) | 5-Methyl-4-[2-(3-methyl-1,2,4-oxadiazol-5-yl)-1H-indol-5-yl]-1H-imidazole-2-carboxylic acid (4H-1,2,4-triazol-3-ylmethyl)-amide |
| (structure) | 5-Methyl-4-[2-(3-methyl-1,2,4-oxadiazol-5-yl)-1H-indol-5-yl]-1H-imidazole-2-carboxylic acid (5-methyl-4H-1,2,4-triazol-3-ylmethyl)-amide | or a pharmaceutically acceptable salt thereof.

The following are preferred MMP-13 inhibitors:

TABLE II

| Name | MMP13 IC50 nM |
|---|---|
| 4-{[({1-methyl-5-[2-(3-methyl-1,2,4-oxadiazol-5-yl)-1H-indol-5-yl]-1H-pyrazol-3-yl}carbonyl)amino]methyl}benzoic acid | 0.2 |
| 4-{[({4-[2-(3-methyl-1,2,4-oxadiazol-5-yl)-1H-indol-5-yl]pyridin-2-yl}carbonyl)amino]methyl}benzoic acid | 0.2 |
| 4-{[({5-methyl-4-[2-(3-methyl-1,2,4-oxadiazol-5-yl)-1H-indol-5-yl]pyridin-2-yl}carbonyl)amino]methyl}benzoic acid | 0.2 |
| 4-{[({5-methyl-4-[2-(3-methyl-1,2,4-oxadiazol-5-yl)-1H-indol-5-yl]-1H-imidazol-2-yl}carbonyl)amino]methyl}benzoic acid | 0.2 |
| 5-methyl-4-[2-(3-methyl-1,2,4-oxadiazol-5-yl)-1H-indol-5-yl]-N-[(6-oxo-1,6-dihydropyridin-3-yl)methyl]-1H-imidazole-2-carboxamide | 0.2 |
| 5-methyl-4-[2-(3-methyl-1,2,4-oxadiazol-5-yl)-1H-indol-5-yl]-N-[(1-methyl-1H-pyrazol-4-yl)methyl]-1H-imidazole-2-carboxamide | 0.4 |
| 5-methyl-4-[2-(3-methyl-1,2,4-oxadiazol-5-yl)-1H-indol-5-yl]-N-(pyridin-4-ylmethyl)-1H-imidazole-2-carboxamide | 0.4 |

TABLE II-continued

| Name | MMP13 IC50 nM |
| --- | --- |
| 5-methyl-4-[2-(3-methyl-1,2,4-oxadiazol-5-yl)-1H-indol-5-yl]-N-(pyrimidin-4-ylmethyl)-1H-imidazole-2-carboxamide | 0.6 |
| 5-methyl-4-[2-(3-methyl-1,2,4-oxadiazol-5-yl)-1H-indol-5-yl]-N-(pyridin-3-ylmethyl)-1H-imidazole-2-carboxamide | 0.6 |
| N-(isoxazol-5-ylmethyl)-5-methyl-4-[2-(3-methyl-1,2,4-oxadiazol-5-yl)-1H-indol-5-yl]-1H-imidazole-2-carboxamide | 0.7 |
| 4-{[({4-[2-(ethoxycarbonyl)-1H-indol-5-yl]pyridin-2-yl}carbonyl)amino]methyl}benzoic acid | 0.7 |
| 4-[({[1-methyl-5-(2-pyridin-4-yl-1H-indol-5-yl)-1H-pyrazol-3-yl]carbonyl}amino)methyl]benzoic acid | 0.8 |
| 4-[({[1-methyl-5-(2-pyrimidin-4-yl-1H-indol-5-yl)-1H-pyrazol-3-yl]carbonyl}amino)methyl]benzoic acid | 0.8 |
| 4-{[({5-[2-(ethoxycarbonyl)-1H-indol-5-yl]-1-methyl-1H-pyrazol-3-yl}carbonyl)amino]methyl}benzoic acid | 0.8 |
| 5-methyl-N-[(5-methylisoxazol-3-yl)methyl]-4-[2-(3-methyl-1,2,4-oxadiazol-5-yl)-1H-indol-5-yl]-1H-imidazole-2-carboxamide | 0.9 |
| 5-methyl-4-[2-(3-methyl-1,2,4-oxadiazol-5-yl)-1H-indol-5-yl]-N-[(5-methylisoxazol-3-yl)methyl]-1H-imidazole-2-carboxamide | 0.9 |
| N-[(2-cyanopyridin-4-yl)methyl]-5-methyl-4-[2-(3-methyl-1,2,4-oxadiazol-5-yl)-1H-indol-5-yl]-1H-imidazole-2-carboxamide | 0.95 |
| 5-methyl-4-[2-(3-methyl-1,2,4-oxadiazol-5-yl)-1H-indol-5-yl]-N-(tetrahydro-2H-pyran-4-ylmethyl)-1H-imidazole-2-carboxamide | 1.1 |
| 5-methyl-4-[2-(3-methyl-1,2,4-oxadiazol-5-yl)-1H-indol-5-yl]-N-(pyridazin-4-ylmethyl)-1H-imidazole-2-carboxamide | 1.2 |
| N-[(2-aminopyridin-4-yl)methyl]-4-methyl-5-[2-(3-methyl-1,2,4-oxadiazol-5-yl)-1H-indol-5-yl]-1H-imidazole-2-carboxamide | 1.3 |
| 4-{[({1-methyl-5-[2-(1-methyl-1H-pyrazol-4-yl)-1H-indol-5-yl]-1H-pyrazol-3-yl}carbonyl)amino]methyl}benzoic acid | 1.5 |
| 4-[({[1-methyl-5-(2-pyrimidin-2-yl-1H-indol-5-yl)-1H-pyrazol-3-yl]carbonyl}amino)methyl]benzoic acid | 1.6 |
| N-(1,4-dioxan-2-ylmethyl)-5-methyl-4-[2-(3-methyl-1,2,4-oxadiazol-5-yl)-1H-indol-5-yl]-1H-imidazole-2-carboxamide | 1.9 |
| N-(4-cyanobenzyl)-5-methyl-4-[2-(3-methyl-1,2,4-oxadiazol-5-yl)-1H-indol-5-yl]-1H-imidazole-2-carboxamide | 2 |
| 5-methyl-4-[2-(3-methyl-1,2,4-oxadiazol-5-yl)-1H-indol-5-yl]-N-(2-thienylmethyl)-1H-imidazole-2-carboxamide | 2 |
| ethyl 5-{4-methyl-2-[(pyridin-4-ylmethyl)carbamoyl]-1H-imidazol-5-yl}-1H-indole-2-carboxylate | 2 |
| N-benzyl-5-methyl-4-[2-(3-methyl-1,2,4-oxadiazol-5-yl)-1H-indol-5-yl]-1H-imidazole-2-carboxamide | 2 |
| 5-methyl-4-[2-(3-methyl-1,2,4-oxadiazol-5-yl)-1H-indol-5-yl]-N-(1,3-thiazol-2-ylmethyl)-1H-imidazole-2-carboxamide | 2 |
| N-[(6-aminopyridin-3-yl)methyl]-4-methyl-5-[2-(3-methyl-1,2,4-oxadiazol-5-yl)-1H-indol-5-yl]-1H-imidazole-2-carboxamide | 2 |
| 4-{[({5-[2-(2-fluoropyridin-4-yl)-1H-indol-5-yl]-1-methyl-1H-pyrazol-3-yl}carbonyl)amino]methyl}benzoic acid | 2 |
| 5-methyl-4-[2-(3-methyl-1,2,4-oxadiazol-5-yl)-1H-indol-5-yl]-N-(pyridin-2-ylmethyl)-1H-imidazole-2-carboxamide | 3 |
| (4-{[({5-[2-(ethoxycarbonyl)-1H-indol-5-yl]-1-methyl-1H-pyrazol-3-yl}carbonyl)amino]methyl}phenyl)acetic acid | 3 |
| 5-methyl-4-[2-(3-methyl-1,2,4-oxadiazol-5-yl)-1H-indol-5-yl]-N-(tetrahydrofuran-2-ylmethyl)-1H-imidazole-2-carboxamide | 3 |
| 4-[({[1-methyl-5-(2-pyridin-3-yl-1H-indol-5-yl)-1H-pyrazol-3-yl]carbonyl}amino)methyl]benzoic acid | 3 |
| N-(3-furylmethyl)-5-methyl-4-[2-(3-methyl-1,2,4-oxadiazol-5-yl)-1H-indol-5-yl]-1H-imidazole-2-carboxamide | 3 |
| 1-methyl-5-[2-(3-methyl-1,2,4-oxadiazol-5-yl)-1H-indol-5-yl]-N-(pyridin-4-ylmethyl)-1H-pyrazole-3-carboxamide | 4 |
| N-(6,7-dihydro-5H-pyrrolo[2,1-c][1,2,4]triazol-3-ylmethyl)-5-methyl-4-[2-(3-methyl-1,2,4-oxadiazol-5-yl)-1H-indol-5-yl]-1H-imidazole-2-carboxamide | 4 |
| 5-methyl-4-[2-(3-methyl-1,2,4-oxadiazol-5-yl)-1H-indol-5-yl]-N-[(2S)-tetrahydrofuran-2-ylmethyl]-1H-imidazole-2-carboxamide | 4 |
| N-[(2-chloropyridin-4-yl)methyl]-1-methyl-5-[2-(3-methyl-1,2,4-oxadiazol-5-yl)-1H-indol-5-yl]-1H-pyrazole-3-carboxamide | 4 |
| 5-methyl-4-[2-(3-methyl-1,2,4-oxadiazol-5-yl)-1H-indol-5-yl]-N-(2-morpholin-4-ylethyl)-1H-imidazole-2-carboxamide | 5 |
| 5-methyl-4-[2-(3-methyl-1,2,4-oxadiazol-5-yl)-1H-indol-5-yl]-N-[(2R)-tetrahydrofuran-2-ylmethyl]-1H-imidazole-2-carboxamide | 5 |
| 5-methyl-4-[2-(3-methyl-1,2,4-oxadiazol-5-yl)-1H-indol-5-yl]-N-(tetrahydro-2H-pyran-2-ylmethyl)-1H-imidazole-2-carboxamide | 5 |
| 4-[({[1-methyl-5-(2-pyrimidin-5-yl-1H-indol-5-yl)-1H-pyrazol-3-yl]carbonyl}amino)methyl]benzoic acid | 5 |
| N-(4-fluorobenzyl)-5-methyl-4-[2-(3-methyl-1,2,4-oxadiazol-5-yl)-1H-indol-5-yl]-1H-imidazole-2-carboxamide | 6 |
| 4-[2-(3-cyclopropyl-1,2,4-oxadiazol-5-yl)-1H-indol-5-yl]-5-methyl-N-(pyridin-4-ylmethyl)-1H-imidazole-2-carboxamide | 6 |
| N-[(4-hydroxytetrahydro-2H-pyran-4-yl)methyl]-5-methyl-4-[2-(3-methyl-1,2,4-oxadiazol-5-yl)-1H-indol-5-yl]-1H-imidazole-2-carboxamide | 6 |
| 5-methyl-4-[2-(3-methyl-1,2,4-oxadiazol-5-yl)-1H-indol-5-yl]-N-(4H-1,2,4-triazol-3-ylmethyl)-1H-imidazole-2-carboxamide | 6 |
| ethyl 3-fluoro-5-{5-methyl-2-[(pyridin-4-ylmethyl)carbamoyl]-1H-imidazol-4-yl}-1H-indole-2-carboxylate | 7 |
| ethyl 5-{5-methyl-2-[(pyridin-4-ylmethyl)carbamoyl]-1H-imidazol-4-yl}-1H-pyrrolo[2,3-c]pyridine-2-carboxylate | 7 |
| N-(cyclopropylmethyl)-5-methyl-4-[2-(3-methyl-1,2,4-oxadiazol-5-yl)-1H-indol-5-yl]-1H-imidazole-2-carboxamide | 8 |
| 1-methyl-5-[2-(3-methyl-1,2,4-oxadiazol-5-yl)-1H-indol-5-yl]-N-[(1-methyl-1H-pyrazol-4-yl)methyl]-1H-pyrazole-3-carboxamide | 10 |
| 1-methyl-5-[2-(3-methyl-1,2,4-oxadiazol-5-yl)-1H-indol-5-yl]-N-(1,3-thiazol-5-ylmethyl)-1H-pyrazole-3-carboxamide | 10 |
| N-(4-cyanobenzyl)-1-methyl-5-[2-(3-methyl-1,2,4-oxadiazol-5-yl)-1H-indol-5-yl]-1H-pyrazole-3-carboxamide | 10 |
| 5-methyl-4-[2-(3-methyl-1,2,4-oxadiazol-5-yl)-1H-indol-5-yl]-1H-imidazole-2-carboxamide | 10 |
| N-ethyl-5-methyl-4-[2-(3-methyl-1,2,4-oxadiazol-5-yl)-1H-indol-5-yl]-1H-imidazole-2-carboxamide | 10 |
| 4-[2-(3-methyl-1,2,4-oxadiazol-5-yl)-1H-indol-5-yl]-N-(pyridin-4-ylmethyl)pyridine-2-carboxamide | 12 |
| 5-methyl-4-[2-(3-methyl-1,2,4-oxadiazol-5-yl)-1H-indol-5-yl]-N-(pyridin-4-ylmethyl)pyridine-2-carboxamide | 14 |
| 5-methyl-4-[2-(3-methyl-1,2,4-oxadiazol-5-yl)-1H-indol-5-yl]-N-[1-(2-thienyl)ethyl]-1H-imidazole-2-carboxamide | 15 |
| 5-methyl-4-[2-(3-methyl-1,2,4-oxadiazol-5-yl)-1H-indol-5-yl]-N-[(5-methyl-4H-1,2,4-triazol-3-yl)methyl]-1H-imidazole-2-carboxamide | 17 |
| 4-[2-(3-isopropyl-1,2,4-oxadiazol-5-yl)-1H-indol-5-yl]-5-methyl-N-(pyridin-4-ylmethyl)-1H-imidazole-2-carboxamide | 18 |
| 5-methyl-4-[2-(3-methyl-1,2,4-oxadiazol-5-yl)-1H-indol-5-yl]-N-[4-(2,2,2-trifluoro-1-hydroxyethyl)benzyl]-1H-imidazole-2-carboxamide | 18 |
| N-(isoxazol-5-ylmethyl)-1-methyl-5-[2-(3-methyl-1,2,4-oxadiazol-5-yl)-1H-indol-5-yl]-1H-pyrazole-3-carboxamide | 19 |

TABLE II-continued

| Name | MMP13 IC50 nM |
|---|---|
| 5-methyl-4-[2-(3-methyl-1,2,4-oxadiazol-5-yl)-1H-pyrrolo[3,2-b]pyridin-5-yl]-N-(pyridin-4-ylmethyl)-1H-imidazole-2-carboxamide | 20 |
| 1-methyl-N-[(5-methylisoxazol-3-yl)methyl]-5-[2-(3-methyl-1,2,4-oxadiazol-5-yl)-1H-indol-5-yl]-1H-pyrazole-3-carboxamide | 24 |
| N-cyclopropyl-5-methyl-4-[2-(3-methyl-1,2,4-oxadiazol-5-yl)-1H-indol-5-yl]-1H-imidazole-2-carboxamide | 26 |
| N-benzyl-1-methyl-5-[2-(3-methyl-1,2,4-oxadiazol-5-yl)-1H-indol-5-yl]-1H-pyrazole-3-carboxamide | 26 |
| N-(4-fluorobenzyl)-1-methyl-5-[2-(3-methyl-1,2,4-oxadiazol-5-yl)-1H-indol-5-yl]-1H-pyrazole-3-carboxamide | 26 |
| N-(2-furylmethyl)-1-methyl-5-[2-(3-methyl-1,2,4-oxadiazol-5-yl)-1H-indol-5-yl]-1H-pyrazole-3-carboxamide | 27 |
| 4-{[({5-[2-(4-fluoro-3-methylphenyl)-1H-indol-5-yl]-1-methyl-1H-pyrazol-3-yl}carbonyl)amino]methyl}benzoic acid | 30 |
| ethyl 5-(2-{[(6-oxo-1,6-dihydropyridin-3-yl)methyl]carbamoyl}pyridin-4-yl)-1H-indole-2-carboxylate | 35 |
| 4-[2-(5-methyl-1,2,4-oxadiazol-3-yl)-1H-indol-5-yl]-N-(pyridin-4-ylmethyl)pyridine-2-carboxamide | 38 |
| ethyl 5-[2-(ethoxycarbonyl)-5-methyl-1H-imidazol-4-yl]-1H-indole-2-carboxylate | 39 |
| 4-{[({5-[2-(4,5-dihydro-1,3-oxazol-2-yl)-1H-indol-5-yl]-1-methyl-1H-pyrazol-3-yl}carbonyl)amino]methyl}benzoic acid | 43 |
| 1-methyl-5-[2-(3-methyl-1,2,4-oxadiazol-5-yl)-1H-indol-5-yl]-N-(2-thienylmethyl)-1H-pyrazole-3-carboxamide | 44 |
| N-(3-furylmethyl)-1-methyl-5-[2-(3-methyl-1,2,4-oxadiazol-5-yl)-1H-indol-5-yl]-1H-pyrazole-3-carboxamide | 45 |
| 4-{[({5-[2-(6-fluoropyridin-3-yl)-1H-indol-5-yl]-1-methyl-1H-pyrazol-3-yl}carbonyl)amino]methyl}benzoic acid | 48 |
| ethyl 5-{4-methyl-2-[(pyridin-4-ylmethyl)carbamoyl]-1H-imidazol-5-yl}-1H-pyrrolo[2,3-b]pyridine-2-carboxylate | 49 |
| ethyl 5-(3-{[4-(2-methoxy-2-oxoethyl)benzyl]carbamoyl}-1-methyl-1H-pyrazol-5-yl)-1H-indole-2-carboxylate | 51 |
| 4-[({[5-(2-cyano-1H-indol-5-yl)-1-methyl-1H-pyrazol-3-yl]carbonyl}amino)methyl]benzoic acid | 52 |
| 4-{[({5-[2-(2-fluoro-6-methylpyridin-4-yl)-1H-indol-5-yl]-1-methyl-1H-pyrazol-3-yl}carbonyl)amino]methyl}benzoic acid | 53 |
| 4-(2-pyridin-4-yl-1H-indol-5-yl)-N-(pyridin-4-ylmethyl)pyridine-2-carboxamide | 62 |
| 2-(3-methyl-1,2,4-oxadiazol-5-yl)-5-[5-methyl-2-(piperidin-1-ylcarbonyl)-1H-imidazol-4-yl]-1H-indole | 64 |
| 1-methyl-5-[2-(3-methyl-1,2,4-oxadiazol-5-yl)-1H-indol-5-yl]-N-(1,3-thiazol-2-ylmethyl)-1H-pyrazole-3-carboxamide | 73 |
| 4-{[({4-[1-(4-fluoro-3-methylbenzyl)-1H-pyrazol-4-yl]-5-methyl-1H-imidazol-2-yl}carbonyl)amino]methyl}benzoic acid | 88 |
| ethyl 5-{2-[(pyridin-4-ylmethyl)carbamoyl]pyridin-4-yl}-1H-indole-2-carboxylate | 94 |
| 1-methyl-5-[2-(3-methyl-1,2,4-oxadiazol-5-yl)-1H-indol-5-yl]-N-(1,3-thiazol-4-ylmethyl)-1H-pyrazole-3-carboxamide | 94 |
| ethyl 5-{5-methyl-2-[(pyridin-4-ylmethyl)carbamoyl]-1H-imidazol-4-yl}-1H-pyrrolo[3,2-b]pyridine-2-carboxylate | 95 |
| ethyl 5-{1-methyl-3-[(pyridin-4-ylmethyl)carbamoyl]-1H-pyrazol-5-yl}-1H-indole-2-carboxylate | 97 |
| 5-methyl-4-[2-(3-methyl-1,2,4-oxadiazol-5-yl)-1H-indol-5-yl]-N-(tetrahydro-2H-pyran-4-yl)-1H-imidazole-2-carboxamide | 106 |
| 2-(3-methyl-1,2,4-oxadiazol-5-yl)-5-[5-methyl-2-(pyrrolidin-1-ylcarbonyl)-1H-imidazol-4-yl]-1H-indole | 113 |
| 1-methyl-5-[2-(3-methyl-1,2,4-oxadiazol-5-yl)-1H-indol-5-yl]-N-(tetrahydro-2H-pyran-4-ylmethyl)-1H-pyrazole-3-carboxamide | 116 |
| ethyl 5-(1-methyl-3-{[(6-oxo-1,6-dihydropyridin-3-yl)methyl]carbamoyl}-1H-pyrazol-5-yl)-1H-indole-2-carboxylate | 125 |
| 1-methyl-5-[2-(3-methyl-1,2,4-oxadiazol-5-yl)-1H-indol-5-yl]-N-[(1-methyl-1H-pyrazol-5-yl)methyl]-1H-pyrazole-3-carboxamide | 125 |
| 4-{[({4-[1-(4-fluoro-3-methylbenzyl)-1H-pyrazol-4-yl]pyridin-2-yl}carbonyl)amino]methyl}benzoic acid | 130 |
| ethyl 5-{5-methyl-2-[(pyridin-4-ylmethyl)carbamoyl]pyridin-4-yl}-1H-indole-2-carboxylate | 155 |
| 1-methyl-5-[2-(3-methyl-1,2,4-oxadiazol-5-yl)-1H-indol-5-yl]-N-[(1-methyl-1H-pyrazol-3-yl)methyl]-1H-pyrazole-3-carboxamide | 185 |
| methyl 1-methyl-5-[2-(3-methyl-1,2,4-oxadiazol-5-yl)-1H-indol-5-yl]-1H-pyrazole-3-carboxylate | 190 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example azetidineyl, furanyl, pyranyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, tetrazolyl, pyrrolyl, pyrrolidinyl, pyrrolidinone, imidazolyl, thienyl, thiadiazolyl, oxadiazolyl, thiomorpholinyl, 1,1-dioxo-1$\lambda^6$-thiomorpholinyl, morpholinyl, pyridinyl, pyridinone, 1-oxy-pyridinyl, pyrimidinyl, pyridazinyl, pyrazinyl, triazinyl, pyrrolidinyl, piperidinyl, piperazinyl, purinyl, quinolinyl, dihydro-2H-quinolinyl, tetrahydroquinolinyl, isoquinolinyl, quinazolinyl, indazolyl, indolyl, indolinone, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" (or acyl) refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl (or any term using an "alk" or "alkyl" prefix), carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of the invention. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C1-C4 alkyl)4+ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention may be made using the general synthetic methods described below, which also constitute part of the invention.

General Synthetic Methods

The invention also provides processes for making compounds of formula (I). In all Schemes, unless specified otherwise, $R_1$, $R_2$, X and "Het" in the formulas below shall have the meaning of $R_1$, $R_2$, X and "Het" in Formula (I) of the invention described herein above, and in all schemes synthesis for formula (I) applies equally to formula (II).

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The appropriately substituted starting materials and intermediates used in the preparation of compounds of the invention are either commercially available or readily prepared by methods known in the literature to those skilled in the art, and are illustrated in the synthetic examples below.

Compounds of Formula (I) may be synthesized by methods outlined in Schemes 1, 2 or 3.

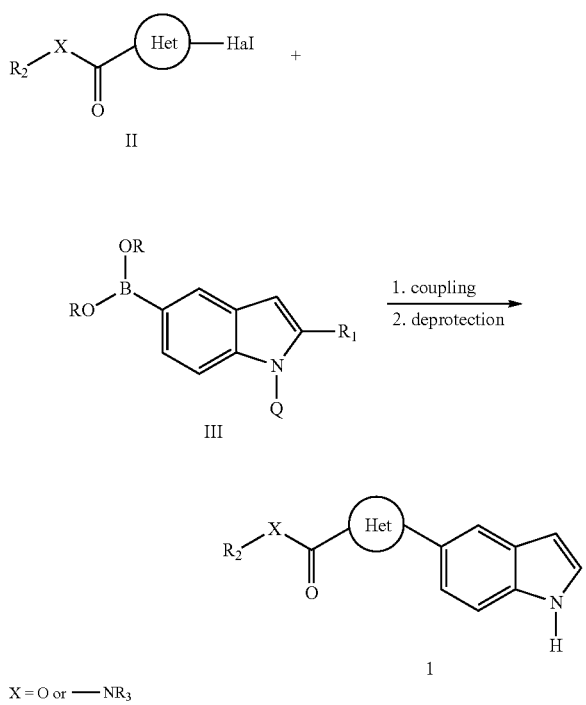

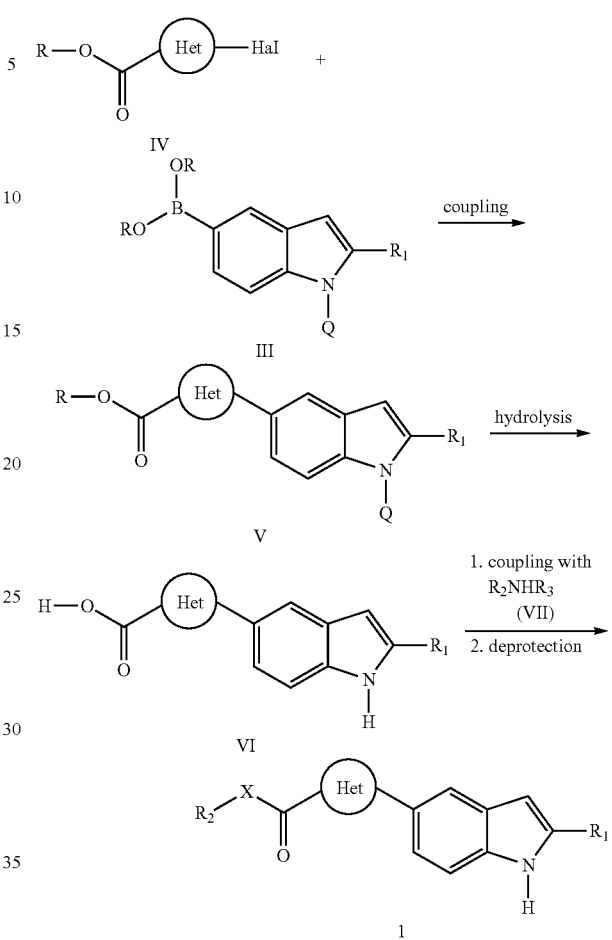

As illustrated in Scheme 1, Suzuki coupling of a halide of formula (II) with an indole-boronic acid/ester of formula (III), in a suitable solvent, in the presence of a suitable catalyst, provides the corresponding coupled product. Deprotection of the indole nitrogen of this coupled product under standard reaction conditions, provides a compound of Formula (I). Q is an amine protecting group such as BOC.

Compounds of Formula (I) may also be made by the method shown in Scheme 2.

As shown in Scheme 2, Suzuki coupling of a halide of formula (IV), wherein R is a lower alkyl group such as methyl or ethyl, with an indole-boronic acid/ester of formula (III), in a suitable solvent, in the presence of a suitable catalyst, provides the corresponding coupled product of formula (V). Hydrolysis of the ester group of compound of formula (V) under suitable reaction conditions provides the corresponding acid of formula (VI). Reaction of the acid of formula (VI) with an amine of formula (VII) under standard coupling conditions, followed by removal of the protecting group on the indole nitrogen, under standard conditions, provides a compound of formula (I). Q is an amine protecting group such as BOC.

Compounds of Formula (I) may also be made by the method shown in Scheme 3.

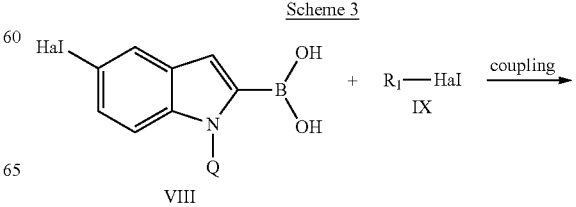

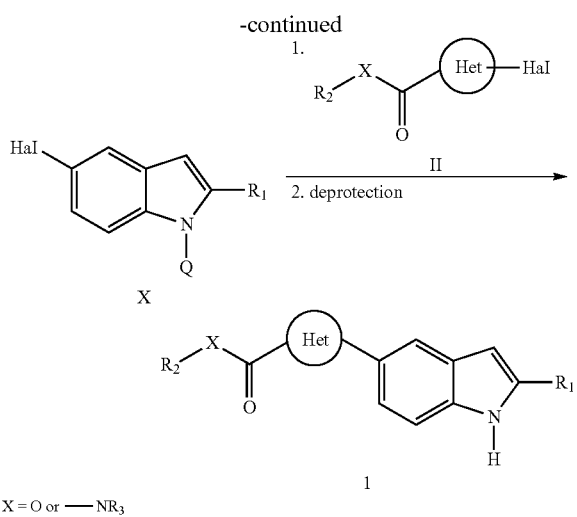

X = O or —NR₃

As illustrated in Scheme 3, coupling of an indole boronic acid of formula (VIII) (Hal=Br or I) with a halide of formula (IX), under standard Suzuki coupling conditions, provides the coupled product of formula (X). Coupling of the intermediate of formula (X) with a halide of formula (II), in a suitable solvent, in the presence of a suitable catalyst and a suitable base, provides the corresponding coupled product which upon deprotection, under standard conditions, provides a compound of formula (I). Q is an amine protecting group such as BOC.

Further modification of the initial product of Formula (I) by methods known in the art and illustrated in the Examples below, may be used to prepare additional compounds of this invention.

EXAMPLE 1

5-[5-(4-Methoxycarbonylmethyl-benzylcarbamoyl)-2-methyl-2H-pyrazol-3-yl]-1H-indole-2-carboxylic acid ethyl ester

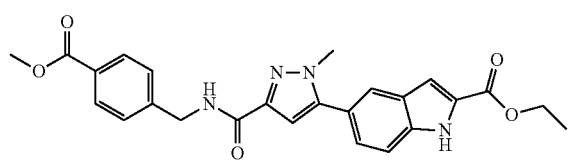 [SMILES: CCOC(=O)c1cc2cc(-c3cc(C(=O)NCc4ccc(C(=O)OC)cc4)nn3C)ccc2[nH]1]

Step 1.

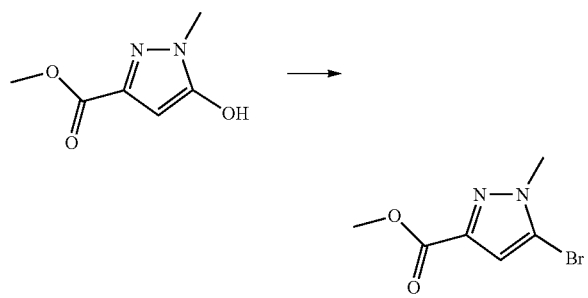

To a solution of methyl 5-hydroxy-1-methyl-3-pyrazole-carboxylate (Sucrow, W.; Auffenberg-Weddige, K.; Grosz, K. P.; Bredthauer, G.; Pickardt, J. Chemische Berichte 1983, 116(4), 1525-30., 10 g, 64 mmol), in acetonitrile (200 ml) is added POBr₃ (95 g, 322 mmol) and the resulting mixture is heated in a sealed flask at 80° C. for 15 hours. After 15 hours the reaction mixture is cooled to room temperature and added to a cooled (0° C.) solution of saturated aqueous sodium bicarbonate. After the addition, the product is extracted into ethyl acetate 3×. The combined organic layers are decolorized with charcoal, dried (anhydrous Na₂SO₄), filtered and evaporated in vacuo to give the product as a brown oil, that solidified upon standing 11.5 g, (72%), LC/MS ESI m/z (M+H)+= 220.2.

Step 2.

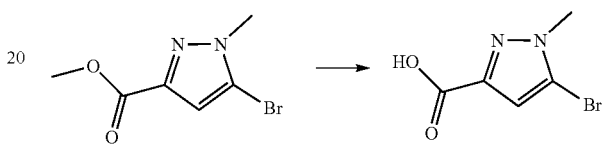

To a solution of 5-Bromo-1-methyl-1H-pyrazole-3-carboxylic acid methyl ester (5.6 g, 253 5 mmol) in 1,4 dioxane (41 ml) is added an aqueous solution of LiOH (32 ml, 4 N). The reaction mixture is stirred at room temperature for 1 hour, then water is added and the dioxane evaporated in vacuo. The remaining solution is washed with dichloromethane (2×), then acidified to pH 2 with HCl (12N). The product is extracted with ethyl acetate, dried (Na₂SO₄), filtered and evaporated in vacuo to give the title compound as a white solid 4.2 g, (80%), LC/MS ESI m/z (M+H)+=206.5.

Step 3.

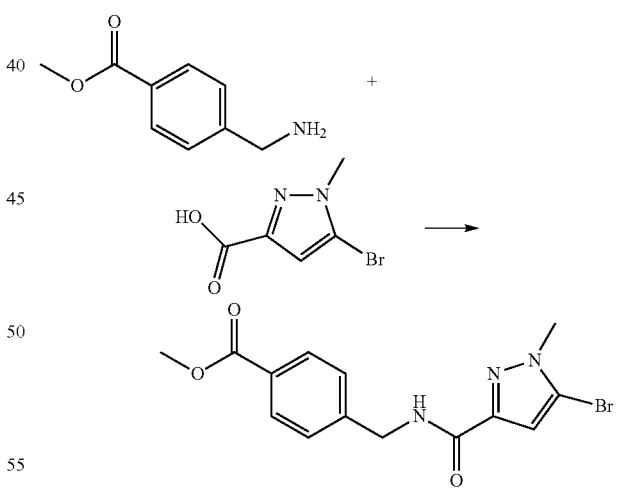

To a solution of 5-Bromo-1-methyl-1H-pyrazole-3-carboxylic acid (7.25 g 35 mmol) in N,N dimethylformamide (200 ml) is added O-(7-azabenzotriazol-1-yl)-N,N,N',N'-tetramethyluronium hexafluorophosphate (HATU) (15 g, 39 mmol). The reaction mixture is stirred for ½ hour. 4-Aminomethyl-benzoic acid methyl ester is added (7.8 g, 39 mmol), and the reaction stirred for 24 hours. The reaction mixture is poured into water and extracted into ethyl acetate. The combined organic layers are washed with water, brine, dried (Na₂SO₄), filtered and evaporated in vacuo to give an oil. The oil is taken up in ethyl acetate and washed with dilute acid (0.5 M HCl, 2×), saturated aqueous sodium bicarbonate (3×) and brine. The organic layer is dried (MgSO$_4$) filtered and evaporated in vacuo to give the title compound 12.1 g, (95%), LC/MS ESI m/z (M+H)+=353.7.

Step 4.

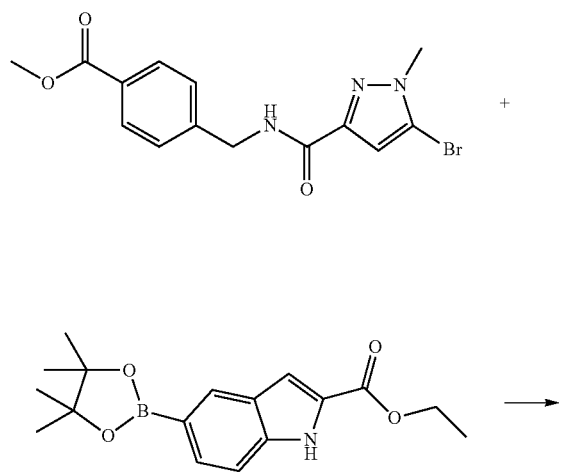

To a solution of 4-{[(5-Bromo-1-methyl-1H-pyrazole-3-carbonyl)-amino]-methyl}-benzoic acid methyl ester (30 mg, 0.08 mmol) in tetrahydrofuran (3 ml) is added tetrakis(triphenylphosphine)palladium (Pd(PPh$_3$)$_4$) (5 mg, 0.003 mmol) and 1H-Indole-2-carboxylic acid, 5-(4,4,5,5-tetramethyl-1,3,2-dioxaborolan-2-yl)-ethyl ester (28 mg, 0.09 mmol), followed by aqueous Na$_2$CO$_3$ (2M, 0.6 mL). The mixture is heated to reflux for 4 hours, and then quenched with water and extracted with ethyl acetate. The organic layer is dried over MgSO$_4$, concentrated in vacuo and purified on reverse phase HPLC to provide the title compound 38 mg, (77%), LC/MS ESI m/z (M+H)+=461.1.

EXAMPLE 2

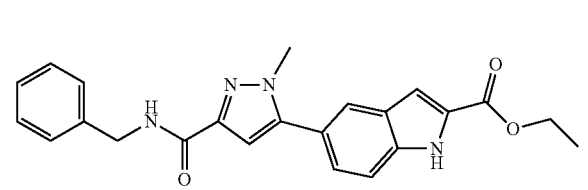 [SMILES: CCOC(=O)c1cc2cc(-c3cc(C(=O)NCc4ccccc4)nn3C)ccc2[nH]1]

5-{2-Methyl-5-[(pyridin-4-ylmethyl)-carbamoyl]-2H-pyrazol-3-yl}-1H-indole-2-carboxylic acid ethyl ester Synthesized in an analogous manner to example 1, 17 mg, 11%, LC/MS ESI m/z (M+H)+=403.5.

EXAMPLE 3

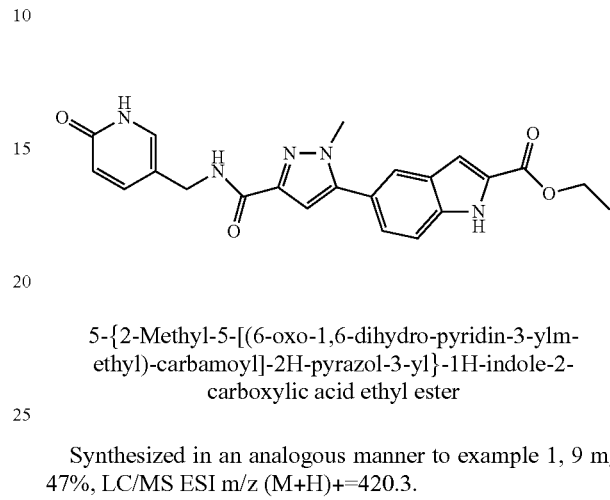

5-{2-Methyl-5-[(6-oxo-1,6-dihydro-pyridin-3-ylmethyl)-carbamoyl]-2H-pyrazol-3-yl}-1H-indole-2-carboxylic acid ethyl ester Synthesized in an analogous manner to example 1, 9 mg 47%, LC/MS ESI m/z (M+H)+=420.3.

EXAMPLE 4

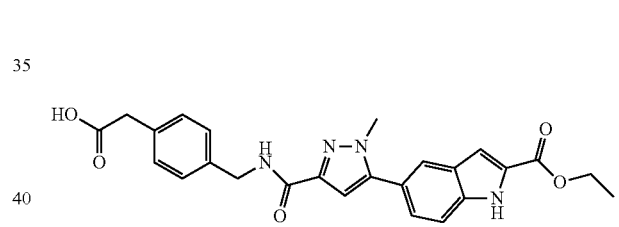

5-[5-(4-Carboxymethyl-benzylcarbamoyl)-2-methyl-2H-pyrazol-3-yl]-1H-indole-2-carboxylic acid ethyl ester Synthesized in an analogous manner to example 1, 22 mg 10.7% LC/MS ESI m/z (M+H)+=461.3.

EXAMPLE 5

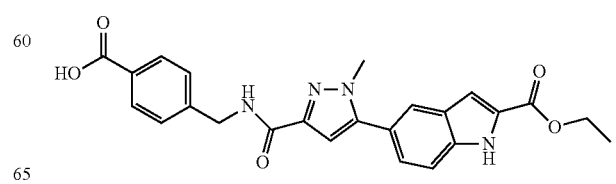

5-[5-(4-Carboxy-benzylcarbamoyl)-2-methyl-2H-pyrazol-3-yl]-1H-indole-2-carboxylic acid ethyl ester Synthesized in an analogous manner to example 1, 13 mg, 52%, LC/MS ESI m/z 446.5 (M+H)+=447.3.

EXAMPLE 6

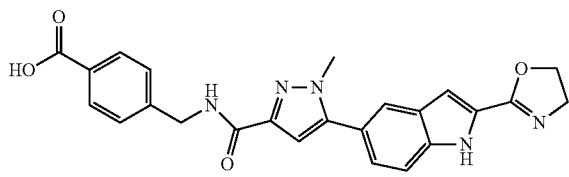 [SMILES: Cn1nc(C(=O)NCc2ccc(C(=O)O)cc2)cc1-c1ccc2[nH]c(C3=NCCO3)cc2c1]

4-[({5-[2-(4,5-Dihydro-oxazol-2-yl)-1H-indol-5-yl]-1-methyl-1H-pyrazole-3-carbonyl}-amino)-methyl]-benzoic acid Synthesized in an analogous manner to example 1, 5 mg, 12%, LC/MS ESI m/z 444.1 (M+H)+=444.4.

EXAMPLE 7

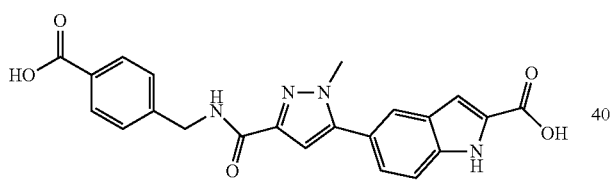

5-[5-(4-Carboxy-benzylcarbamoyl)-2-methyl-2H-pyrazol-3-yl]-1H-indole-2-carboxylic acid Synthesized in an analogous manner to example 1, 22 mg, 5%, LC/MS ESI m/z 419.6 418.4 (M+H)+=419.3.

EXAMPLE 8

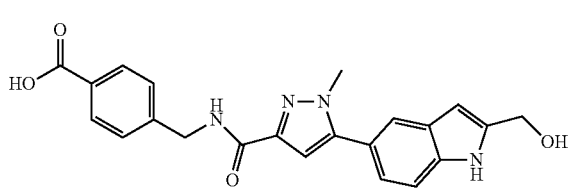 [SMILES: Cn1nc(C(=O)NCc2ccc(C(=O)O)cc2)cc1-c1ccc2[nH]c(CO)cc2c1]

4-({[5-(2-Hydroxymethyl-1H-indol-5-yl)-1-methyl-1H-pyrazole-3-carbonyl]-amino}-methyl)-benzoic acid Synthesized in an analogous manner to example 1 33 mg, 14% LC/MS ESI m/z (M+H)+=405.9.

EXAMPLE 9

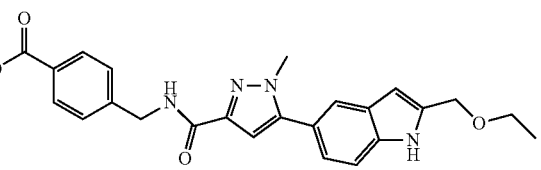

4-({[5-(2-Ethoxymethyl-1H-indol-5-yl)-1-methyl-1H-pyrazole-3-carbonyl]-amino}-methyl)-benzoic acid Synthesized in an analogous manner to example 1, 13 mg, 31% LC/MS ESI m/z (M+H)+=433.6.

EXAMPLE 10

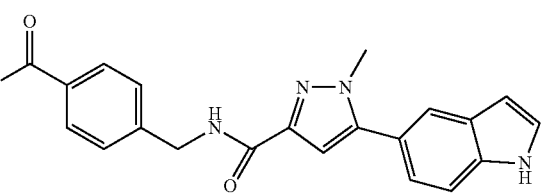

4-({[5-(1H-Indol-5-yl)-1-methyl-1H-pyrazole-3-carbonyl]-amino}-methyl)-benzoic acid Synthesized in an analogous manner to example 1, 9 mg, 18% LC/MS ESI m/z (M+H)+=375.3.

EXAMPLE 11

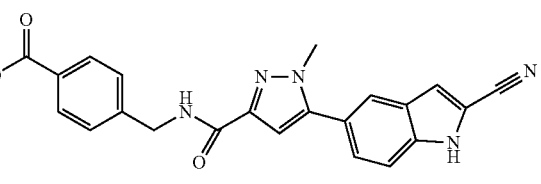

4-({[5-(2-Cyano-1H-indol-5-yl)-1-methyl-1H-pyrazole-3-carbonyl]-amino}-methyl)-benzoic acid Synthesized in an analogous manner to example 1, 7 mg 6% LC/MS ESI m/z (M+H)+=400.2.

EXAMPLE 12

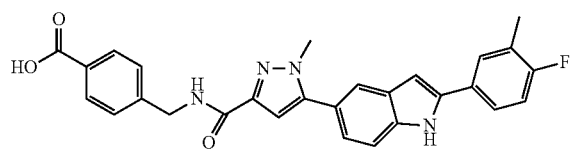 [SMILES: Cc1cc(-c2cc3cc(-c4cc(C(=O)NCc5ccc(C(=O)O)cc5)nn4C)ccc3[nH]2)ccc1F]

4-[({5-[2-(4-Fluoro-3-methyl-phenyl)-1H-indol-5-yl]-1-methyl-1H-pyrazole-3-carbonyl}-amino)-methyl]-benzoic acid Step 1.

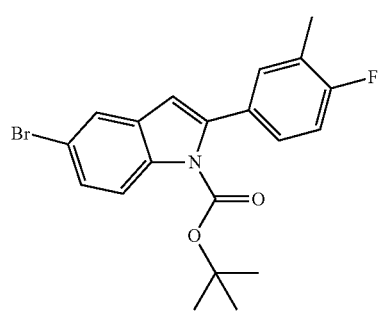

A microwave vial is charged with 4-fluoro 3-methyliodobenzene, (450 mg, 1.9 mmol), 5-bromo 1(tert-butylcarbamyl) 2-indolboronic acid (645 mg, 1.9 mmol), (Bis(di-t-butyl(4-dimethylaminophenyl)phosphine)dichloropalladium(II) (200 mg, 0.24 mmol), N,N dimethylformamide (8 ml) and aqueous sodium carbonate (2M, 4.24 mmol). The reaction tube is flushed with nitrogen, sealed, and vortex mixed. The reaction mixture heated at 100° C. via microwave for 30 minutes. The reaction mixture is diluted with ethyl acetate (20 ml) and filtered over celite. The organic layer is washed with water, dried (Na₂SO₄), evaporated in vacuo and purified on silica with hexanes/ethyl acetate as the eluent, 260 mg, (23%), LC/MS ESI m/z 404.2 (M+H)+=407.3.

Step 2

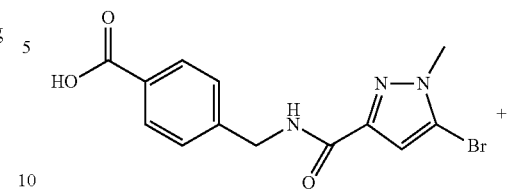

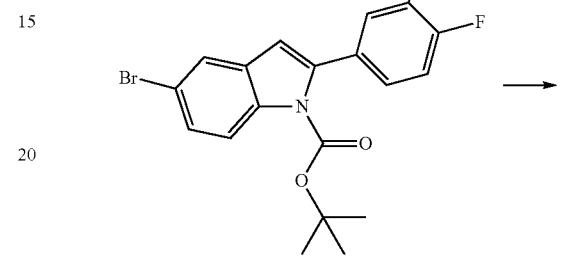

To a solution of bis(pinacolato)diboron (94 mg, 0.327 mmol), 5-Bromo-2-(4-fluoro-3-methyl-phenyl)-indole-1-carboxylic acid tert-butyl ester (75 mg, 0.18 mmol), and potassium acetate (55 mg, 55 mmol) in anhydrous 1,4-dioxane (250 uL) is added [1,1'-bis(diphenylphosphino)ferrocene]dichloropalladium(II) complex with dichloromethane (1:1) (PdCl2(dppf)*CH2Cl2) (45 mg, 0.06 mmol). The reaction mixture is heated under reflux at 100° C. for 2 hours under nitrogen. Under nitrogen, 4-{[(5-Bromo-1-methyl-1H-pyrazole-3-carbonyl)-amino]-methyl}-benzoic acid is added in N,N dimethylformamide (1 ml), followed by aqueous Na₂CO₃ (1 ml, 2N) and additional catalyst (20 mg). The reaction mixture is heated at 85° C. for 8 hours. The reaction mixture is diluted with 20 ml ethyl acetate, passed through a plug of celite and washed with water. The aqueous layer is evaporated, taken up in TFA/DCM (1:1, 5 ml) and stirred for 30 minutes. The solvent is evaporated in vacuo and the residue purified on reverse-phase HPLC to give the title compound 20 mg, (48%) LC/MS ESI m/z (M+H)+=484.5.

EXAMPLE 13

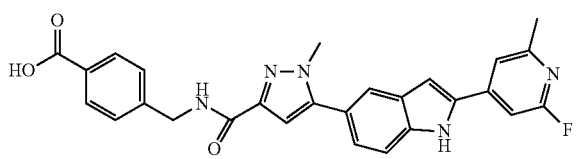 [SMILES: Cc1cc(-c2cc3cc(-c4cc(C(=O)NCc5ccc(C(=O)O)cc5)nn4C)ccc3[nH]2)cc(F)n1]

4-[({5-[2-(2-Fluoro-6-methyl-pyridin-4-yl)-1H-indol-5-yl]-1-methyl-1H-pyrazole-3-carbonyl}-amino)-methyl]-benzoic acid Synthesized in an analogous manner to example 12, 12 mg, 29% LC/MS ESI m/z (M+H)+=484.6.

EXAMPLE 14

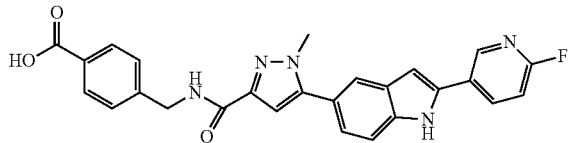 [SMILES: Cn1nc(C(=O)NCc2ccc(C(=O)O)cc2)cc1-c1ccc2[nH]c(-c3ccc(F)nc3)cc2c1]

4-[({5-[2-(6-Fluoro-pyridin-3-yl)-1H-indol-5-yl]-1-methyl-1H-pyrazole-3-carbonyl}-amino)-methyl]-benzoic acid Synthesized in an analogous manner to example 12, 24 mg, 26% yield LC/MS ESI m/z (M+H)+=470.4.

EXAMPLE 15

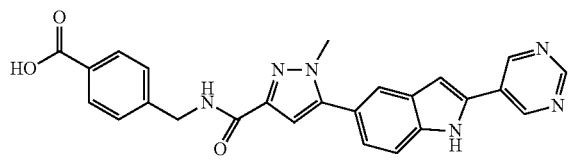 [SMILES: Cn1nc(C(=O)NCc2ccc(C(=O)O)cc2)cc1-c1ccc2[nH]c(-c3cncnc3)cc2c1]

4-({[1-Methyl-5-(2-pyrimidin-5-yl-1H-indol-5-yl)-1H-pyrazole-3-carbonyl]-amino}-methyl)-benzoic acid Synthesized in an analogous manner to example 12, 10 mg, 22.1% LC/MS ESI m/z (M+H)+=453.4.

EXAMPLE 16

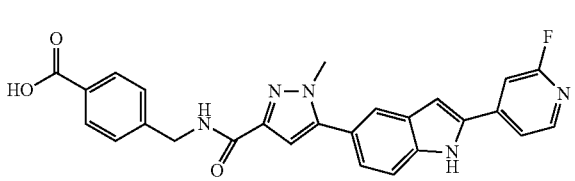 [SMILES: Cn1nc(C(=O)NCc2ccc(C(=O)O)cc2)cc1-c1ccc2[nH]c(-c3ccnc(F)c3)cc2c1]

4-[({5-[2-(2-Fluoro-pyridin-4-yl)-1H-indol-5-yl]-1-methyl-1H-pyrazole-3-carbonyl}-amino)-methyl]-benzoic acid Synthesized in an analogous manner to example 12, 8 mg, 9% yield LC/MS ESI m/z (M+H)+=470.6.

EXAMPLE 17

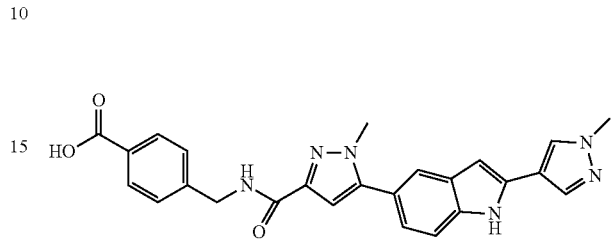

4-[({1-Methyl-5-[2-(1-methyl-1H-pyrazol-4-yl)-1H-indol-5-yl]-1H-pyrazole-3-carbonyl}-amino)-methyl]-benzoic acid Synthesized in an analogous manner to example 12, 6 mg, 18% yield LC/MS ESI m/z (M+H)+=455.4.

EXAMPLE 18

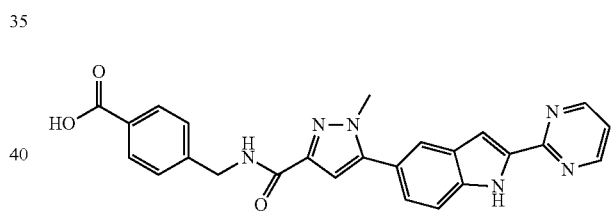

4-({[1-Methyl-5-(2-pyrimidin-2-yl-1H-indol-5-yl)-1H-pyrazole-3-carbonyl]-amino}-methyl)-benzoic acid Synthesized in an analogous manner to example 12, 10 mg, 45% LC/MS ESI m/z (M+H)+=453.4.

EXAMPLE 19

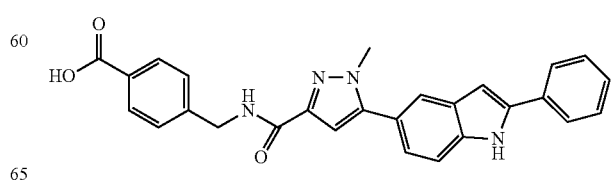

4-({[1-Methyl-5-(2-pyridin-4-yl-1H-indol-5-yl)-1H-pyrazole-3-carbonyl]-amino}-methyl)-benzoic acid Synthesized in an analogous manner to example 12, 20 mg, 29% yield LC/MS ESI m/z (M+H)+=451.5.

EXAMPLE 20

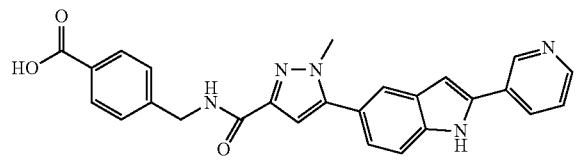 [SMILES: Cn1nc(C(=O)NCc2ccc(C(=O)O)cc2)cc1-c1ccc2[nH]c(-c3cccnc3)cc2c1]

4-({[1-Methyl-5-(2-pyridin-3-yl-1H-indol-5-yl)-1H-pyrazole-3-carbonyl]-amino}-methyl)-benzoic acid Synthesized in an analogous manner to example 12, 25 mg, 28% yield LC/MS ESI m/z (M+H)+=452.4.

EXAMPLE 21

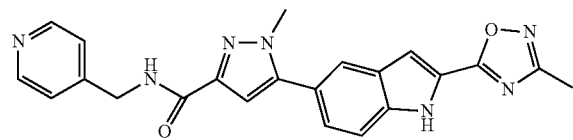 [SMILES: Cc1noc(-c2cc3cc(-c4cc(C(=O)NCc5ccncc5)nn4C)ccc3[nH]2)n1]

1-Methyl-5-[2-(3-methyl-1,2,4-oxadiazol-5-yl)-1H-indol-5-yl]-1H-pyrazole-3-carboxylic acid(pyridin-4-ylmethyl)-amide Step 1:

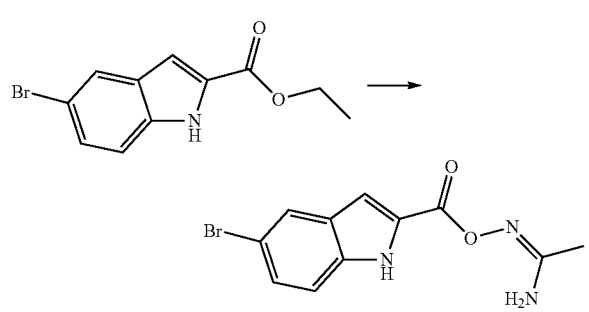

To a solution of 5-bromo 2-indolecarboxylic acid (5 g, 21 mmol) in THF (37 ml) is added carbonyldiimidazole (3.6 g, 22 mmol). The mixture is stirred for 15 minutes at room temperature. Acetamide oxime (1.9 g, 25 mmol) is then added and the mixture is stirred for 2 hours. The tetrahydrofuran is evaporated in vacuo and the resulting residue is taken up in ethyl acetate, and washed with aqueous HCl (1N, 50 ml). The organic layer is washed with brine (50 ml), dried over sodium sulfate and concentrated in vacuo to yield the title compound, 3.52 (56%) LC/MS ESI m/z (M+H)+=296.2.

Step 2:

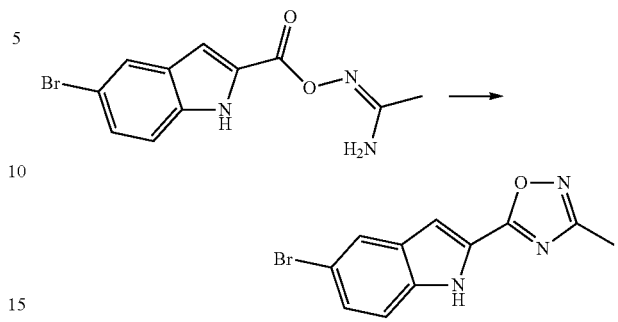

A suspension of the ester (5.08 g, 17 mmol) in tetrahydrofuran (15 ml) is heated at 150° C. in a microwave reactor for 20 minutes. Solvent is evaporated in vacuo, and the residue is triturated with a small amount of ethyl acetate. The solid is collected by vacuum filtration to give of 5-Bromo-2-(3-methyl-1,2,4-oxadiazol-5-yl)-1H-indole (2.21 g). The filtrate is evaporated in vacuo, and the resulting oil purified on silica with hexanes ethyl acetate as the eluent to give the title compound 4.90 g (89%), LC/MS ESI m/z (M+H)+=278.3.

Step 3.

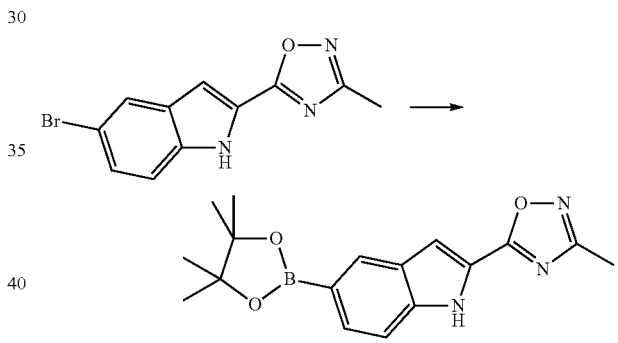

A reaction flask is charged with 5-Bromo-2-(3-methyl-1,2,4-oxadiazol-5-yl)-1H-indole (15 g, 55 mmol), bis(pinacolato)diboron (18 g, 71 mmol), tricyclohexylphosphine (1.5 g, 5.5 mmol), potassium acetate (9.7 g, 99 mmol) and Pd$_2$(dba)$_3$ (1.5 g, 2.62 mmol). 1,4-Dioxane (120 ml) is added, and the reaction is heated to 85° C. under argon for 4 hours. The reaction mixture is cooled to room temperature and filtered through celite and the celite is washed with copious amounts of ethyl acetate. The solvent is evaporated in vacuo to yield a yellow solid that is titurated with hexane (50 ml) to give the title compound 17 g, (95%) LC/MS ESI m/z (M+H)+=326.8.

Step 4:

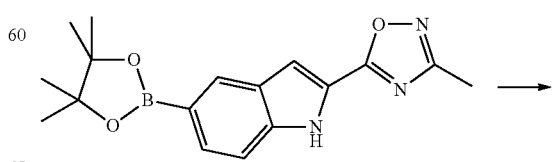

-continued

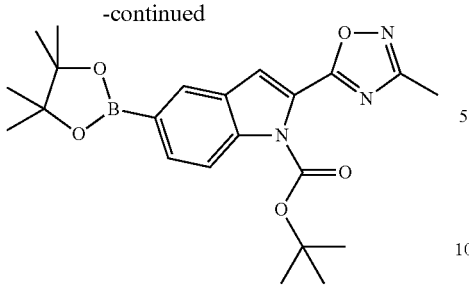

To a suspension of 2-(3-Methyl-1,2,4-oxadiazol-5-yl)-5-(4,4,5,5-tetramethyl-1,3,2-dioxaborolan-2-yl)-1H-indole (0.63 g) in N,N dimethylformamide (10 ml) is added di-tert-butyldicarbonate (500 mg, 2.2 mmol). The mixture is stirred for 45 minutes and then concentrated to dryness. The residue is dissolved in ethyl acetate (20 mL), washed with 10% citric acid solution (20 mL), brine, dried over sodium sulfate and concentrated in vacuo to yield product 0.79 g, (95%) that is used without further purification.

Step 5:

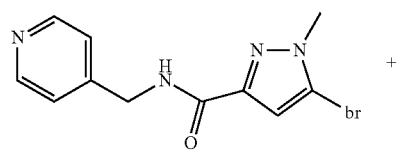 +

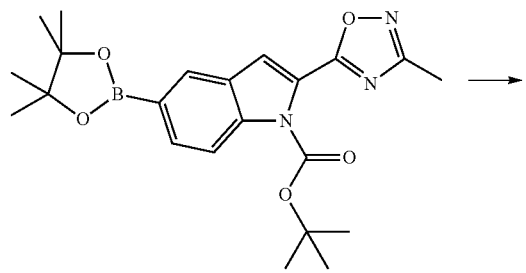 →

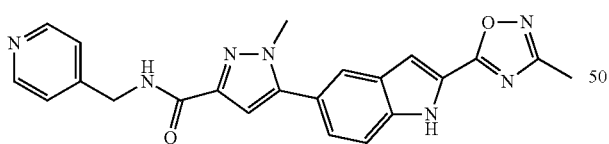

To a solution of 5-Bromo-1-methyl-1H-pyrazole-3-carboxylic acid(pyridin-4-ylmethyl)-amide (90 mg, 0.3 mmol), and 2-(3-Methyl-1,2,4-oxadiazol-5-yl)-5-(4,4,5,5-tetramethyl-1,3,2-dioxaborolan-2-yl)-indole-1-carboxylic acid tert-butyl ester (142 mg, 0.33 mmol) in N,N dimethylformamide (1.5 ml) is added aqueous Na$_2$CO$_3$ (0.4 ml, 0.77 mmol). The mixture is purged with argon for 10 minutes. (Bis(di-t-butyl(4-dimethylaminutesophenyl)phosphine)dichloropalladium(II) (40 mg, 0.06 mmol), is then added and the reaction mixture is sealed in a seal tube and heated to 100° C. in a microwave reactor for 30 minutes. The reaction mixture is diluted with ethyl acetate (70 ml), washed with water (20 ml), brine (2×25 ml), dried over Na$_2$SO$_4$, filtered, and concentrated in vacuo. Purified by reverse phase LC/MS to provide the title compound 20 mg, (16%), LC/MS ESI m/z (M+H)+= 414.9.

EXAMPLE 22

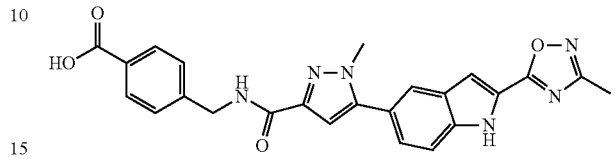

4-[({1-Methyl-5-[2-(3-methyl-1,2,4-oxadiazol-5-yl)-1H-indol-5-yl]-1H-pyrazole-3-carbonyl}-amino)-methyl]-benzoic acid Synthesized in an analogous manner to example 22, 25 mg, 23%, LC/MS ESI m/z (M+H)+=458.3.

EXAMPLE 23

1-Methyl-5-[2-(3-methyl-1,2,4-oxadiazol-5-yl)-1H-indol-5-yl]-1H-pyrazole-3-carboxylic acid 4-cyano-benzylamide Synthesized in an analogous manner to example 221, 5 mg, 15%% LC/MS ESI m/z (M+H)+=438.7.

EXAMPLE 24

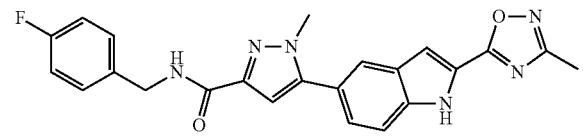 [SMILES: Cc1noc(-c2cc3cc(-c4cc(C(=O)NCc5ccc(F)cc5)nn4C)ccc3[nH]2)n1]

1-Methyl-5-[2-(3-methyl-1,2,4-oxadiazol-5-yl)-1H-indol-5-yl]-1H-pyrazole-3-carboxylic acid 4-fluorobenzylamide Synthesized in an analogous manner to example 22, 7 mg, 8% LC/MS ESI m/z (M+H)+=431.36.

EXAMPLE 25

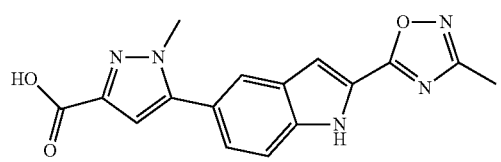 [SMILES: Cc1noc(-c2cc3cc(-c4cc(C(=O)O)nn4C)ccc3[nH]2)n1]

1-Methyl-5-[2-(3-methyl-1,2,4-oxadiazol-5-yl)-1H-indol-5-yl]-1H-pyrazole-3-carboxylic acid Step 1:

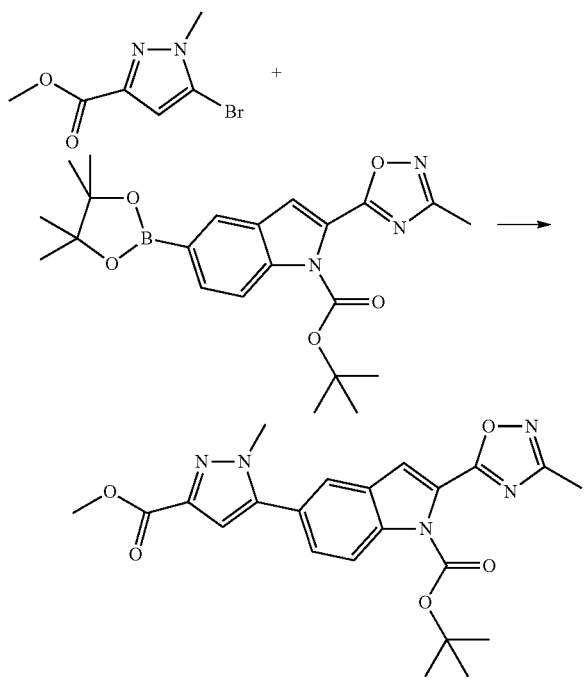

To a solution of 5-Bromo-1-methyl-1H-pyrazole-3-carboxylic acid methyl ester (3.1 g, mmol) and 2-(3-Methyl-1,2,4-oxadiazol-5-yl)-5-(4,4,5,5-tetramethyl-1,3,2-dioxaborolan-2-yl)-indole-1-carboxylic acid tert-butyl ester (5.8 g, 11.9 mmol) in toluene (60 ml) is added aqueous $Na_2CO_3$ (18 ml, 2N, 36 mmol). The mixture is purged with argon for 10 minutes. (Bis(di-t-butyl(4-dimethylaminophenyl)phosphine)dichloropalladium(II) (1.6 g, 2.4 mmol) is then added and the reaction mixture is sealed in a seal tube and heated at 110° C. in an oil bath for 12 hours. The reaction mixture is diluted with ethyl acetate, washed with water, brine, dried over $Na_2SO_4$, filtered, and evaporated in vacuo. The crude products are purified on silica with ethyl acetate/hexane as the eluent to give a colorless solid, in a 2:1 mixture of the protected and free indole, 3.7 g, 66%, LC/MS ESI m/z (M+H)+=438.2.

Step 2:

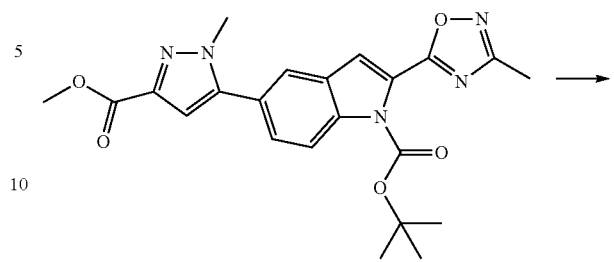

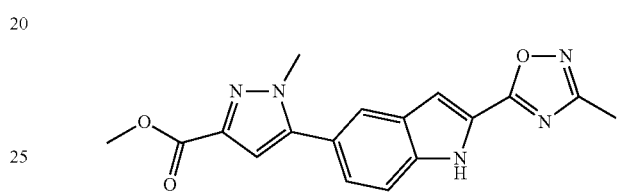

To a solution of 5-(5-Methoxycarbonyl-2-methyl-2H-pyrazol-3-yl)-2-(3-methyl-1,2,4-oxadiazol-5-yl)-indole-1-carboxylic acid tert-butyl ester (3.8 g) in dichloromethane (200 mL) is added trifluoroacetic acid (25 ml) dropwise. The reaction mixture is stirred at room temperature for 2 hours, and then the solvents are evaporated in vacuo to give a solid that is used without further purification 2.7 g, 92%.

Step 3:

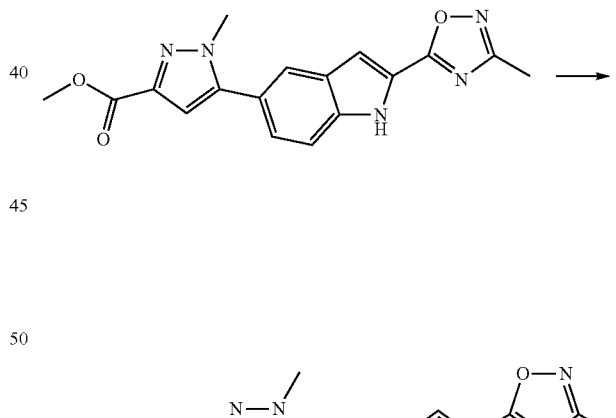

To a stirred solution of 5-(5-Methoxycarbonyl-2-methyl-2H-pyrazol-3-yl)-2-(3-methyl-1,2,4-oxadiazol-5-yl)-indole-1-carboxylic acid (2.7 g) in tetrahydrofuran (40 ml) and methanol (40 ml) at room temperature is added a solution of LiOH (3M, 103.3 mmol) in water over 5 minutes. The reaction is stirred for 30 minutes and the organic solvents are evaporated in vacuo. The reaction mixture is diluted 3x with water and washed with dichloromethane (100 ml). The aqueous layer is acidified with HCl (12 N) and the product extracted 3x with 200 ml of ethyl acetate. The combined ethyl acetate washings are dried (Na$_2$SO$_4$), filtered, and evaporated in vacuo to give the title compound 1.9 g, 57%, LC/MS ESI m/z (M+H)+=324.5.

EXAMPLE 26

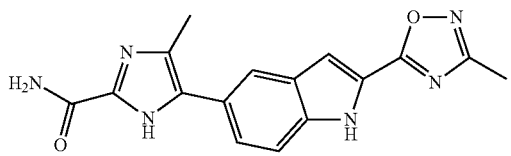 [SMILES: Cc1noc(-c2cc3cc(-c4[nH]c(C(N)=O)nc4C)ccc3[nH]2)n1]

5-Methyl-4-[2-(3-methyl-1,2,4-oxadiazol-5-yl)-1H-indol-5-yl]-1H-imidazole-2-carboxylic acid amide Step 1:

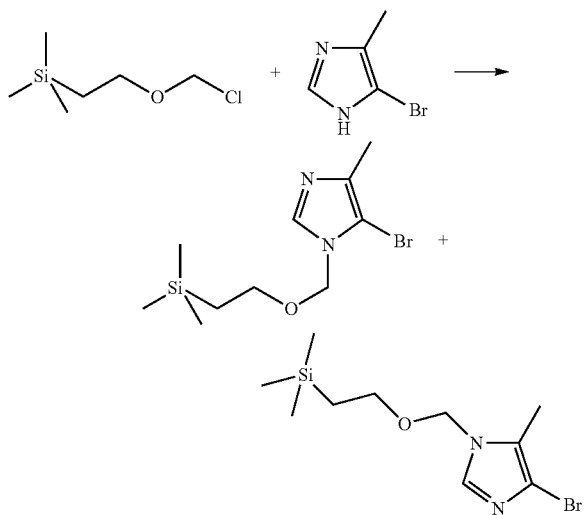

To a suspension of NaH (2.78 g, 60% 69 mmol) in tetrahydrofuran (100 ml) at 0° C. is slowly added a solution of 3-bromo-4-methylimidazole (10.0 g, 62 mmol) in dry tetrahydrofuran (100 ml) over 20 minutes. The mixture is stirred at room temperature for 1 hour. 2-(Trimethylsilyl)ethoxymethyl chloride (11 ml, 62 mmol) is then added at 0° C. and the mixture is stirred at room temperature for 2 hours. The reaction mixture is diluted with ethyl acetate (600 ml), washed with water (80 ml), brine (80 ml), dried over Na$_2$SO$_4$, filtered, and concentrated in vacuo to give a yellow oil. LC-MS the product is obtained as a ~1:1 mixture of regioisomers 38 g, 91%, LC/MS ESI m/z (M+H)+=291.4.

Step 2:

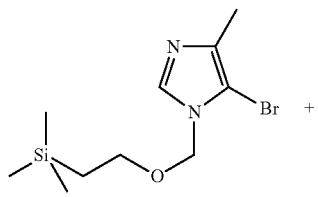

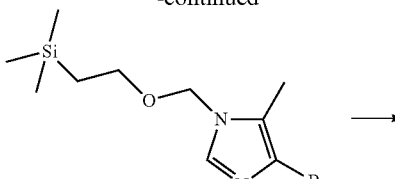

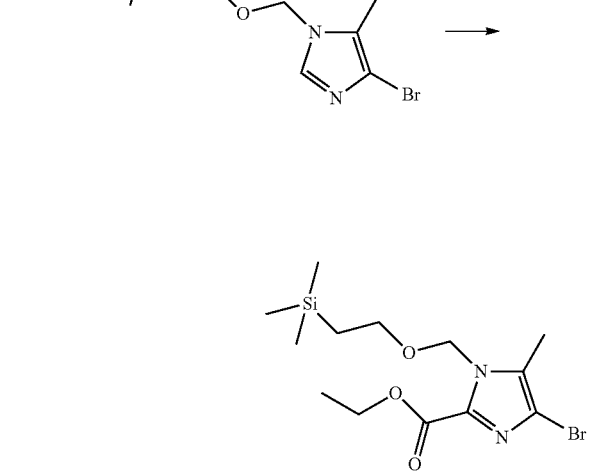

To a solution of the SEM-protected 3-bromo 4-methylimidazole (20 g, 37 mmol) in dry THF (200 ml) is added at −78° C. a freshly prepared LDA solution (n-BuLi 60 ml, 96 mmol with i-Pr$_2$NH 15.5 ml, 101 mmol, in 50 ml dry THF at −10° C. for 30 minutes). The solution is stirred at −78° C. for 1 hour, and cannulated to a solution of ethylchloroformate (13 ml, 130 mmol) in 50 ml of tetrahydrofuran at −78° C. After addition, the mixture is stirred for 30 minutes at −78° C. before it is quenched by the addition of 100 ml saturated aqueous NaHCO$_3$. The reaction mixture is diluted with ethyl acetate (1,000 ml), washed with water (100 ml), brine (100 ml), dried over Na$_2$SO$_4$, filtered, and concentrated in vacuo. The crude product is purified by chromatography on silica gel with ethyl acetate/hexane as the eluent to give the title compound as yellow oil 10 g, 40%, LC/MS ESI m/z (M+H)+= 363.3.

Step 3:

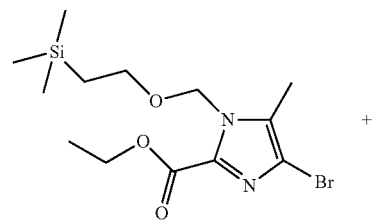

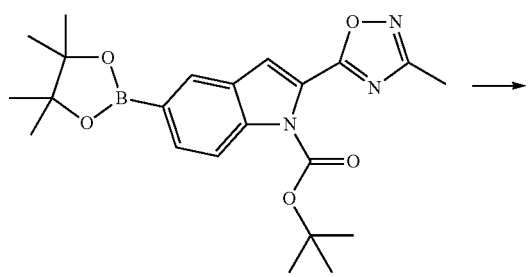

-continued

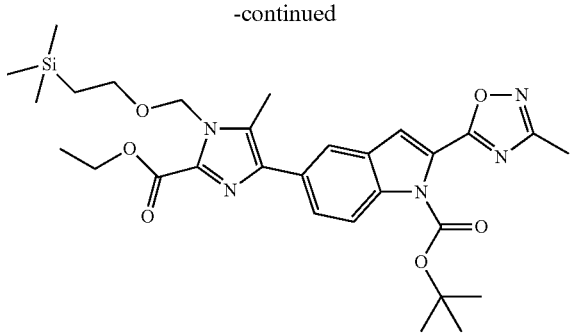

To a solution of 4-Bromo-5-methyl-1-(2-trimethylsilanyl-ethoxymethyl)-1H-imidazole-2-carboxylic acid ethyl ester (6.0 g, 14.1 mmol) and 2-(3-Methyl-1,2,4-oxadiazol-5-yl)-5-(4,4,5,5-tetramethyl-1,3,2-dioxaborolan-2-yl)-indole-1-carboxylic acid tert-butyl ester (5.0 g, 13 7 mmol) in 80 ml toluene (80 ml) is added aqueous Na$_2$CO$_3$ (14 ml, 28 mmol). The mixture is purged with argon for 3 minutes. (Bis(di-t-butyl(4-dimethylaminutesophenyl)phosphine)dichloropalladium(II) (1.9 g, 2.7 mmol), is then added and the reaction mixture is sealed in a seal tube and heated at 110° C. in oil bath for 14 hour. The reaction mixture is diluted with ethyl acetate (500 ml), washed with water (60 ml), brine (60 ml), dried over Na$_2$SO$_4$, filtered, and concentrated in vacuo. The crude product is purified by chromatography on silica with ethyl acetate/hexane as the eluent to give the title compound 5.0 g, 62%, LC/MS ESI m/z (M+H)+=582.5.

Step 4:

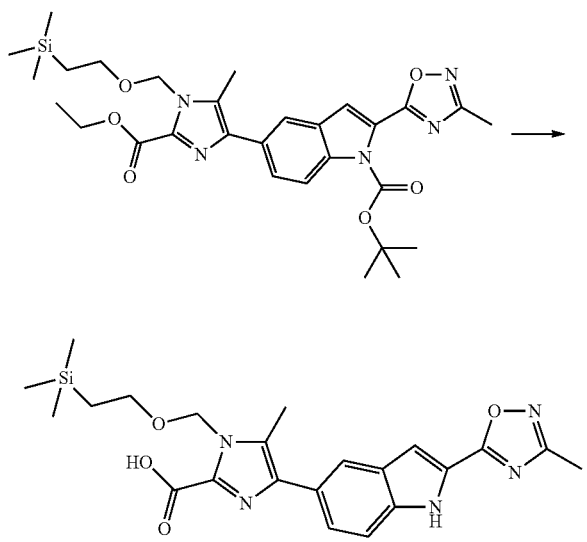

To a solution of 5-[2-Ethoxycarbonyl-5-methyl-1-(2-trimethylsilanyl-ethoxymethyl)-1H-imidazol-4-yl]-2-(3-methyl-1,2,4-oxadiazol-5-yl)-indole-1-carboxylic acid tert-butyl ester (4.6 g, 8.1 mmol) in tetrahydrofuran-methanol (1:1, 50 ml) is added aqueous NaOH (16 ml, 1N, 16 mmol) and the mixture is stirred at room temperature for 14 hours. The solvents are removed in vacuo, and the residue is purified by chromatography on silica gel (eluent, 1-25% MeOH in CH$_2$Cl$_2$) to give the desired compound 2.4 g, 66%, LC/MS ESI m/z (M+H)+=410.2.

Step 5:

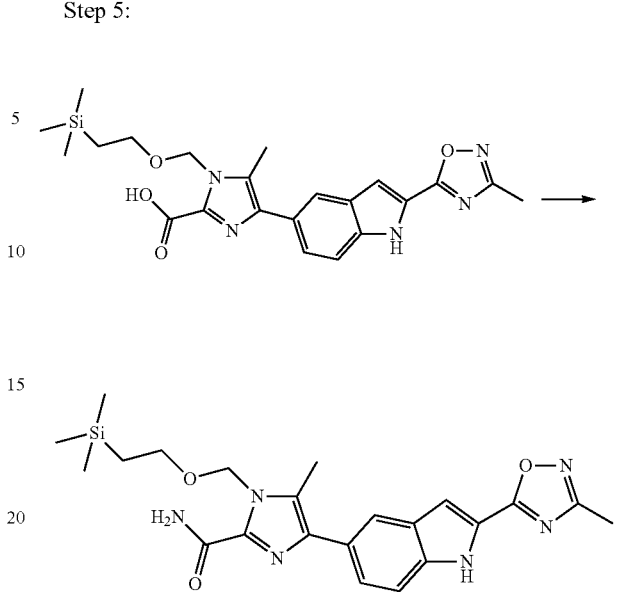

To a solution of 5-Methyl-4-[2-(3-methyl-1,2,4-oxadiazol-5-yl)-1H-indol-5-yl]-1-(2-trimethylsilanyl-ethoxymethyl)-1H-imidazole-2-carboxylic acid (170 mg, 0.37 mmol) in dry N,N dimethylforamide (2 ml) is added N-(3-Dimethylaminopropyl)-N'-ethylcarbodiimide hydrochloride (120 mg, 0.62 mmol) followed by N-Hydroxybenzotriazole (95 mg, 0.62 mmol). The mixture is stirred at room temperature for 1 hour Ammonium hydroxide (1 ml, 28%, 8 mmol) is then added and the mixture is stirred overnight. The reaction mixture is diluted with ethyl acetate (70 ml), washed with water (15 ml), brine (2×15 ml), dried over Na$_2$SO$_4$, filtered, and concentrated in vacuo. The crude product is purified by chromatography on silica with hexanes/ethyl acetate as the eluent to give the product 75 mg, 44%, LC/MS ESI m/z (M+H)+=453.4.

Step 6:

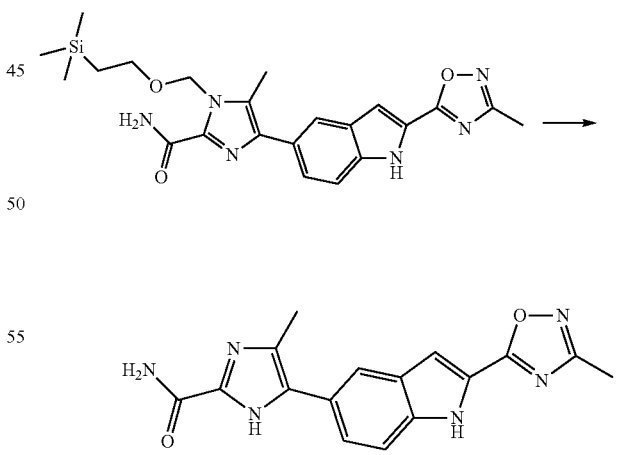

To a solution of 5-Methyl-4-[2-(3-methyl-1,2,4-oxadiazol-5-yl)-1H-indol-5-yl]-1-(2-trimethylsilanyl-ethoxymethyl)-1H-imidazole-2-carboxylic acid amide (73 mg, 0.16 mmoL) in ethanol (2 ml) is added aqueous HCl (6 N, 1 ml). The mixture is heated at 100° C. for 7 hours. After cooling the mixture, the precipitate is collected by filtration and washed with 50% ethanol in water (3 ml), and dried in vacuo to give the desired product as the HCl salt 50 mg, 58% LC/MS ESI m/z (M+H)+=324.5.

EXAMPLE 27

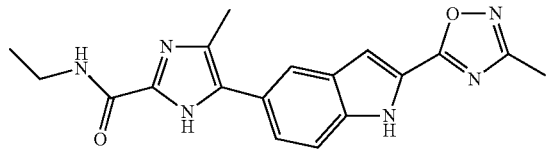 [SMILES: CCNC(=O)c1nc(C)c(-c2ccc3[nH]c(-c4nc(C)no4)cc3c2)[nH]1]

5-Methyl-4-[2-(3-methyl-1,2,4-oxadiazol-5-yl)-1H-indol-5-yl]-1H-imidazole-2-carboxylic acid ethylamide Synthesized in an analogous manner to example 26, 1.0 g, 96% LC/MS ESI m/z (M+H)+=351.9.

EXAMPLE 28

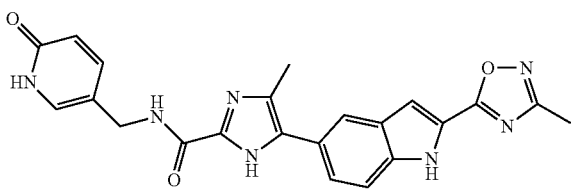 [SMILES: Cc1noc(-c2cc3cc(-c4[nH]c(C(=O)NCc5ccc(=O)[nH]c5)nc4C)ccc3[nH]2)n1]

5-Methyl-4-[2-(3-methyl-1,2,4-oxadiazol-5-yl)-1H-indol-5-yl]-1H-imidazole-2-carboxylic acid(6-oxo-1,6-dihydro-pyridin-3-ylmethyl)-amide Synthesized in an analogous manner to example 26, 15 mg, 35% LC/MS ESI m/z (M+H)+=430.3.

EXAMPLE 29

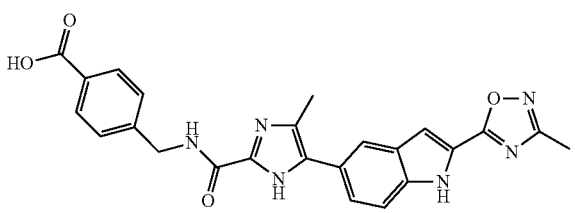 [SMILES: Cc1noc(-c2cc3cc(-c4[nH]c(C(=O)NCc5ccc(C(=O)O)cc5)nc4C)ccc3[nH]2)n1]

4-[({5-Methyl-4-[2-(3-methyl-1,2,4-oxadiazol-5-yl)-1H-indol-5-yl]-1H-imidazole-2-carbonyl}-amino)-methyl]-benzoic acid Synthesized in an analogous manner to example 29, 23 mg, 61% LC/MS ESI m/z (M+H)+=457.7.

EXAMPLE 30

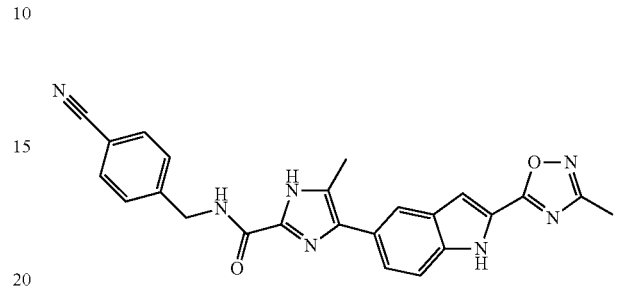

5-Methyl-4-[2-(3-methyl-1,2,4-oxadiazol-5-yl)-1H-indol-5-yl]-1H-imidazole-2-carboxylic acid 4-cyano-benzylamide Step 1:

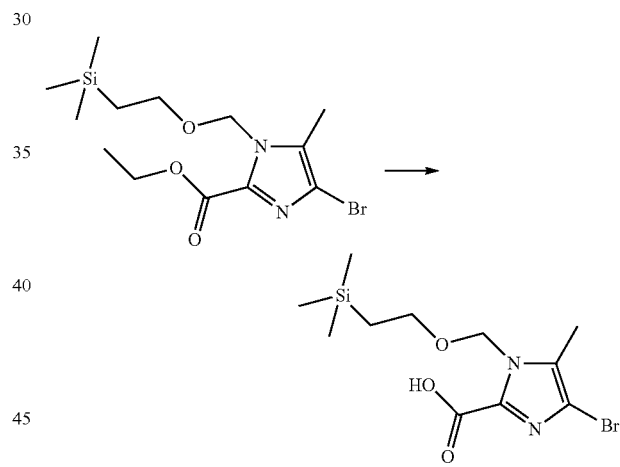

To a solution of 4-Bromo-5-methyl-1-(2-trimethylsilanyl-ethoxymethyl)-1H-imidazole-2-carboxylic acid ethyl ester (3.4 g, 9 3 mmol) in of dioxane/water (3/2, 100 ml) is added LiOH (787 mg, 18.7 mmol) and the reaction is stirred at room temperature for 2 hours. The solvent is evaporated in vacuo and the residue is purified on silica with methanol/dichloromethane as the eluent to give the product as a white solid 2.9 g, 92%, LC/MS ESI m/z (M+H)+=451.2.

Step 2:

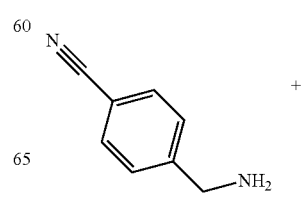

-continued

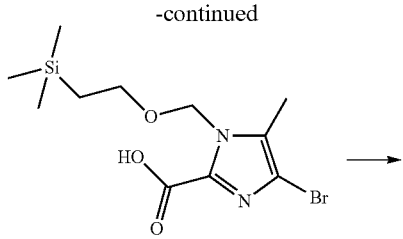

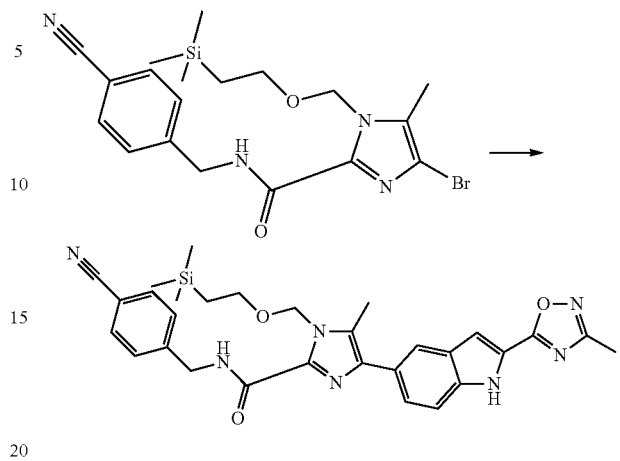

Step 3:

To a solution of 4-Bromo-5-methyl-1-(2-trimethylsilanyl-ethoxymethyl)-1H-imidazole-2-carboxylic acid 4-cyano-benzylamide (84 mg, 0.18 mmol) and 2-(3-Methyl-1,2,4-oxadiazol-5-yl)-5-(4,4,5,5-tetramethyl-1,3,2-dioxaborolan-2-yl)-indole-1-carboxylic acid tert-butyl ester (79 mg, 0.19 mmol) in N,N dimethylformamide (1.5 ml) is added aqueous $Na_2CO_3$ (0.2 ml, 0.4 mmol). The mixture is purged with argon for 10 minutes. (Bis(di-t-butyl(4-dimethylaminutesophenye-phosphine)dichloropalladium(II) (35 mg, 0.05 mmol) is added and the reaction mixture is sealed in a seal tube and heated to 120° C. in a microwave reactor for 30 minutes. The reaction mixture is diluted with ethyl acetate (15 ml), washed with water (5 ml), brine (5 ml), dried over $Na_2SO_4$, filtered, and concentrated in vacuo. The crude product is purified on silica with ethyl acetate/hexane as the eluent 100 mg, 94%, LC/MS ESI m/z (M+H)+=568.4.

4-Bromo-5-methyl-1-(2-trimethylsilanyl-ethoxymethyl)-1H-imidazole-2-carboxylic acid (0.79 mmol) in N,N dimethylformamide (5 ml) is added HATU (450 mg, 1.2 mmol) followed by N,N-diisopropylethylamine (437 uL, 2.4 mmol). The reaction is stirred for ½ hour. 4-Aminomethyl-benzonitrile (200 mg, 1.2 mmol) is added at 0° C. The reaction mixture is stirred for 3 hours at room temperature. The solvent is evaporated and the residue is purified on silica with ethyl acetate/hexane as the eluent to give product, 300 mg, 85%, LC/MS ESI m/z (M+H)+=451.2.

Step 4:

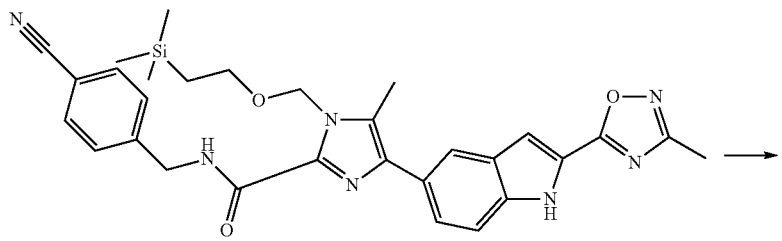

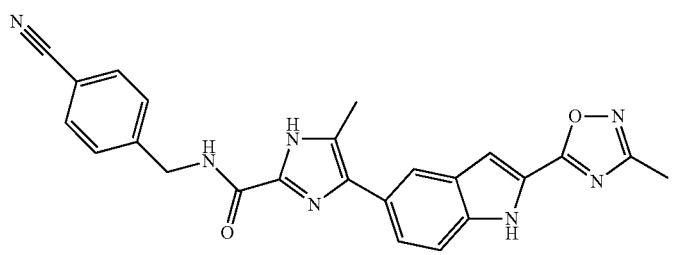

To 5-Methyl-4-[2-(3-methyl-1,2,4-oxadiazol-5-yl)-1H-indol-5-yl]-1-(2-trimethylsilanyl-ethoxymethyl)-1H-imidazole-2-carboxylic acid 4-cyano-benzylamide (75 mg, 0.13 mmol) in of dioxane (2.5 ml) is added aqueous HCl (3M, 2.5 ml) and is the mixture is heated at 100° C. for 4 hours. The solvent is evaporated and the residue is purified on silica with ethyl acetate/hexane as the eluent to give product 12 mg, 21%, LC/MS ESI m/z (M+H)+=438.4.

EXAMPLE 31

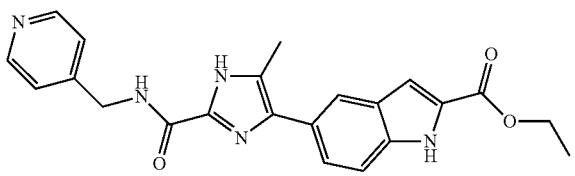 [SMILES: CCOC(=O)c1cc2cc(-c3nc(C(=O)NCc4ccncc4)[nH]c3C)ccc2[nH]1]

5-{5-Methyl-2-[(pyridin-4-ylmethyl)-carbamoyl]-3H-imidazol-4-yl}-1H-indole-2-carboxylic acid ethyl ester Synthesized in an analogous manner to example 30, 5.0 mg, 3.3% LC/MS ESI m/z (M+H)+=404.1.

EXAMPLE 32

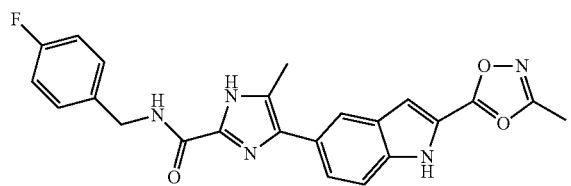

5-Methyl-4-[2-(3-methyl-1,2,4-oxadiazol-5-yl)-1H-indol-5-yl]-1H-imidazole-2-carboxylic acid 4-fluoro-benzylamide Synthesized in an analogous manner to example 30, 8.0 mg, 49% LC/MS ESI m/z (M+H)+=432.2.

EXAMPLE 33

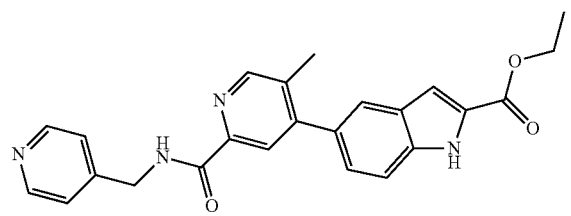 [SMILES: CCOC(=O)c1cc2cc(-c3cc(C(=O)NCc4ccncc4)ncc3C)ccc2[nH]1]

5-{5-Methyl-2-[(pyridin-4-ylmethyl)-carbamoyl]-pyridin-4-yl}-1H-indole-2-carboxylic acid ethyl ester Step 1:

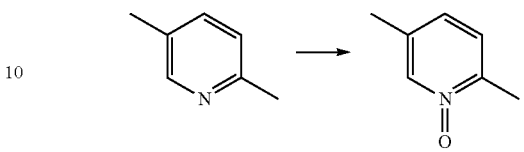

To 2,5-Dimethylpyridine (32 g, 298 mmol) in acetic acid (120 ml) maintained at 55-60° C. is added H$_2$O$_2$ (20 ml) dropwise over a period of 15 minutes. After 2 hours additional H$_2$O$_2$ (20 ml) is added and heating is continued for 24 hours. The reaction mixture is carefully concentrated to 85 ml and water (50 mL) is added. The reaction mixture is neutralized by adding solid Na$_2$CO$_3$. It is extracted with dichloromethane, 3×150 ml). The combined organic layer is washed with water (150 ml), collected, dried (Na$_2$SO$_4$), filtered and evaporated in vacuo to give a solid, that is used without further purification 24 g, 65%, LC/MS ESI m/z (M+H)+=124.2.

Step 2:

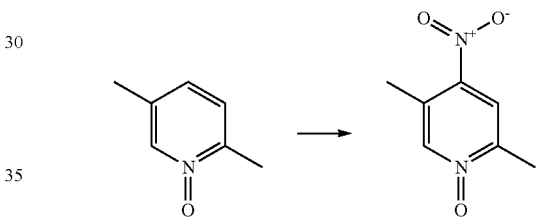

2,5-Dimethylpyridine N-oxide (20 g, 162 mmol) is slowly added to a stirred solution of nitrating mixture [99% HNO$_3$ (32 ml)+98% sulphuric acid (130 ml)] over 30 minutes. The temperature is raised to 100° C. and the reaction stirred for 6 hours. The reaction mixture is cooled to room temperature, poured into ice (2 kg) and neutralized to pH 7 by addition of solid Na$_2$CO$_3$. The white solid obtained is recrystallized from ethanol, 20 g 73% LC/MS ESI m/z (M+H)+=170.0.

Step 3:

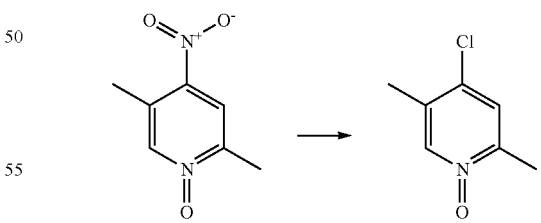

POCl$_3$ (80 ml) is added dropwise to a stirred solution of 2,5-Dimethyl 4-nitropyridine N-oxide (20 g, 119 mmol) at 0° C. in dichloromethane (250 ml). The reaction mixture is slowly warmed to room temperature and stirred for 28 hours. The reaction mixture is poured over crushed ice and basified with 40% aqueous NaOH solution. The mixture is extracted with dichloromethane (3×200 ml). The combined organic extract is washed with brine, dried (Na$_2$SO$_4$), filtered and evaporated in vacuo. The crude product is purified on silica with methanol/dichloromethane as the eluent, 18 g, 47% LC/MS ESI m/z (M+H)+=158.2.

Step 4:

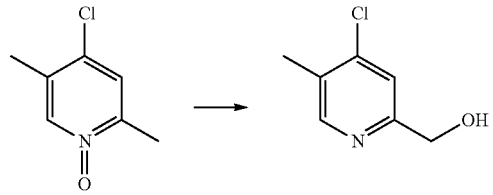

2,5-Dimethyl-4-chloropyridine N-oxide (5 g, 31 mmol) is dissolved in acetic anhydride (35 ml) and heated to 110° C. for 5 h. The acetic anhydride is evaporated and the dark residue which is obtained is dissolved in aqueous HCl (2N) and heated to 90° C. for 2.5 hours. The reaction mixture is cooled to room temperature and the pH is adjusted to 7-8 with solid Na$_2$CO$_3$. It is then extracted with dichloromethane (40 ml 3×). The combined organic layers are washed with brine, collected, dried (Na$_2$SO$_4$), and evaporated in vacuo. The crude product is purified on silica with dichloromethane/methanol as the eluent 2.2 g 46%, LC/MS ESI m/z (M+H)+=158.2.

Step 5:

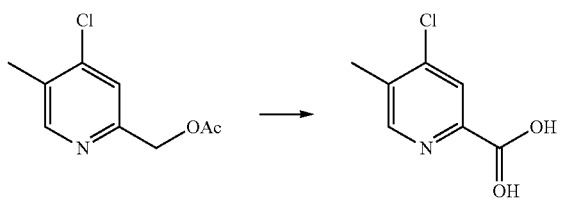

To a solution of Acetic acid 4-chloro-5-methyl-pyridin-2-ylmethyl ester (10 g, 63 mmol) in acetone (80 ml) is added potassium permanganate (13 g, 82 mmol) in water (500 ml) at 0-5° C. for 40 minutes. The reaction is heated to 55° C. for 1 hour. The reaction mixture is filtered through Celite and the filtrate is concentrated under reduced pressure. The aqueous layer is acidified with 2M aqueous HCl to pH-2 to 3. The aqueous layer is extracted with 10% methanol in dichloromethane (3×100 ml). The combined organic layer is collected, dried (Na$_2$SO$_4$), filtered, and evaporated in vacuo. Crystallization of the residue from dichloromethane+diethyl ether+hexanes gives product 5 g, 46%, LC/MS ESI m/z (M+H)+=172.2.

Step 6:

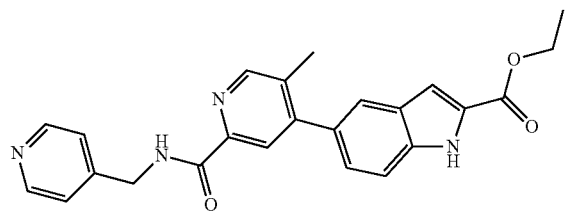 [SMILES: CCOC(=O)c1cc2cc(-c3cc(C(=O)NCc4ccncc4)ncc3C)ccc2[nH]1]

Synthesized in an analogous manner to example 30, 10 mg, 53% LC/MS ESI m/z (M+H)+=415.6.

EXAMPLE 34

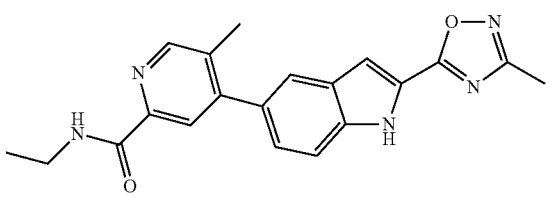 [SMILES: CCNC(=O)c1cc(-c2ccc3[nH]c(-c4nc(C)no4)cc3c2)c(C)cn1]

5-Methyl-4-[2-(3-methyl-1,2,4-oxadiazol-5-yl)-1H-indol-5-yl]-pyridine-2-carboxylic acid ethylamide Synthesized in an analogous manner to example 30, 20 mg, 13%, LC/MS ESI m/z (M+H)+=362.4.

EXAMPLE 35

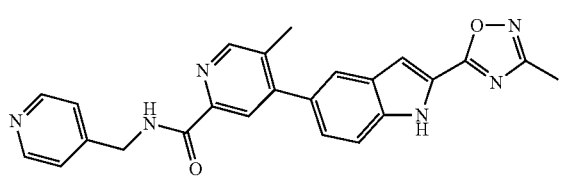 [SMILES: Cc1noc(-c2cc3cc(-c4cc(C(=O)NCc5ccncc5)ncc4C)ccc3[nH]2)n1]

5-Methyl-4-[2-(3-methyl-1,2,4-oxadiazol-5-yl)-1H-indol-5-yl]-pyridine-2-carboxylic acid(pyridin-4-ylmethyl)-amide Synthesized in an analogous manner to example 30, 11 mg, 12%, LC/MS ESI m/z (M+H)+=425.4.

EXAMPLE 36

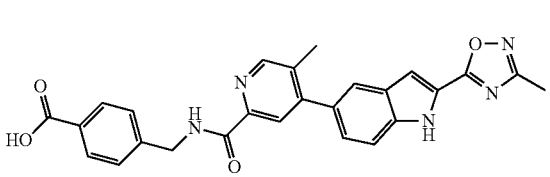 [SMILES: Cc1noc(-c2cc3cc(-c4cc(C(=O)NCc5ccc(C(=O)O)cc5)ncc4C)ccc3[nH]2)n1]

4-[({5-Methyl-4-[2-(3-methyl-1,2,4-oxadiazol-5-yl)-1H-indol-5-yl]-pyridine-2-carbonyl}-amino)-methyl]-benzoic acid Synthesized in an analogous manner to example 30, 12 mg, 24%, LC/MS ESI m/z (M+H)+=468.5.

EXAMPLE 37

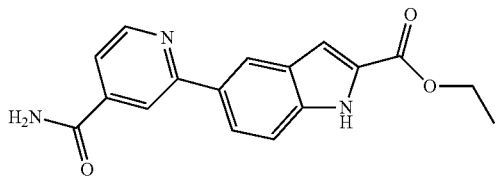 [SMILES: CCOC(=O)c1cc2cc(-c3cc(C(N)=O)ccn3)ccc2[nH]1]

5-(4-Carbamoyl-pyridin-2-yl)-1H-indole-2-carboxylic acid ethyl ester

Synthesized in an analogous manner to example 30, 22 mg, 22%, LC/MS ESI m/z (M+H)+=310.1

EXAMPLE 38

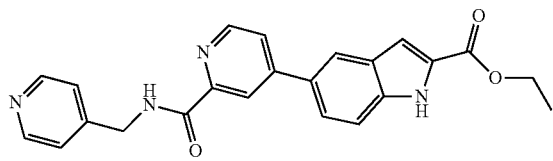 [SMILES: CCOC(=O)c1cc2cc(-c3ccnc(C(=O)NCc4ccncc4)c3)ccc2[nH]1]

5-{2-[(Pyridin-4-ylmethyl)-carbamoyl]-pyridin-4-yl}-1H-indole-2-carboxylic acid ethyl ester Synthesized in an analogous manner to example 30, 50 mg, 77%, LC/MS ESI m/z (M+H)+=401.3.

EXAMPLE 39

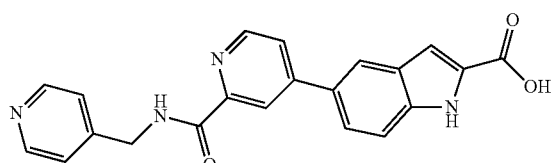

5-{2-[(Pyridin-4-ylmethyl)-carbamoyl]-pyridin-4-yl}-1H-indole-2-carboxylic acid

To 5-{2-[(Pyridin-4-ylmethyl)-carbamoyl]-pyridin-4-yl}-1H-indole-2-carboxylic acid ethyl ester (160 mg, 0.4 mmol) in ethanol (4 ml) is added aqueous sodium hydroxide (2N) and the mixture is stirred at 70° C. for 2 hours. The reaction is cooled, diluted with water (30 ml), acidified with aqueous HCl (3N) to pH 4-5, extracted with dichloromethane (50 ml). The combined organic layer is dried (sodium sulfate), filtered and evaporated in vacuo to give the title compound, 95 mg, 64%, LC/MS ESI m/z (M+H)+=273.8.

EXAMPLE 40

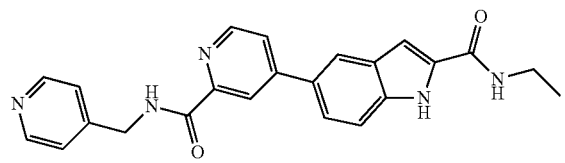 [SMILES: CCNC(=O)c1cc2cc(-c3ccnc(C(=O)NCc4ccncc4)c3)ccc2[nH]1]

5-{2-[(Pyridin-4-ylmethyl)-carbamoyl]-pyridin-4-yl}-1H-indole-2-carboxylic acid ethylamide To a mixture of 5-{2-[(Pyridin-4-ylmethyl)-carbamoyl]-pyridin-4-yl}-1H-indole-2-carboxylic acid (40 mg, 0.1 mmol) in N,N dimethylformamide (1 ml) is added HATU (49 mg, 0.13 mmol) followed by N,N-diisopropylethylamine (0.025 ml. 0.12 mmol). The reaction is stirred for ½ hour. The ethylamine (64 uL, 0.13 mmol) is added and the reaction mixture stirred for 24 hours. The reaction mixture is diluted with ethyl acetate and is washed 3× with water, 1× with sodium carbonate and 1× with brine. The organic layer dried over Na$_2$SO$_4$, filtered, and is evaporated in vacuo. The crude product is purified by reverse phase HPLC to give the title compound 8 mg, 19%, LC/MS ESI m/z (M+H)+=400.4.

EXAMPLE 41

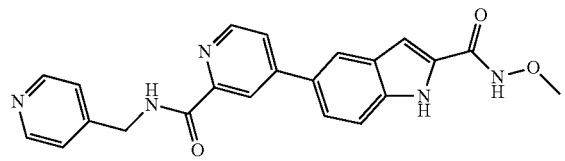 [SMILES: CONC(=O)c1cc2cc(-c3ccnc(C(=O)NCc4ccncc4)c3)ccc2[nH]1]

5-{2-[(Pyridin-4-ylmethyl)-carbamoyl]-pyridin-4-yl}-1H-indole-2-carboxylic acid methoxy-amide Synthesized in an analogous manner to example 30, 17 mg, 63% LC/MS ESI m/z (M+H)+=402.4.

EXAMPLE 42

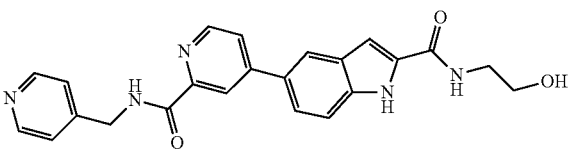 [SMILES: O=C(NCc1ccncc1)c1cc(-c2ccc3[nH]c(C(=O)NCCO)cc3c2)ccn1]

5-{2-[(Pyridin-4-ylmethyl)-carbamoyl]-pyridin-4-yl}-1H-indole-2-carboxylic acid(2-hydroxy-ethyl)-amide Synthesized in an analogous manner to example 30, 45 mg, 44% LC/MS ESI m/z (M+H)+=416.4.

EXAMPLE 43

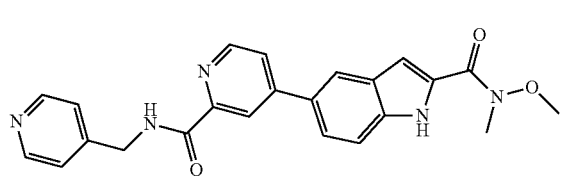 [SMILES: CON(C)C(=O)c1cc2cc(-c3ccnc(C(=O)NCc4ccncc4)c3)ccc2[nH]1]

5-{2-[(Pyridin-4-ylmethyl)-carbamoyl]-pyridin-4-yl}-1H-indole-2-carboxylic acid methoxy-methyl-amide Synthesized in an analogous manner to example 30, 20 mg, 47% LC/MS ESI m/z (M+H)+=416.2.

EXAMPLE 44

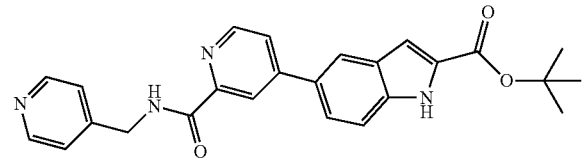 [SMILES: CC(C)(C)OC(=O)c1cc2cc(-c3ccnc(C(=O)NCc4ccncc4)c3)ccc2[nH]1]

5-{2-[(Pyridin-4-ylmethyl)-carbamoyl]-pyridin-4-yl}-1H-indole-2-carboxylic acid tert-butyl ester Synthesized in an analogous manner to example 30, 10 mg, 22% LC/MS ESI m/z (M+H)+=429.4.

EXAMPLE 45

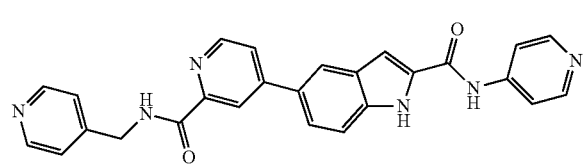 [SMILES: O=C(NCc1ccncc1)c1cc(-c2ccc3[nH]c(C(=O)Nc4ccncc4)cc3c2)ccn1]

5-{2-[(Pyridin-4-ylmethyl)-carbamoyl]-pyridin-4-yl}-1H-indole-2-carboxylic acid pyridin-4-ylamide Synthesized in an analogous manner to example 30, 10 mg, 21% LC/MS ESI m/z (M+H)+=449.3.

EXAMPLE 46

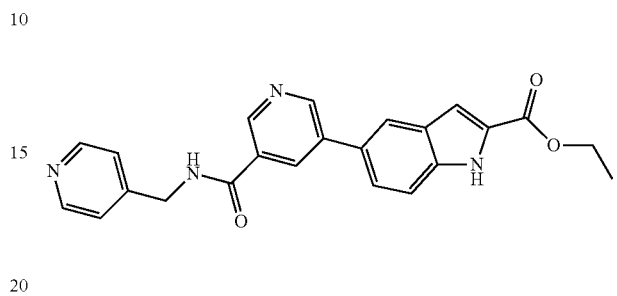

5-{5-[(Pyridin-4-ylmethyl)-carbamoyl]-pyridin-3-yl}-1H-indole-2-carboxylic acid ethyl ester Synthesized in an analogous manner to example 30, 28 mg, 43% LC/MS ESI m/z (M+H)+=401.4.

EXAMPLE 47

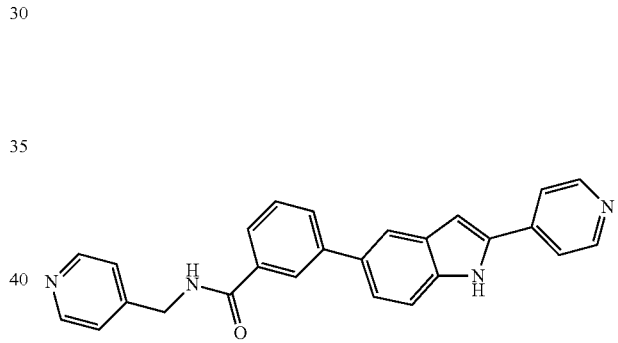

3-(2-Pyridin-4-yl-1H-indol-5-yl)-N-pyridin-4-ylmethyl-benzamide

Synthesized in an analogous manner to example 30, 40 mg, 46% LC/MS ESI m/z (M+H)+=405.6.

EXAMPLE 48

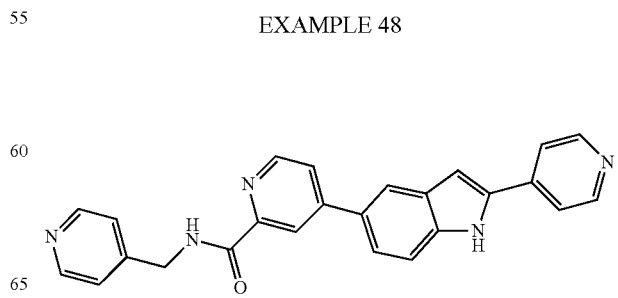

4-(2-Pyridin-4-yl-1H-indol-5-yl)-pyridine-2-carboxylic acid(pyridin-4-ylmethyl)-amide Synthesized in an analogous manner to example 30, 15 mg, 47% LC/MS ESI m/z (M+H)+=406.4.

EXAMPLE 49

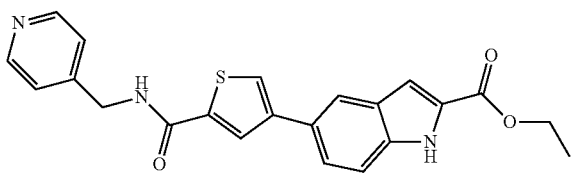 [SMILES: CCOC(=O)c1cc2cc(-c3csc(C(=O)NCc4ccncc4)c3)ccc2[nH]1]

5-{5-[(Pyridin-4-ylmethyl)-carbamoyl]-thiophen-3-yl}-1H-indole-2-carboxylic acid ethyl ester Synthesized in an analogous manner to example 30, 30 mg, 36% LC/MS ESI m/z (M+H)+=406.4.

EXAMPLE 50

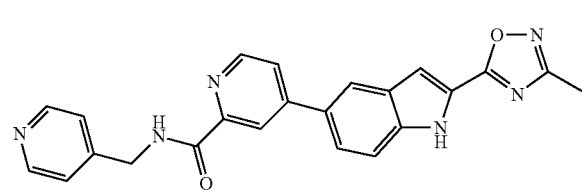 [SMILES: Cc1noc(-c2cc3cc(-c4ccnc(C(=O)NCc5ccncc5)c4)ccc3[nH]2)n1]

4-[2-(3-Methyl-1,2,4-oxadiazol-5-yl)-1H-indol-5-yl]-pyridine-2-carboxylic acid(pyridin-4-ylmethyl)-amide Synthesized in an analogous manner to example 30, 10 mg, 31% LC/MS ESI m/z (M+H)+=411.1.

EXAMPLE 51

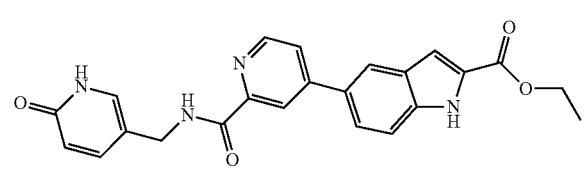 [SMILES: CCOC(=O)c1cc2cc(-c3ccnc(C(=O)NCc4ccc(=O)[nH]c4)c3)ccc2[nH]1]

5-{2-[(6-Oxo-1,6-dihydro-pyridin-3-ylmethyl)-carbamoyl]-pyridin-4-yl}-1H-indole-2-carboxylic acid ethyl ester Synthesized in an analogous manner to example 30, 15 mg, 22% LC/MS ESI m/z (M+H)+=417.4.

EXAMPLE 52

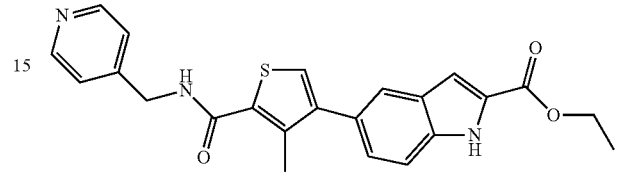

5-{4-Methyl-5-[(pyridin-4-ylmethyl)-carbamoyl]-thiophen-3-yl}-1H-indole-2carboxylic acid ethyl ester Synthesized in an analogous manner to example 30, 30 mg, 82% LC/MS ESI m/z (M+H)+=420.4.

EXAMPLE 53

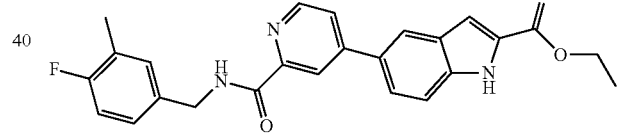

5-[2-(4-Fluoro-3-methyl-benzylcarbamoyl)-pyridin-4-yl]-1H-indole-2-carboxylic acid ethyl ester Synthesized in an analogous manner to example 30, 15 mg, 14% LC/MS ESI m/z (M+H)+=432.2.

EXAMPLE 54

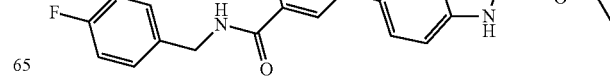

5-[5-(4-Fluoro-3-methyl-benzylcarbamoyl)-pyridin-3-yl]-1H-indole-2-carboxylic acid ethyl ester Synthesized in an analogous manner to example 30, 26 mg, 25% LC/MS ESI m/z (M+H)+=432.4.

EXAMPLE 55

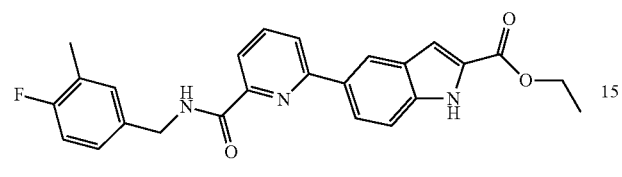

5-[6-(4-Fluoro-3-methyl-benzylcarbamoyl)-pyridin-2-yl]-1H-indole-2-carboxylic acid ethyl ester Synthesized in an analogous manner to example 30, 22 mg, 21% LC/MS ESI m/z (M+H)+=432.2.

EXAMPLE 56

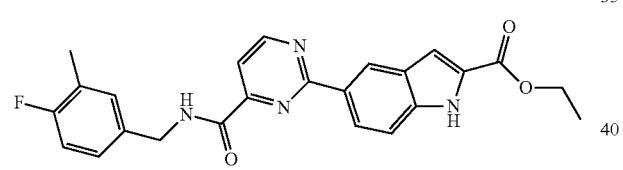

5-[4-(4-Fluoro-3-methyl-benzylcarbamoyl)-pyrimidin-2-yl]-1H-indole-2-carboxylic acid ethyl ester Synthesized in an analogous manner to example 30, 20 mg, 29% LC/MS ESI m/z (M+H)+=433.3.

EXAMPLE 57

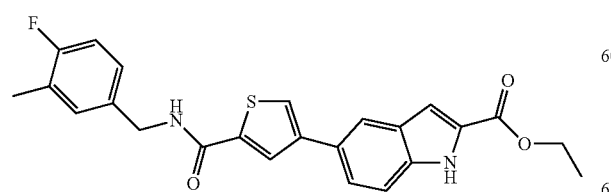

5-[5-(4-Fluoro-3-methyl-benzylcarbamoyl)-thiophen-3-yl]-1H-indole-2-carboxylic acid ethyl ester Synthesized in an analogous manner to example 30, 40 mg, 41% LC/MS ESI m/z (M+H)+=437.4.

EXAMPLE 58

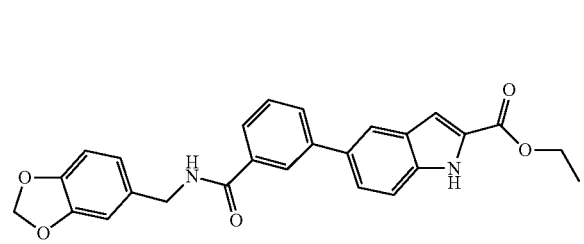 [SMILES: CCOC(=O)c1cc2cc(-c3cccc(C(=O)NCc4ccc5c(c4)OCO5)c3)ccc2[nH]1]

5-{3-[(1,3-Benzodioxol-5-ylmethyl)-carbamoyl]-phenyl}-1H-indole-2-carboxylic acid ethyl ester Synthesized in an analogous manner to example 30, 45 mg, 25% LC/MS ESI m/z (M+H)+=443.1.

EXAMPLE 59

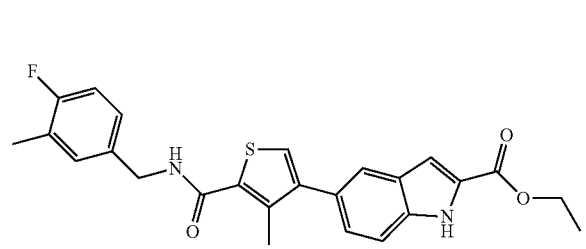 [SMILES: CCOC(=O)c1cc2cc(-c3csc(C(=O)NCc4ccc(F)c(C)c4)c3C)ccc2[nH]1]

5-[5-(4-Fluoro-3-methyl-benzylcarbamoyl)-4-methyl-thiophen-3-yl]-1H-indole-2-carboxylic acid ethyl ester Synthesized in an analogous manner to example 30, 100 mg, 83% LC/MS ESI m/z (M+H)+=451.2.

EXAMPLE 60

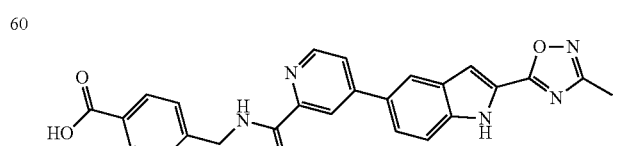

4-[({4-[2-(3-Methyl-1,2,4-oxadiazol-5-yl)-1H-indol-5-yl]-pyridine-2-carbonyl}-amino)-methyl]-benzoic acid Synthesized in an analogous manner to example 30, 12 mg, 62% LC/MS ESI m/z (M+H)+=460.2.

EXAMPLE 61

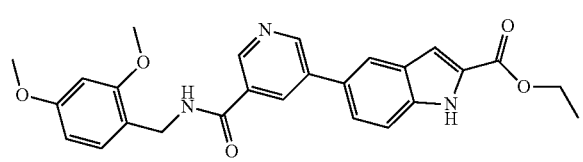 [SMILES: CCOC(=O)c1cc2cc(-c3cncc(C(=O)NCc4ccc(OC)cc4OC)c3)ccc2[nH]1]

5-[5-(2,4-Dimethoxy-benzylcarbamoyl)-pyridin-3-yl]-1H-indole-2-carboxylic acid ethyl ester Synthesized in an analogous manner to example 30, 50 mg, 45% LC/MS ESI m/z (M+H)+=460.2.

EXAMPLE 62

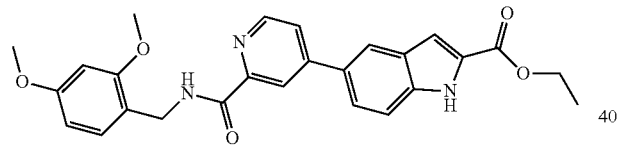

5-[2-(2,4-Dimethoxy-benzylcarbamoyl)-pyridin-4-yl]-1H-indole-2-carboxylic acid ethyl ester Synthesized in an analogous manner to example 30, 31 mg, 28% LC/MS ESI m/z (M+H)+=460.4.

EXAMPLE 63

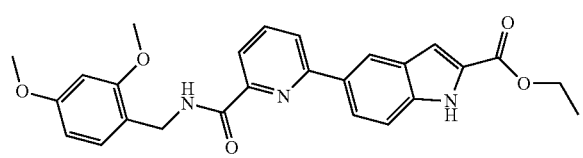 [SMILES: CCOC(=O)c1cc2cc(-c3cccc(C(=O)NCc4ccc(OC)cc4OC)n3)ccc2[nH]1]

5-[6-(2,4-Dimethoxy-benzylcarbamoyl)-pyridin-2-yl]-1H-indole-2-carboxylic acid ethyl ester Synthesized in an analogous manner to example 30, 20 mg, 18% LC/MS ESI m/z (M+H)+=460.2.

EXAMPLE 64

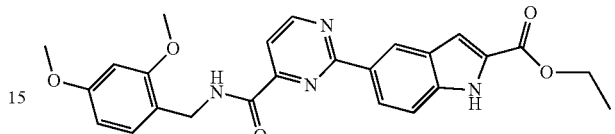

5-[4-(2,4-Dimethoxy-benzylcarbamoyl)-pyrimidin-2-yl]-1H-indole-2-carboxylic acid ethyl ester Synthesized in an analogous manner to example 30, 36 mg, 49% LC/MS ESI m/z (M+H)+=461.3.

EXAMPLE 65

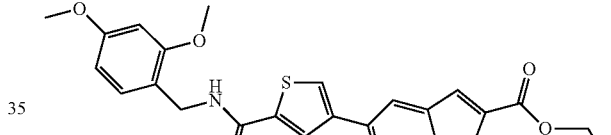

5-[5-(2,4-Dimethoxy-benzylcarbamoyl)-thiophen-3-yl]-1H-indole-2-carboxylic acid ethyl ester Synthesized in an analogous manner to example 30, 22 mg, 21% LC/MS ESI m/z (M+H)+=465.2.

EXAMPLE 66

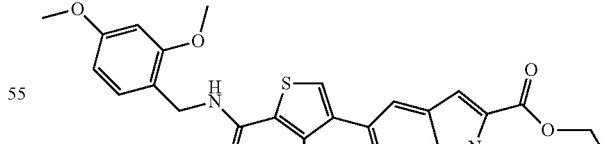

5-[5-(2,4-Dimethoxy-benzylcarbamoyl)-4-methyl-thiophen-3-yl]-1H-indole-2-carboxylic acid ethyl ester Synthesized in an analogous manner to example 30, 20 mg, 15% LC/MS ESI m/z (M+H)+=479.4.

EXAMPLE 67

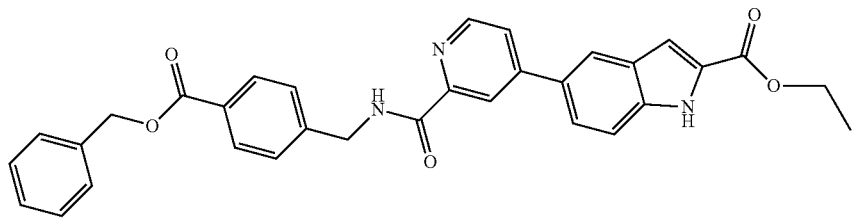 [SMILES: CCOC(=O)c1cc2cc(-c3ccnc(C(=O)NCc4ccc(C(=O)OCc5ccccc5)cc4)c3)ccc2[nH]1]

5-[2-(4-Benzyloxycarbonyl-benzylcarbamoyl)-pyridin-4-yl]-1H-indole-2-carboxylic acid ethyl ester Synthesized in an analogous manner to example 30, 62 mg, 31% LC/MS ESI m/z (M+H)+=534.4.

EXAMPLE 68

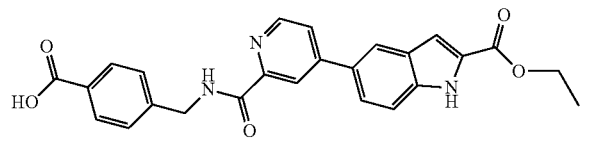 [SMILES: CCOC(=O)c1cc2cc(-c3ccnc(C(=O)NCc4ccc(C(=O)O)cc4)c3)ccc2[nH]1]

5-[2-(4-Carboxy-benzylcarbamoyl)-pyridin-4-yl]-1H-indole-2-carboxylic acid ethyl ester Is made from 5-[2-(4-Benzyloxycarbonyl-benzylcarbamoyl)-pyridin-4-yl]-1H-indole-2-carboxylic acid ethyl ester 42 mg, 97%, LC/MS ESI m/z (M+H)+=444.4.

EXAMPLE 69

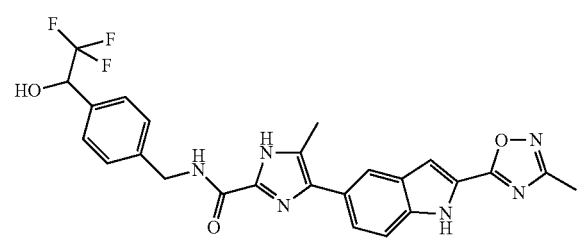 [SMILES: Cc1noc(-c2cc3cc(-c4nc(C(=O)NCc5ccc(C(O)C(F)(F)F)cc5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid 4-(2,2,2-trifluoro-1-hydroxy-ethyl)-benzylamide Synthesized in an analogous manner to example 30, 7 mg, 6% LC/MS ESI m/z (M+H)+=511.4.

EXAMPLE 70

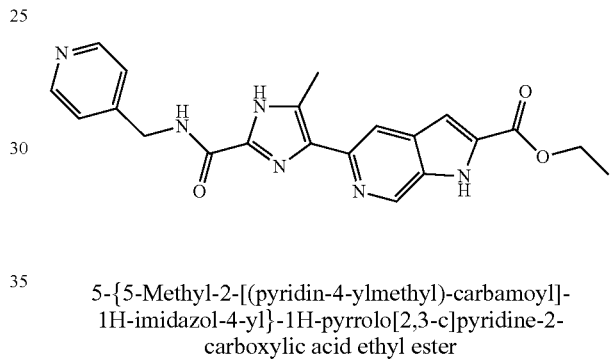

5-{5-Methyl-2-[(pyridin-4-ylmethyl)-carbamoyl]-1H-imidazol-4-yl}-1H-pyrrolo[2,3-c]pyridine-2-carboxylic acid ethyl ester Step 1:

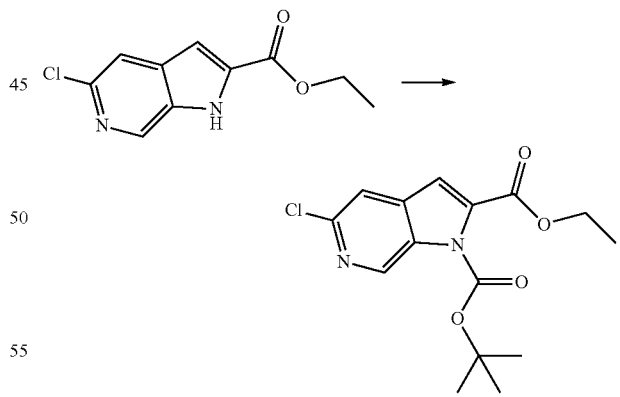

5-Chloro-1H-pyrrolo[2,3-c]picolinic acid ethyl ester (1.1 g, 4.9 mmol, WO2004104001) is dissolved in 26 ml of acetonitrile, and di-tert-butyldicarbonate (1.0 g, 4.9 mmol) is added to the solution. The reaction is stirred for 5 minutes, and then 1 mg of N,N dimethylaminopyridine is added. The reaction is stirred overnight (16 hours) and then the volatiles evaporated in vacuo. The resulting oil is taken up in ethyl acetate (200 ml), and washed with water (2×), 10% aqueous citric acid, and brine. The organic layer is dried (sodium sulfate), filtered and evaporated in vacuo to give the title compound that is used without further purification 1.6 g, 95%.

Step 2:

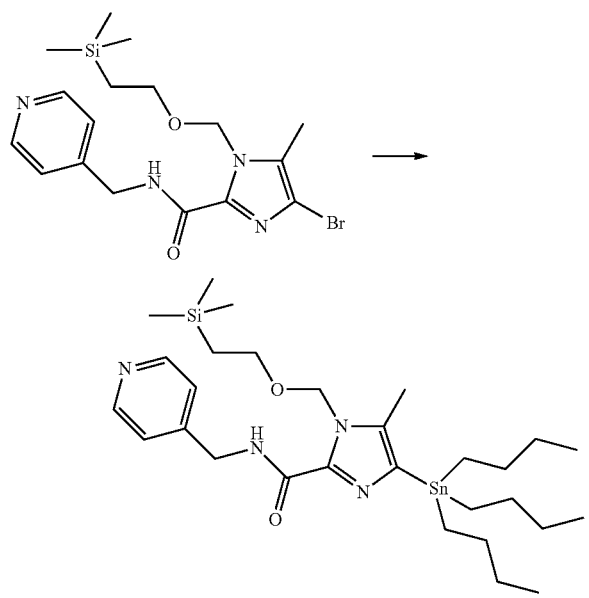

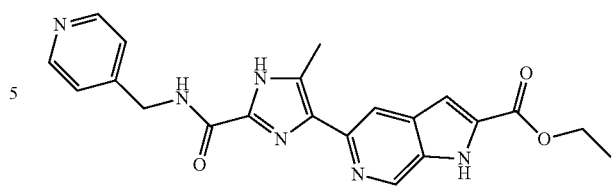

A flask is charged with 5-Bromo-indole-1,2-dicarboxylic acid 1-tert-butyl ester 2-ethyl ester (40 mg, 0.12 mmol) and 5-Methyl-4-tributylstannanyl-1-(2-trimethylsilanyl-ethoxymethyl)-1H-imidazole-2-carboxylic acid(pyridin-4-ylmethyl)-amide (78 mg, 0.12 mmol) and 2 ml of o-xylene. The solution is purged with nitrogen for 5 minutes, and $Pd(Cl_2)(PPh_3)_2$ is added to the reaction. The reaction vessel is sealed and heated at 100° C. for 24 hours. The reaction is cooled to room temperature, and the solvents evaporated in vacuo. The resulting oil is dissolved in 2 mL of dichloromethane, and 1 mL of trifluoroacetic acid is added. After 2 hours, reaction is evaporated in vacuo and the resulting oil purified on reverse-phase LC to give the title compound (9 mg, 18%) LC/MS ESI m/z (M+H)+=405.1.

A flask is charged with 4-Bromo-5-methyl-1-(2-trimethylsilanyl-ethoxymethyl)-1H-imidazole-2-carboxylic acid(pyridin-4-ylmethyl)-amide (1.4 g, 3.4 mmol, synthesized in an analogous manner to example 30), and dry THF (16 ml) is added. The flask is sealed, purged with nitrogen and cooled to −78° C. in a dry ice/acetone bath. Methyl lithium (2.1 ml, 1.6 M in THF) is added dropwise to the reaction over 5 minutes, and the resulting suspension stirred at −78° C. for 5 minutes. n-Butyl lithium (2.1 ml, 1.6 M in hexanes) is added to the solution, and the resulting red solution is stirred for 10 minutes at −78° C. after which tributyltin chloride (1.01 ml, 3.8 mmoL) is added to the reaction. The reaction is stirred at −78° C. for 1 hour, and is quenched by the addition of saturated aqueous ammonium chloride. The reaction is warmed to room temperature, poured into brine, and extracted with ethyl acetate. The combined organic washings are dried (sodium sulfate), filtered and evaporated in vacuo to give an oil that is purified on silica hexanes/ethyl acetate to give the title compound as a clear oil, 876 mg, 46% LC/MS ESI m/z (M+H)+=637.1.

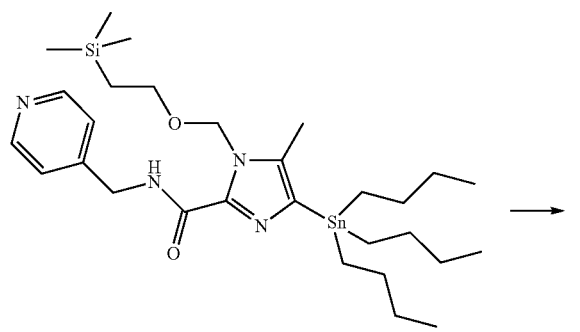

EXAMPLE 71

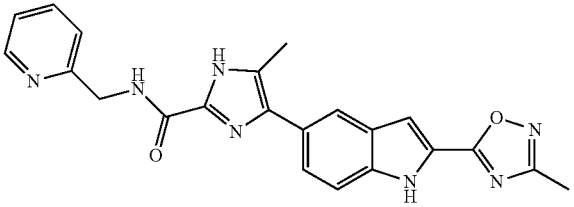 [SMILES: Cc1noc(-c2cc3cc(-c4nc(C(=O)NCc5ccccn5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid(pyridin-2-ylmethyl)-amide Synthesized in an analogous manner to example 30, 5 mg, 5% LC/MS ESI m/z (M+H)+=414.9.

EXAMPLE 72

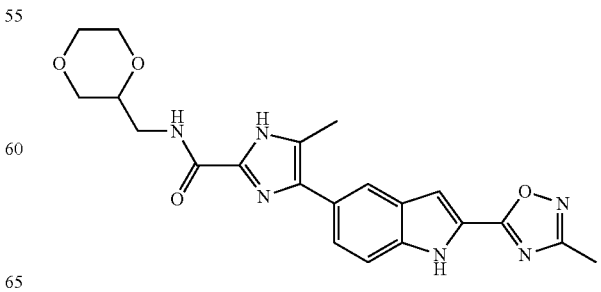

5-Methyl-4-[2-(3-methyl-1,2,4-oxadiazol-5-yl)-1H-indol-5-yl]-1H-imidazole-2-carboxylic acid(1,4-dioxinan-2-ylmethyl)-amide Synthesized in an analogous manner to example 30, 5 mg, 5% LC/MS ESI m/z (M+H)+=423.3.

EXAMPLE 73

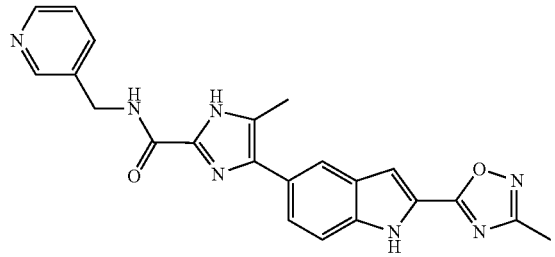 [SMILES: Cc1noc(-c2cc3cc(-c4nc(C(=O)NCc5cccnc5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid(pyridin-3-ylmethyl)-amide Synthesized in an analogous manner to example 30, 3 mg, 3% LC/MS ESI m/z (M+H)+=415.0.

EXAMPLE 74

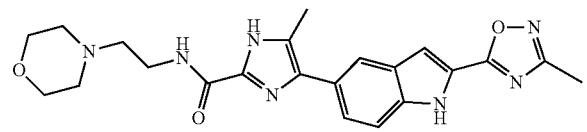 [SMILES: Cc1noc(-c2cc3cc(-c4nc(C(=O)NCCN5CCOCC5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid(2-morpholin-4-yl-ethyl)-amide Synthesized in an analogous manner to example 26, 8 mg, 12% LC/MS ESI m/z (M+H)+=436.52.

EXAMPLE 75

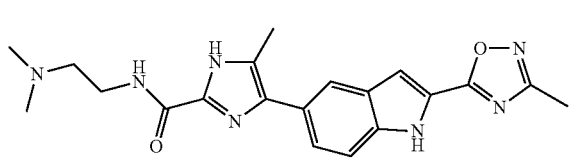

5-Methyl-4-[2-(3-methyl-1,2,4-oxadiazol-5-yl)-1H-indol-5-yl]-1H-imidazole-2-carboxylic acid(2-dimethylamino-ethyl)-amide Synthesized in an analogous manner to example 26, 14 mg, 23% LC/MS ESI m/z (M+H)+394.47.

EXAMPLE 76

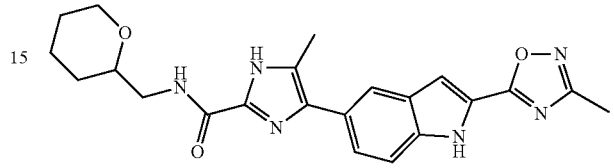

5-Methyl-4-[2-(3-methyl-1,2,4-oxadiazol-5-yl)-1H-indol-5-yl]-1H-imidazole-2-carboxylic acid(tetrahydro-pyran-2-ylmethyl)-amide Synthesized in an analogous manner to example 26, 18 mg, 19% LC/MS ESI m/z (M+H)+421.52.

EXAMPLE 77

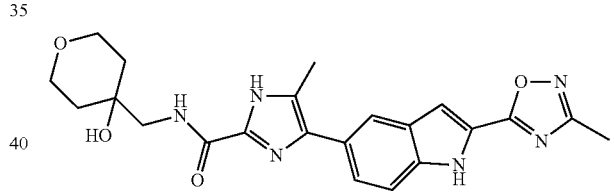

5-Methyl-4-[2-(3-methyl-1,2,4-oxadiazol-5-yl)-1H-indol-5-yl]-1H-imidazole-2-carboxylic acid(4-hydroxy-tetrahydro-pyran-4-ylmethyl)-amide Synthesized in an analogous manner to example 26, 14 mg, 21% LC/MS ESI m/z (M+H)+=437.49.

EXAMPLE 78

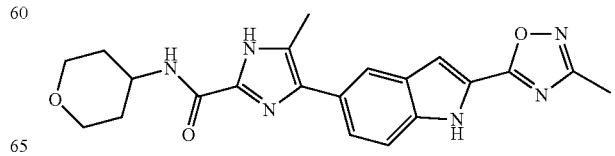

5-Methyl-4-[2-(3-methyl-1,2,4-oxadiazol-5-yl)-1H-indol-5-yl]-1H-imidazole-2-carboxylic acid(tetrahydro-pyran-4-yl)-amide Synthesized in an analogous manner to example 26, 4 mg, 6% LC/MS ESI m/z (M+H)+=407.51.

EXAMPLE 79

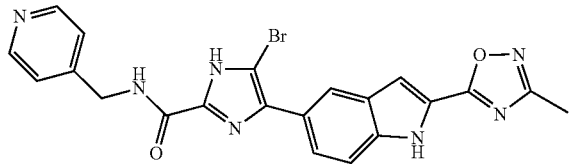 [SMILES: Cc1noc(-c2cc3cc(-c4nc(C(=O)NCc5ccncc5)[nH]c4Br)ccc3[nH]2)n1]

5-Bromo-4-[2-(3-methyl-1,2,4-oxadiazol-5-yl)-1H-indol-5-yl]-1H-imidazole-2-carboxylic acid(pyridin-4-ylmethyl)-amide Step 1:

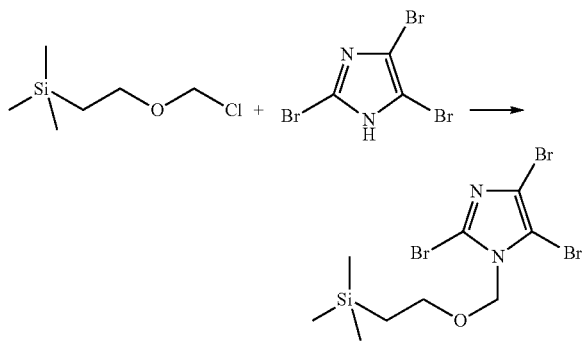

To a solution of 2,4,5-tribromo-1H-imidazole (10.3 g, 32 8 mmol) in anhydrous N,N-dimethylformamide (100 ml) is slowly added NaH (1.4 g, 36.1 mmol, 60% in mineral oil) at room temperature. The suspension is stirred for 15 minutes and 2-(Trimethylsilyl)ethoxymethyl chloride (5.8 ml, 32.8 mmol) is added. The mixture is stirred at room temperature for 3 hours. The reaction mixture is diluted with water (250 ml) and extracted with ethyl acetate (3×50 ml). The combined organic layer is washed with water (50 ml), brine, dried over MgSO₄, filtered, and concentrated in vacuo to yield 2,4,5-tribromo-1-(2-trimethylsilanyl-ethoxymethyl)-1H-imidazole as a yellow waxy solid 13.8 g, 97%.

Step 2:

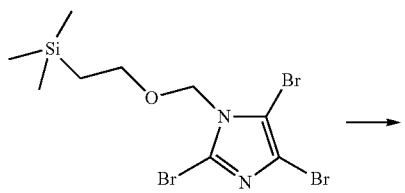

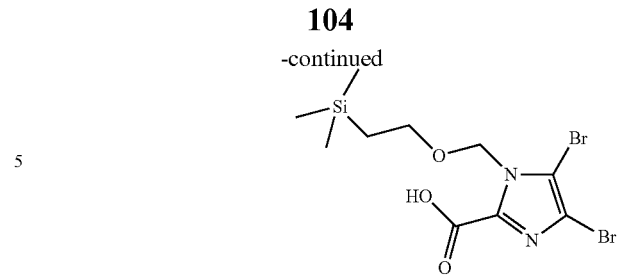

To a solution of 2,4,5-tribromo-1-(2-trimethylsilanyl-ethoxymethyl)-1H-imidazole (5.0 g, 11.5 mmol) in tetrahydrofuran (200 ml) at −78° C. is added phenyl lithium (7.0 ml, 12.6 mmol, 1.8 M in THF). After 30 minutes stirring at −78° C. $CO_2$-pellets (~3.0 g) are added. The mixture is allowed to warm to room temperature, water is added, and the pH is carefully adjusted with 6N HCl (aqueous) to pH=5. The mixture is extracted with ethyl acetate (2×50 ml) and the combined organic layer is washed with brine, dried over MgSO₄, filtered and evaporated in vacuo. The crude 4,5-dibromo-1-(2-trimethylsilanyl-ethoxymethyl)-1H-imidazole-2-carboxylic acid is obtained as a yellow oil, and used without further purification 4.2 g, 91%, LC/MS ESI m/z (M−H)− 398.8.

Step 3:

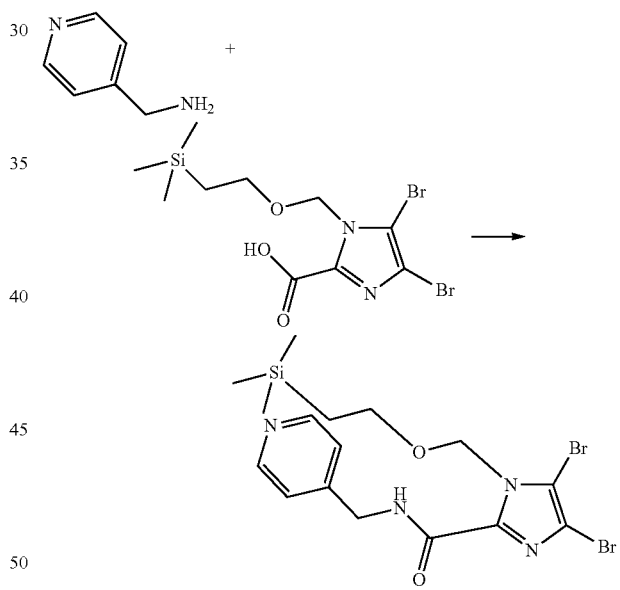

To a solution of 4,5-dibromo-1-(2-trimethylsilanyl-ethoxymethyl)-1H-imidazole-2-carboxylic acid (2.0 g, 4.5 mmol) in N,N dimethylformamide (20 ml) is subsequently added 2-(1H-7-Azabenzotriazol-1-yl)-1,1,3,3-tetramethyl uronium hexafluorophosphate Methanaminium (2.6 g, 6.7 mmol), 1-Hydroxy-7-Azabenzotriazole (153 mg, 1.1 mmol), N,N-diisopropylethylamine, (1.6 ml, 8.9 mmol), and pyridin-4-yl-methylamine (0.68 ml, 6.7 mmol). The mixture is stirred for 4 hours. Water (25 ml) is added and the mixture extracted with ethyl acetate (2×25 ml). The organic layer is washed with brine, dried over MgSO₄, filtered, and the solvent is evaporated. The brown residue is purified on silica with hexanes/ethyl acetate as the eluent 280 mg, 13%, LC/MS ESI m/z (M+H)+=491.30.

Step 4:

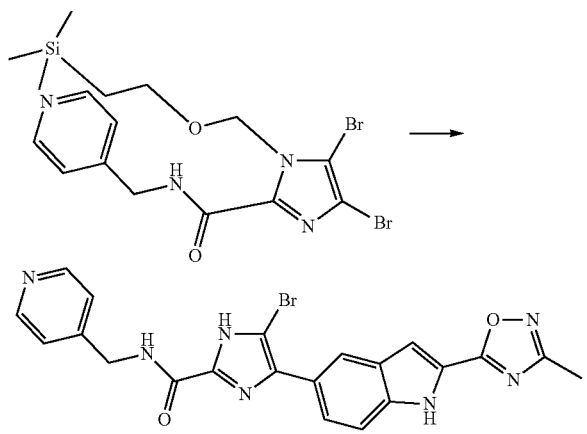

To a solution of 4,5-dibromo-1-(2-trimethylsilanyl-ethoxymethyl)-1H-imidazole-2-carboxylic acid(pyridin-4-ylmethyl)-amide (280 mg, 0.57 mmol) and 2-(3-methyl-1,2,4-oxadiazol-5-yl)-5-(4,4,5,5-tetramethyl-1,3,2-dioxaborolan-2-yl)-indole-1-carboxylic acid tert-butyl ester (243 mg, 0.57 mmol) in toluene (5.0 ml) is added aqueous Na$_2$CO$_3$ solution (2M, 0.63 ml, 1.26 mmol). The mixture is purged with argon for 10 minutes. (Bis(di-t-butyl(4-dimethy-laminutesophenyephosphine)dichloropalladium(II) (81 mg, 0.11 mmol) is added and the reaction mixture is sealed in a sealed tube and heated to 120° C. for 14 hours. The reaction mixture is diluted with ethyl acetate (25 ml), washed with water (15 ml), brine (15 ml), dried over MgSO$_4$, filtered, and concentrated in vacuo. The crude material is purified on reversed phase HPLC. The resulting protected analog is dissolved in 50% trifluoroacetic acid in dichloromethane (10 ml). After 2 hours the solvent is evaporated in vacuo, and the product is purified by reverse phase HPLC, 25 mg, 9%, LC/MS ESI m/z (M+H)+=480.33.

EXAMPLE 80

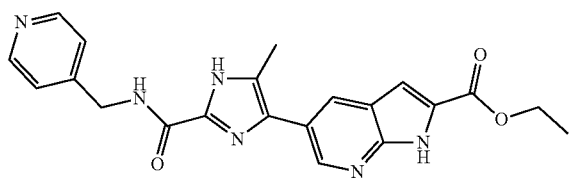 [SMILES: CCOC(=O)c1cc2cc(-c3nc(C(=O)NCc4ccncc4)[nH]c3C)cnc2[nH]1]

5-{5-Methyl-2-[(pyridin-4-ylmethyl)-carbamoyl]-3H-imidazol-4-yl}-1H-pyrrolo[2,3-b]pyridine-2-carboxylic acid ethyl ester Step 1

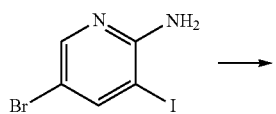

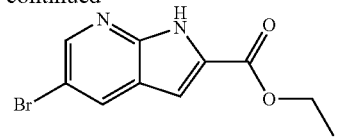

To a solution of 5-Bromo-3-iodo-pyridin-2-ylamine (US2006/183758 and US200559744) in anhydrous N,N dimethylforamide (86 mL) under argon is added pyruvic acid (3.67 g, 41.65 mmol), 1,4-diazabicyclo[2.2.2]octane (4.67 g, 41.65 mmol) and Pd(OAc)$_2$ (314 mg, 1.4 mmol). The mixture is sealed, purged under argon and heated in oil bath to 110° C. for 4 hours. The reaction is cooled to room temperature, and filtered. The filtrate is evaporated in vacuo, the crude residue suspended in toluene (50 ml), and concentrated down to give crude acid. The acid is suspended in ethanol (100 ml) and HCl gas is bubbled though the reaction mixture for 5 minutes, and the reaction mixture is heated to 65° C. for 16 hours. The mixture is cooled to room temperature and evaporated in vacuo. The residue is taken up in ethyl acetate, and neutralized with saturated aqueous NaHCO$_3$, and filtered. The filtrate is extracted three times with ethyl acetate, and washed with water and Brine. The combined organics are dried over MgSO$_4$, filtered, and concentrated in vacuo to give a crude material that is purified on silica with hexanes/ethyl acetate as the eluent to give the title compound 5-Bromo-1H-pyrrolo[2,3-b]pyridine-2-carboxylic acid ethyl ester as a yellow solid 640 mg, 17%, LC/MS ESI m/z (M+H)+=269.59.

Step 2

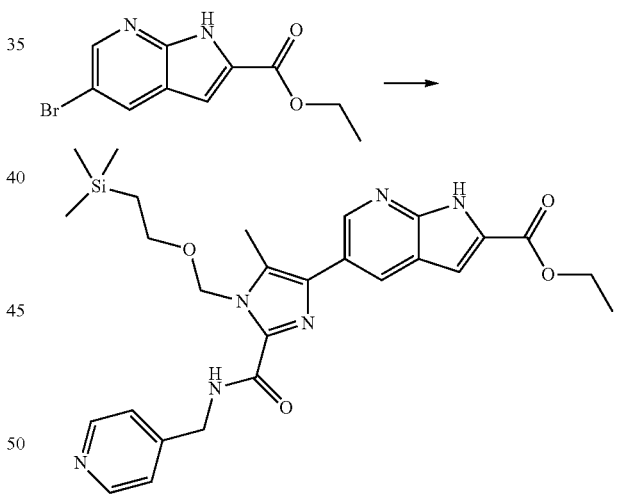

A mixture of 5-Bromo-1H-pyrrolo[2,3-b]pyridine-2-carboxylic acid ethyl ester (143 mg, 0.53 mmol), bis(pinacolato) diboron (202 mg, 0.79 mmol), tricyclohexylphosphine (15 mg, 0.053 mmol), potassium acetate (105 mg, 1.07 mmol) and Pd(dba)$_2$ (15 mg, 0.027 mmol) in 1,4-dioxane (5 ml) is heated to 110° C. in an oil bath for 1 hour under argon. 4-Bromo-5-methyl-1-(2-trimethylsilanyl-ethoxymethyl)-1H-imidazole-2-carboxylic acid(pyridin-4-ylmethyl)-amide (225 mg, 0.53 mmol) and (Bis(di-t-butyl(4-dimethylaminophenyl)phosphine)dichloropalladium(II) (38 mg, 0.053 mmol) and aqueous Na$_2$CO$_3$ (2M, 1.33 ml, 2.65 mmol) are added, and the reaction mixture is heated at 110° C. for 1 hour. The mixture is cooled to room temperature, diluted with 5% methanol/dichloromethane and filtered through celite. The filtrate is evaporated in vacuo, and the crude product is purified by reverse phase HPLC to give the title compound 5-[5-Methyl-2-[(pyridin-4-ylmethyl)-carbamoyl]-1-(2-trimethyl-silanyl-ethoxymethyl)-1H-imidazol-4-yl]-1H-pyrrolo[2,3-b]pyridine-2-carboxylic acid ethyl ester as a light yellow solid 150 mg, 53%, LC/MS ESI m/z (M+H)+=535.61.

Step 3

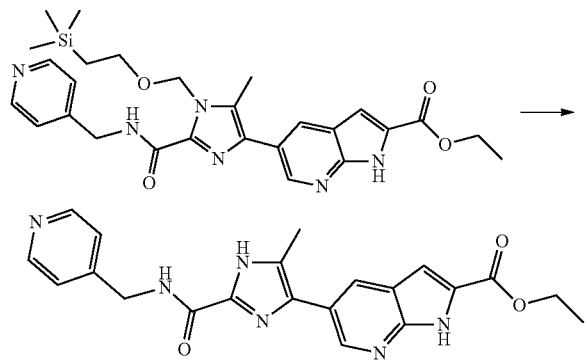

5-[5-Methyl-2-[(pyridin-4-ylmethyl)-carbamoyl]-1-(2-tri-methylsilanyl-ethoxymethyl)-1H-imidazol-4-yl]-1H-pyrrolo[2,3-b]pyridine-2-carboxylic acid ethyl ester (45 mg, 0.084 mmol) is stirred in trilfuoroacetic acid/dichloromethane (1 ml/500 uL) for 3 hours. The solvent is evaporated in vacuo and the crude oil is suspended in toluene and concentrated down to provide the title compound 5-{5-Methyl-2-[(pyridin-4-ylmethyl)-carbamoyl]-3H-imidazol-4-yl}-1H-pyrrolo[2,3-b]pyridine-2-carboxylic acid ethyl ester as a TFA salt (43 mg, 80%), LC/MS ESI m/z (M+H)+=405.61.

EXAMPLE 81

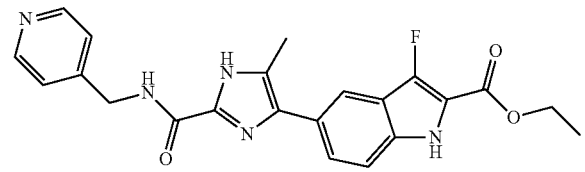 [SMILES: CCOC(=O)c1[nH]c2ccc(-c3nc(C(=O)NCc4ccncc4)[nH]c3C)cc2c1F]

3-Fluoro-5-{5-methyl-2-[(pyridin-4-ylmethyl)-carbamoyl]-3H-imidazol-4-yl}-1H-indole-2-carboxylic acid ethyl ester Step 1:

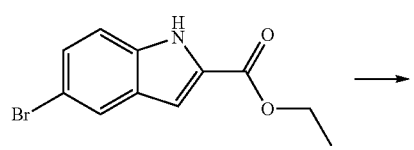

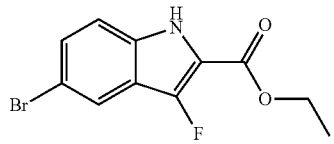

A mixture of 5-Bromo-1H-indole-2-carboxylic acid ethyl ester (50 mg, 0.186 mmol) and 1-fluoro-2,4,6-trimethylpyridinium triflate (204 mg, 0.60 mmol) are dissolved in tetrachloroethane (1 ml) and heated to 100° C. for 30 minutes. The reaction is diluted with ethyl acetate washed with water and brine. The organic layer is dried (sodium sulfate), filtered and concentrated in vacuo to give an oil that is purified by reverse phase HPLC to give the title compound as a white solid 27 mg, 50%, LC/MS ESI m/z (M+H)+=286.31.

Step 2.

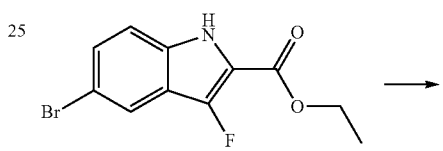

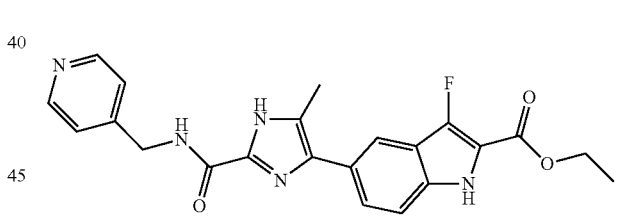

3-Fluoro-5-{5-methyl-2-[(pyridin-4-ylmethyl)-carbamoyl]-3H-imidazol-4-yl}-1H-indole-2-carboxylic acid ethyl ester is prepared 8 mg, 66%, LC/MS ESI m/z (M+H)+=422.50 the procedure reported above example 80.

EXAMPLE 82

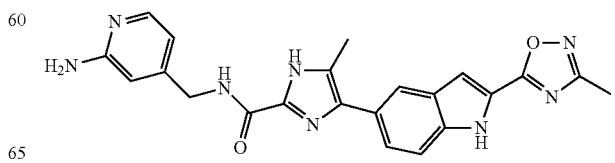

4-Methyl-5-[2-(3-methyl-[1,2,4]oxadiazol-5-yl)-1H-indol-5-yl]-1H-imidazole-2-carboxylic acid(2-amino-pyridin-4-ylmethyl)-amide Synthesized in an analogous manner to example 26, 28 mg, 37%, LC/MS ESI m/z (M+H)+=429.43.

EXAMPLE 83

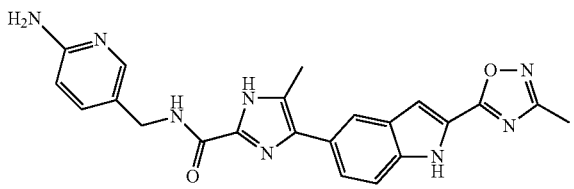 [SMILES: Cc1noc(-c2cc3cc(-c4nc(C(=O)NCc5ccc(N)nc5)[nH]c4C)ccc3[nH]2)n1]

4-Methyl-5-[2-(3-methyl-[1,2,4]oxadiazol-5-yl)-1H-indol-5-yl]-1H-imidazole-2-carboxylic acid(6-amino-pyridin-3-ylmethyl)-amide Synthesized in an analogous manner to example 26, 51 mg, 54%, LC/MS ESI m/z (M+H)+=429.43.

EXAMPLE 84

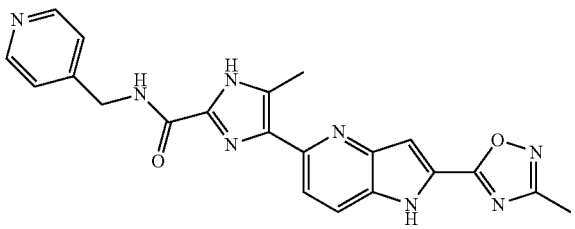 [SMILES: Cc1noc(-c2cc3nc(-c4nc(C(=O)NCc5ccncc5)[nH]c4C)ccc3[nH]2)n1]

5-Methyl-4-[2-(3-methyl-1,2,4-oxadiazol-5-yl)-1H-pyrrolo[3,2-b]pyridin-5-yl]-1H-imidazole-2-carboxylic acid(pyridin-4-ylmethyl)-amide Step 1:

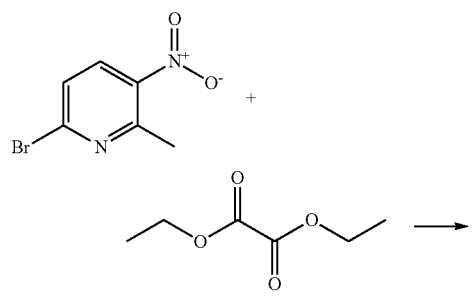

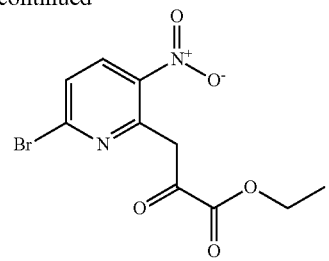

To a solution of potassium ethoxide (1.1 g, 12.7 mmol) in diethylether/ethanol (5:1, 100 ml) is added oxalic acid diethyl ester (1.7 ml, 12 7 mmol) in one portion, and the resulting solution is stirred at room temperature for 30 minutes. 6-Bromo-2-methyl-3-nitro-pyridine (2.5 g, 11 5 mmol) is added as a suspension in diethylether (30 ml) and the reaction is stirred for 16 hours at room temperature. The precipitate is filtered off and washed with cold diethylether. The precipitate is dissolved in glacial acetic acid and then the solvent is evaporated in vacuo to give the product as a brown solid 500 mg, 14% LC/MS ESI m/z (M+H)+=317.2.

Step 2:

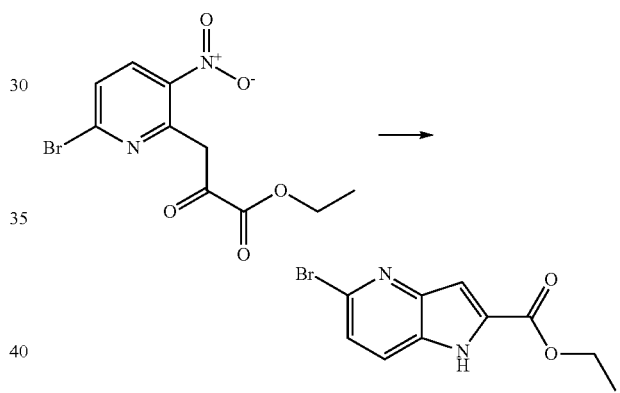

To a solution of 3-(6-bromo-3-nitro-pyridin-2-yl)-2-oxo-propionic acid ethyl ester (500 mg, 1.6 mmol) in tetrahydrofuran (16 mL) and ethanol (8 ml) is added saturated aqueous NH4Cl solution (8 ml). The resulting solution is vigorously stirred at room temperature for 30 minutes. Iron powder (528 mg, 9.5 mmol) is added portionwise, and the suspension is heated to reflux for 2 hours. After cooling, the mixture is filtrated through a celite plug, and washed with warm tetrahydrofuran. The filtrate is concentrated in vacuo to give an aqueous suspension, that is extracted with dichloromethane (200 ml). The organic layer is washed with water, brine, and dried over Na2SO4. After the solvent is filtrated and evaporated, the crude product is purified on silica with hexanes/ethyl acetate as the eluent to give the product as a white solid 295 mg, 70%, LC/MS ESI m/z (M+H)+=269.3.

Step 3:

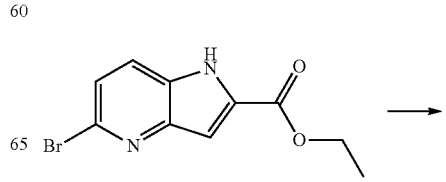

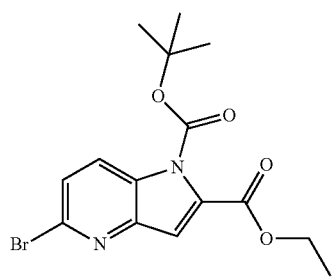

Synthesized in an analogous manner to example 21, step 4, 262 mg, 100% LC/MS ESI m/z (M+H)+=371.3.

Step 4:

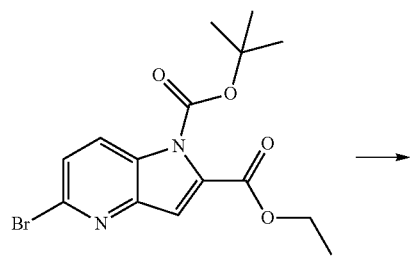

To a solution of 5-bromo-pyrrolo[3,2-b]pyridine-1,2-dicarboxylic acid 1-tert-butyl ester 2-ethyl ester (240 mg, 0.65 mmol) in 1,4-dioxane (5 ml) is added bis(pinacolato)diboron (198 mg, 0.78 mmol), tricyclohexylphosphine (18.2 mg, 0.065 mmol), potassium acetate (115 mg, 1.2 mmol) and bis(dibenzylideneacetone) palladium (19 mg, 0.033 mmol). The mixture is purged with argon and heated to 110° C. for 1 hour. The reaction mixture is used directly in the next step.

Step 5:

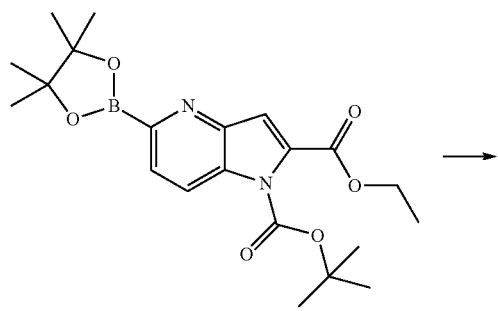

To the reaction mixture from step 4 is added 4-bromo-5-methyl-1-(2-trimethylsilanyl-ethoxymethyl)-1H-imidazole-2-carboxylic acid(pyridin-4-ylmethyl)-amide (270 mg, 0.64 mmol), (bis(di-t-butyl(4-dimethylaminutesophenyephosphine)dichloropalladium(II) (45 mg, 0.063 mmol) and aqueous, $Na_2CO_3$ (2M, 635 µL, 1.27 mmol). The resulting mixture is purged with argon for 10 minutes, and the reaction is stirred at 110° C. for 4 hours. The reaction is cooled to room temperature and diluted with ethyl acetate. The solution is washed with water and brine, dried over $Na_2SO_4$, filtrated, and evaporated in vacuo. The crude product is purified by prep-TLC with hexanes/ethyl acetate to give the product as a white solid, 65 mg, 16%, LC/MS ESI m/z (M+H)+=635.6.

Step 6:

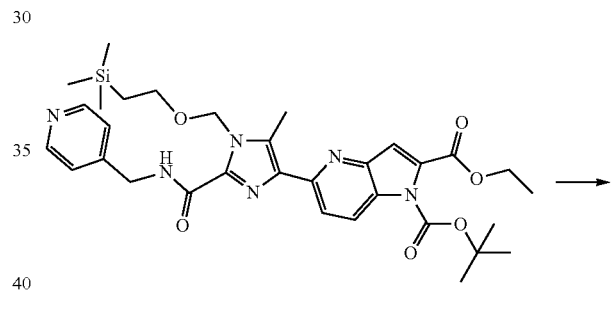

5-[5-Methyl-2-[(pyridin-4-ylmethyl)-carbamoyl]-1-(2-trimethylsilanyl-ethoxymethyl)-1H-imidazol-4-yl]-pyrrolo[3,2-b]pyridine-1,2-dicarboxylic acid 1-tert-butyl ester 2-ethyl ester (40 mg, 0.065 mmol) in tetrahydrofuran/methanol (1:1, 0.5 ml) is added aqueous NaOH (2N 47 µL, 0.09 mmol). The reaction is stirred at room temperature for 12 hours, and the solvent is evaporated in vacuo. The residue is neutralized with citric acid to pH ~5 and the product is extracted with dichloromethane (10 ml). The organic layer is washed with water, brine, and dried over $Na_2SO_4$. The solution is filtered and evaporated in vacuo to give the product as a white solid 35 mg, 100%, LC/MS ESI m/z (M+H)+=507.5.

Step 7:

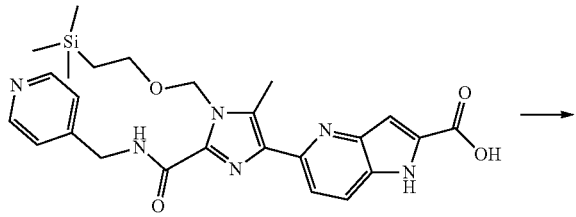

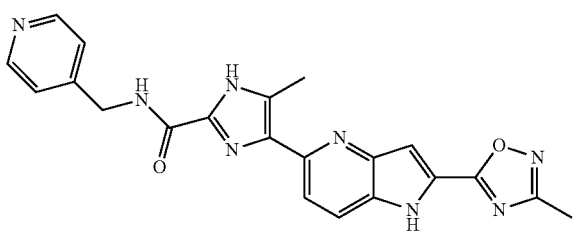

Synthesized in an analogous manner to example 21, 6 mg, 37% LC/MS ESI m/z (M+H)+=415.4.

EXAMPLE 85

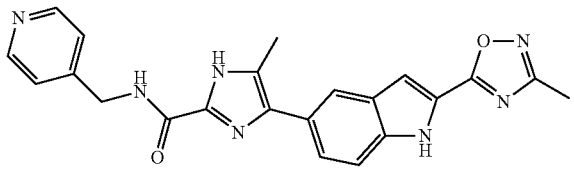 [SMILES: Cc1noc(-c2cc3cc(-c4nc(C(=O)NCc5ccncc5)[nH]c4C)ccc3[nH]2)n1]

5-Methyl-4-[2-(3-methyl-1,2,4-oxadiazol-5-yl)-1H-indol-5-yl]-1H-imidazole-2-carboxylic acid 4-pyridylmethyl amide Step 1:

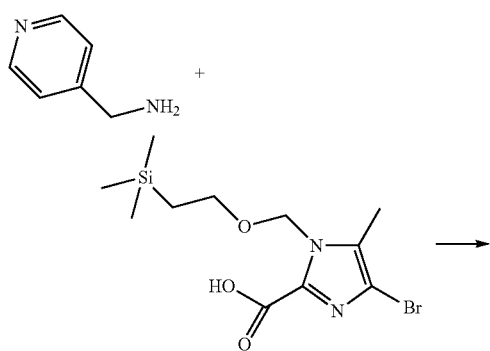

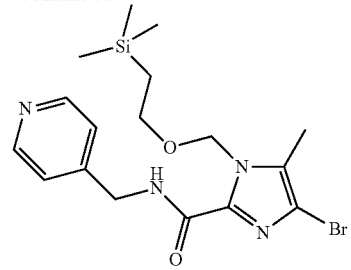

To a solution of 4-Bromo-5-methyl-1-(2-trimethylsilanyl-ethoxymethyl)-1H-imidazole-2-carboxylic acid (13.5 g, 40.3 mmol), in N,N-dimethylformamide (100 ml) is added HATU (22 g, 57.9 mmol), 1-Hydroxy-7-Azabenzotriazole (1 g, 7.35 mmol), and N,N-diisopropylethylamine, (15 ml, 81.4 mmol). The reaction mixture is stirred for 0.5 hour before aminomethylpyridine (5.4 ml, 49.9 mmol) is added. The reaction mixture is stirred at room temperature for 14 hours, then diluted with ethyl acetate (300 ml), washed with water (60 ml), brine (2×65 ml), dried over Na$_2$SO$_4$, filtered, and concentrated in vacuo. The crude product is purified on silica hexane/ethyl acetate as the eluent 11.8 g, 68.9%, LC/MS ESI m/z (M+H)=425.5.

Step 2:

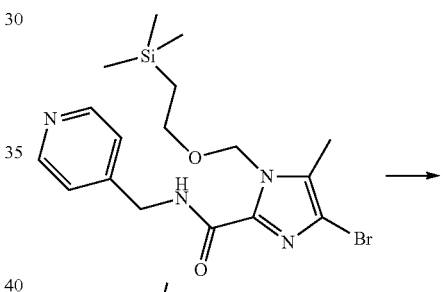

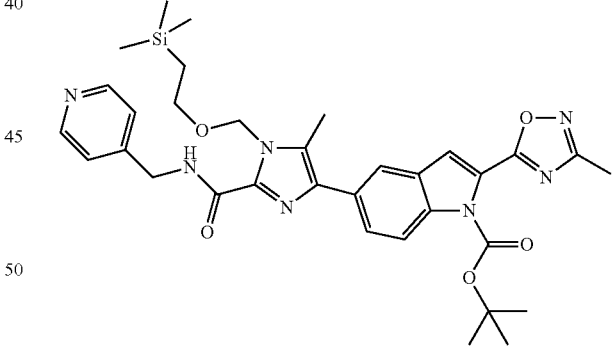

To a solution of 4-Bromo-5-methyl-1-(2-trimethylsilanyl-ethoxymethyl)-1H-imidazole-2-carboxylic acid 4-pyridylmethylamide (11.5 g, 27.0 mmol) and 2-(3-Methyl-1,2,4-oxadiazol-5-yl)-5-(4,4,5,5-tetramethyl-1,3,2-dioxaborolan-2-yl)-indole-1-carboxylic acid tert-butyl ester (15 g, 35.3 mmol) in toluene (170 ml) is added aqueous Na$_2$CO$_3$ (2M, 30 ml, 60.0 mmol). The mixture is purged with argon for 10 minutes and (Bis(di-t-butyl(4-dimethylaminophenyl)phosphine)dichloropalladium(II) (3.85 g, 5.43 mmol) is added and the reaction mixture is sealed in a seal tube and heated at 110° C. for 14 hours. The reaction mixture is diluted with ethyl acetate (500 ml), washed with water (100 ml), brine (2×100 ml), dried over Na$_2$SO$_4$, filtered, and concentrated in vacuo. The crude product is purified by on silica with hexanes ethyl acetate as the eluent 9.7 g, 55.7%, LC/MS ESI m/z (M+H)+=644.7.

Step 3:

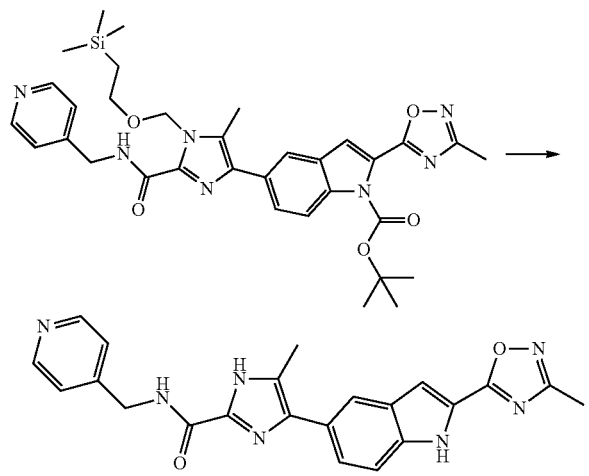

To a solution of 5-Methyl-4-[2-(3-methyl-1,2,4-oxadiazol-5-yl)-1H-indol-5-yl]-1-(2-trimethylsilanyl-ethoxymethyl)-1H-imidazole-2-carboxylic acid 4-pyridylmethyl amide (12.6 g, 19 6 mmoL) in ethanol (70 ml) is added aqueous HCl (6N 50 ml, 300 mmol). The mixture is heated at 100° C. for 7 hours. After cooling to room temperature, the resulting suspension is diluted with ice-cooled water (500 ml), basified with saturated aqueous NaHCO₃ (50 ml) and aqueous sodium hydroxide (5N, 46.5 ml) to pH 7-8. Diethylether is added, (50 ml) and suspension stirred for 30 minutes. The resulting suspension is filtered and the solids are washed with water (2×50 ml), ether (2×25 ml), dried at 60° C. in vacuo for 14 hours to give a solid that is triturated with 1:1 acetonitrile-ethanol (40 ml) to give the product 5.75 g, 80%, LC/MS ESI m/z (M+H)+= 414.5.

EXAMPLE 86

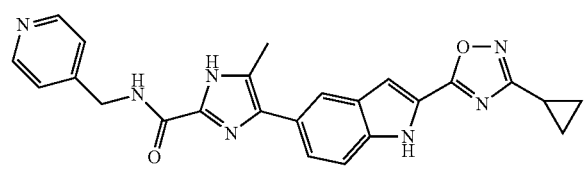 [SMILES: Cc1[nH]c(C(=O)NCc2ccncc2)nc1-c1ccc2[nH]c(-c3nc(C4CC4)no3)cc2c1]

4-[2-(3-Cyclopropyl-1,2,4-oxadiazol-5-yl)-1H-indol-5-yl]-5-methyl-1H-imidazole-2-carboxylic acid(pyridin-4-ylmethyl)-amide Step 1:

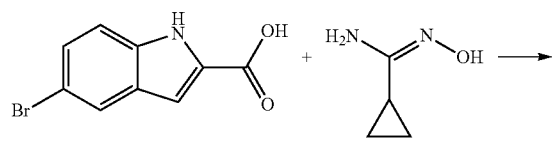

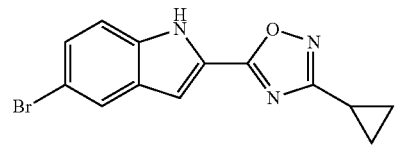

To a suspension of 5-bromo-1H-indole-2-carboxylic acid (300 mg, 1.25 mmol) in tetrahydrofuran (5 ml) is added carbonyl diimidazole (223 mg, 1.38 mmol) and the reaction is stirred vigorously at room temperature for 20 minutes. N-hydroxy-cyclopropane carboxamidine (223 mg, 1.38 mmol) is then added and the reaction is stirred for 1 hour at room temperature followed by 15 minutes at 150° C. in a microwave reactor. The reaction is diluted with ethyl acetate (200 ml) and washed with water and brine. The organic phase is dried over Na₂SO₄, filtrated, and evaporated in vacuo. The residue is purified on silica with hexanes ethyl acetate as the eluent to give the product as a white solid 33 mg, 88%, LC/MS ESI m/z (M+H)+=306.9.

Step 2:

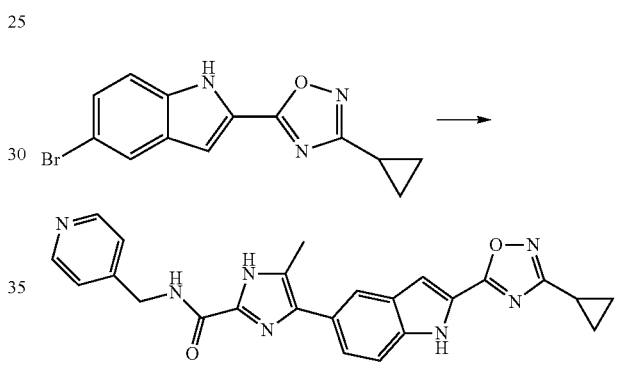

Synthesized in an analogous manner to example 20, step 3, example 26, step 3 and 6, 6 mg, 13% LC/MS ESI m/z (M+H)+= 440.2.

EXAMPLE 86

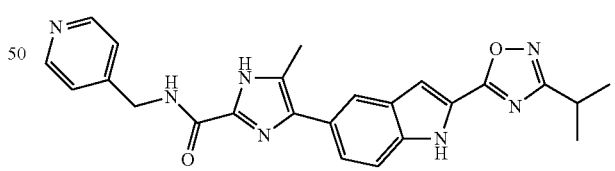

4-[2-(3-Isopropyl-1,2,4-oxadiazol-5-yl)-1H-indol-5-yl]-5-methyl-1H-imidazole-2-carboxylic acid(pyridin-4-ylmethyl)-amide Synthesized in an analogous manner to example 70, 20 mg, 10%, LC/MS ESI m/z (M+H)+=442.5.

The following compounds are made as shown in examples 26 and 25.

| Structure | LC/MS (M + H)+ | Name |
|---|---|---|
| 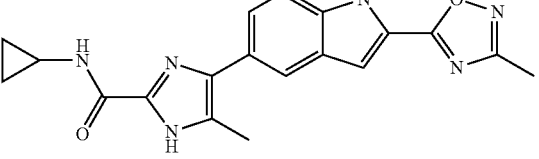 | 363.2 | N-cyclopropyl-5-methyl-4-[2-(3-methyl-1,2,4-oxadiazol-5-yl)-1H-indol-5-yl]-1H-imidazole-2-carboxamide |
| 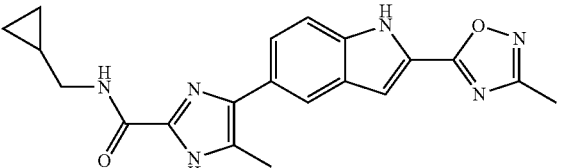 | 377.2 | N-(cyclopropylmethyl)-5-methyl-4-[2-(3-methyl-1,2,4-oxadiazol-5-yl)-1H-indol-5-yl]-1H-imidazole-2-carboxamide |
| 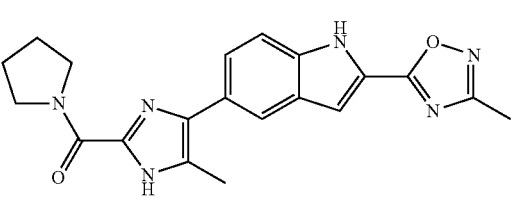 [SMILES: Cc1noc(-c2cc3cc(-c4nc(C(=O)N5CCCC5)[nH]c4C)ccc3[nH]2)n1] | 377.2 | {5-methyl-4-[2-(3-methyl-1,2,4-oxadiazol-5-yl)-1H-indol-5-yl]-1H-imidazol-2-yl}(pyrrolidin-1-yl)methanone |
| 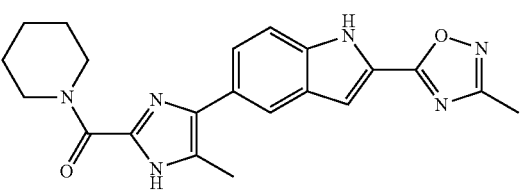 | 391.2 | {5-methyl-4-[2-(3-methyl-1,2,4-oxadiazol-5-yl)-1H-indol-5-yl]-1H-imidazol-2-yl}(piperidin-1-yl)methanone |
| 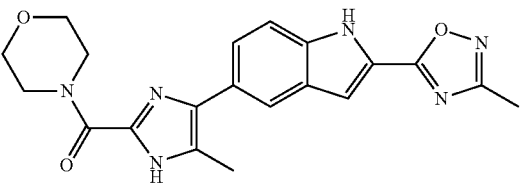 [SMILES: Cc1noc(-c2cc3cc(-c4nc(C(=O)N5CCOCC5)[nH]c4C)ccc3[nH]2)n1] | 393.2 | {5-methyl-4-[2-(3-methyl-1,2,4-oxadiazol-5-yl)-1H-indol-5-yl]-1H-imidazol-2-yl}(morpholin-4-yl)methanone |
| 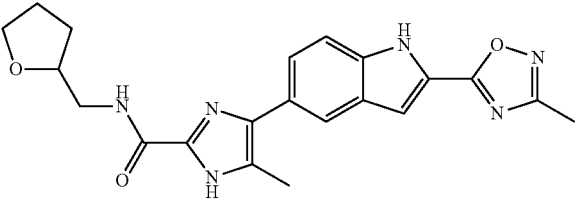 [SMILES: Cc1noc(-c2cc3cc(-c4nc(C(=O)NCC5CCCO5)[nH]c4C)ccc3[nH]2)n1] | 407.3 | 5-methyl-4-[2-(3-methyl-1,2,4-oxadiazol-5-yl)-1H-indol-5-yl]-N-(tetrahydrofuran-2-ylmethyl)-1H-imidazole-2-carboxamide |
| 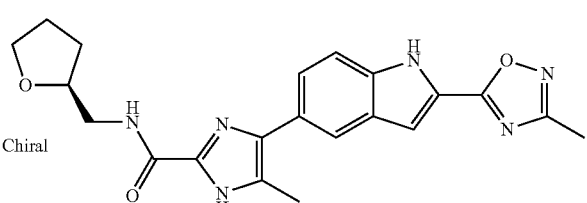 | 407.2 | 5-methyl-4-[2-(3-methyl-1,2,4-oxadiazol-5-yl)-1H-indol-5-yl]-N-[(2S)-tetrahydrofuran-2-ylmethyl]-1H-imidazole-2-carboxamide |
| 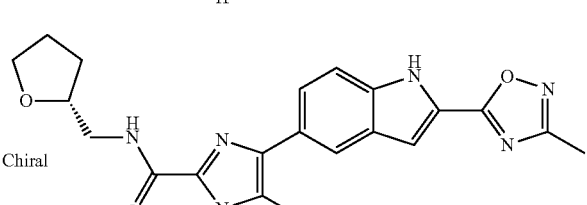 | 407.2 | 5-methyl-4-[2-(3-methyl-1,2,4-oxadiazol-5-yl)-1H-indol-5-yl]-N-[(2R)-tetrahydrofuran-2-ylmethyl]-1H-imidazole-2-carboxamide |

| Structure | LC/MS (M + H)+ | Name |
|---|---|---|
| 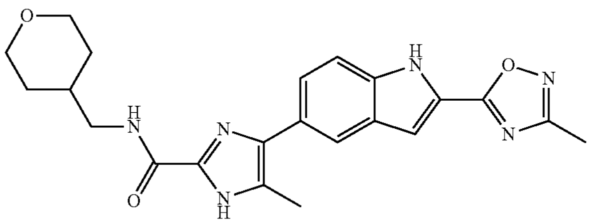 [SMILES: Cc1noc(-c2cc3cc(-c4nc(C(=O)NCC5CCOCC5)[nH]c4C)ccc3[nH]2)n1] | 421.2 | 5-methyl-4-[2-(3-methyl-1,2,4-oxadiazol-5-yl)-1H-indol-5-yl]-N-(tetrahydro-2H-pyran-4-ylmethyl)-1H-imidazole-2-carboxamide |
| 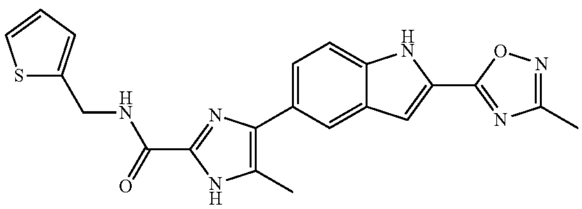 [SMILES: Cc1noc(-c2cc3cc(-c4nc(C(=O)NCc5cccs5)[nH]c4C)ccc3[nH]2)n1] | 419.2 | 5-methyl-4-[2-(3-methyl-1,2,4-oxadiazol-5-yl)-1H-indol-5-yl]-N-(thiophen-2-ylmethyl)-1H-imidazole-2-carboxamide |
| 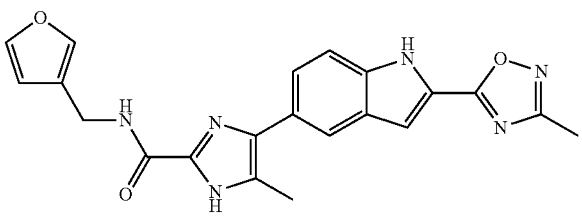 [SMILES: Cc1noc(-c2cc3cc(-c4nc(C(=O)NCc5ccoc5)[nH]c4C)ccc3[nH]2)n1] | 403.2 | N-(furan-3-ylmethyl)-5-methyl-4-[2-(3-methyl-1,2,4-oxadiazol-5-yl)-1H-indol-5-yl]-1H-imidazole-2-carboxamide |
| 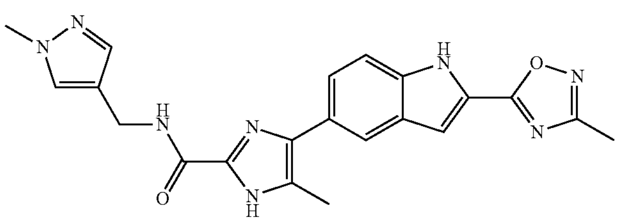 | 417.2 | 5-methyl-4-[2-(3-methyl-1,2,4-oxadiazol-5-yl)-1H-indol-5-yl]-N-[(1-methyl-1H-pyrazol-4-yl)methyl]-1H-imidazole-2-carboxamide |
| 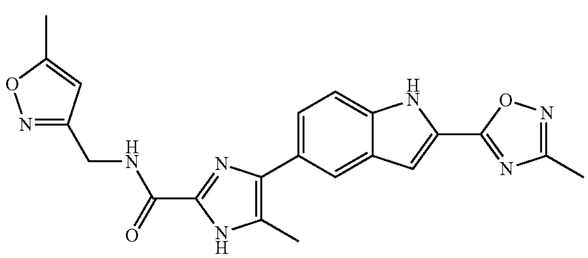 [SMILES: Cc1noc(-c2cc3cc(-c4nc(C(=O)NCc5cc(C)on5)[nH]c4C)ccc3[nH]2)n1] | 418.2 | 5-methyl-N-[(5-methylisoxazol-3-yl)methyl]-4-[2-(3-methyl-1,2,4-oxadiazol-5-yl)-1H-indol-5-yl]-1H-imidazole-2-carboxamide |
| 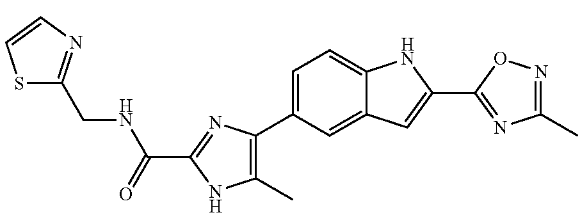 [SMILES: Cc1noc(-c2cc3cc(-c4nc(C(=O)NCc5nccs5)[nH]c4C)ccc3[nH]2)n1] | 420.3 | 5-methyl-4-[2-(3-methyl-1,2,4-oxadiazol-5-yl)-1H-indol-5-yl]-N-(1,3-thiazol-2-ylmethyl)-1H-imidazole-2-carboxamide |
| 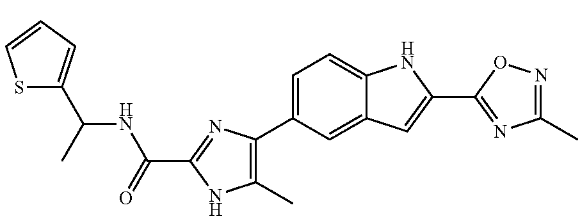 | 433.2 | 5-methyl-4-[2-(3-methyl-1,2,4-oxadiazol-5-yl)-1H-indol-5-yl]-N-[1-(thiophen-2-yl)ethyl]-1H-imidazole-2-carboxamide |

| Structure | LC/MS (M + H)+ | Name |
|---|---|---|
| 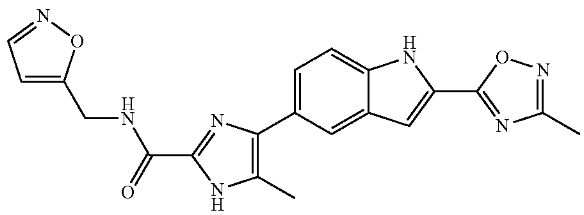 [SMILES: Cc1noc(-c2cc3cc(-c4nc(C(=O)NCc5ccno5)[nH]c4C)ccc3[nH]2)n1] | 404.2 | N-(isoxazol-5-ylmethyl)-5-methyl-4-[2-(3-methyl-1,2,4-oxadiazol-5-yl)-1H-indol-5-yl]-1H-imidazole-2-carboxamide |
| 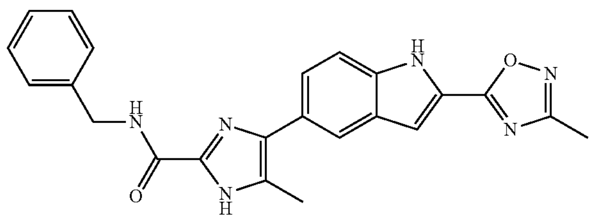 [SMILES: Cc1noc(-c2cc3cc(-c4nc(C(=O)NCc5ccccc5)[nH]c4C)ccc3[nH]2)n1] | 413.2 | N-benzyl-5-methyl-4-[2-(3-methyl-1,2,4-oxadiazol-5-yl)-1H-indol-5-yl]-1H-imidazole-2-carboxamide |
| 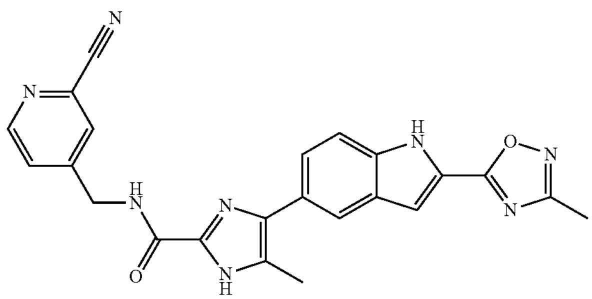 [SMILES: Cc1noc(-c2cc3cc(-c4nc(C(=O)NCc5ccnc(C#N)c5)[nH]c4C)ccc3[nH]2)n1] | 439.2 | N-[(2-cyanopyridin-4-yl)methyl]-5-methyl-4-[2-(3-methyl-1,2,4-oxadiazol-5-yl)-1H-indol-5-yl]-1H-imidazole-2-carboxamide |
| 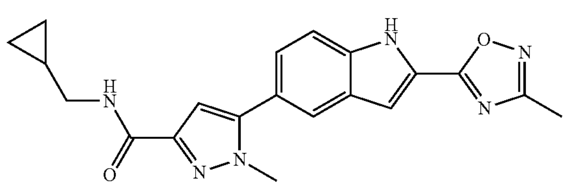 [SMILES: Cc1noc(-c2cc3cc(-c4cc(C(=O)NCC5CC5)nn4C)ccc3[nH]2)n1] | 377.2 | N-(cyclopropylmethyl)-1-methyl-5-[2-(3-methyl-1,2,4-oxadiazol-5-yl)-1H-indol-5-yl]-1H-pyrazole-3-carboxamide |
| | 407.2 | 1-methyl-5-[2-(3-methyl-1,2,4-oxadiazol-5-yl)-1H-indol-5-yl]-N-(tetrahydrofuran-2-ylmethyl)-1H-pyrazole-3-carboxamide |
| Chiral | 407.2 | 1-methyl-5-[2-(3-methyl-1,2,4-oxadiazol-5-yl)-1H-indol-5-yl]-N-[(2S)-tetrahydrofuran-2-ylmethyl]-1H-pyrazole-3-carboxamide |

| Structure | LC/MS (M + H)+ | Name |
|---|---|---|
| 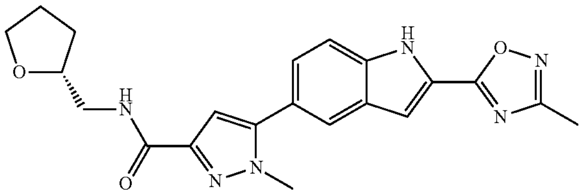 [SMILES: Cc1noc(-c2cc3cc(-c4cc(C(=O)NCC5CCCO5)nn4C)ccc3[nH]2)n1] | 407.2 | 1-methyl-5-[2-(3-methyl-1,2,4-oxadiazol-5-yl)-1H-indol-5-yl]-N-[(2R)-tetrahydrofuran-2-ylmethyl]-1H-pyrazole-3-carboxamide |
| Chiral | | |
| 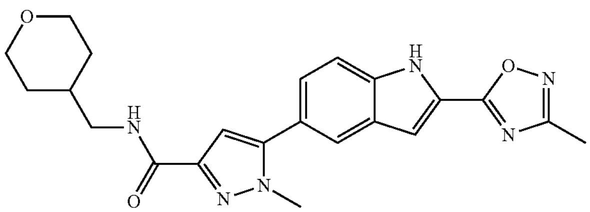 [SMILES: Cc1noc(-c2cc3cc(-c4cc(C(=O)NCC5CCOCC5)nn4C)ccc3[nH]2)n1] | 421.2 | 1-methyl-5-[2-(3-methyl-1,2,4-oxadiazol-5-yl)-1H-indol-5-yl]-N-(tetrahydro-2H-pyran-4-ylmethyl)-1H-pyrazole-3-carboxamide |
| | 403.2 | N-(furan-2-ylmethyl)-1-methyl-5-[2-(3-methyl-1,2,4-oxadiazol-5-yl)-1H-indol-5-yl]-1H-pyrazole-3-carboxamide |
| 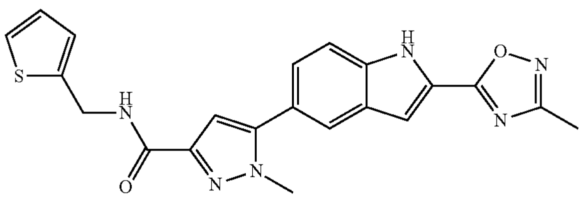 [SMILES: Cc1noc(-c2cc3cc(-c4cc(C(=O)NCc5ccco5)nn4C)ccc3[nH]2)n1] | 419.2 | 1-methyl-5-[2-(3-methyl-1,2,4-oxadiazol-5-yl)-1H-indol-5-yl]-N-(thiophen-2-ylmethyl)-1H-pyrazole-3-carboxamide |
| | 403.2 | N-(furan-3-ylmethyl)-1-methyl-5-[2-(3-methyl-1,2,4-oxadiazol-5-yl)-1H-indol-5-yl]-1H-pyrazole-3-carboxamide |
| 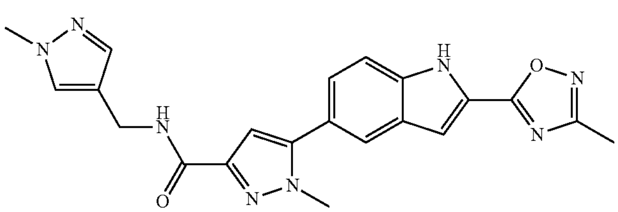 | 417.3 | 1-methyl-5-[2-(3-methyl-1,2,4-oxadiazol-5-yl)-1H-indol-5-yl]-N-[(1-methyl-1H-pyrazol-4-yl)methyl]-1H-pyrazole-3-carboxamide |
| 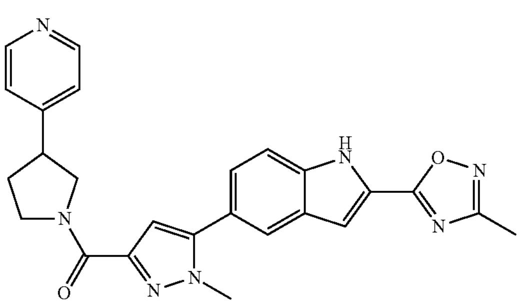 [SMILES: Cc1noc(-c2cc3cc(-c4cc(C(=O)N5CCC(c6ccncc6)C5)nn4C)ccc3[nH]2)n1] | 454.3 | {1-methyl-5-[2-(3-methyl-1,2,4-oxadiazol-5-yl)-1H-indol-5-yl]-1H-pyrazol-3-yl}[3-(pyridin-4-yl)pyrrolidin-1-yl]methanone |

| Structure | LC/MS (M + H)+ | Name |
|---|---|---|
| 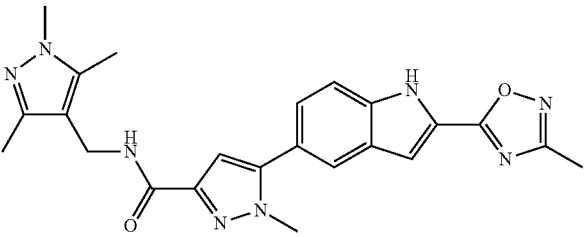 | 445.3 | 1-methyl-5-[2-(3-methyl-1,2,4-oxadiazol-5-yl)-1H-indol-5-yl]-N-[(1,3,5-trimethyl-1H-pyrazol-4-yl)methyl]-1H-pyrazole-3-carboxamide |
| 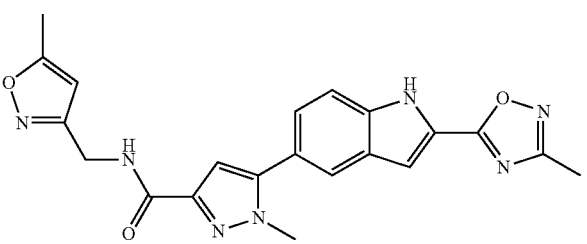 [SMILES: Cc1noc(-c2cc3cc(-c4cc(C(=O)NCc5cc(C)on5)nn4C)ccc3[nH]2)n1] | 418.2 | 1-methyl-N-[(5-methylisoxazol-3-yl)methyl]-5-[2-(3-methyl-1,2,4-oxadiazol-5-yl)-1H-indol-5-yl]-1H-pyrazole-3-carboxamide |
| 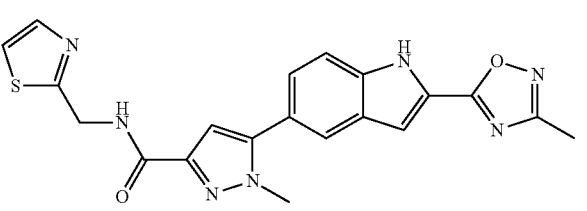 | 420.2 | 1-methyl-5-[2-(3-methyl-1,2,4-oxadiazol-5-yl)-1H-indol-5-yl]-N-(1,3-thiazol-2-ylmethyl)-1H-pyrazole-3-carboxamide |
| 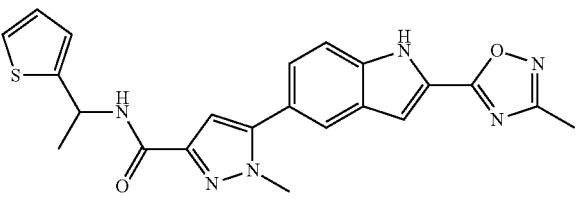 | 433.2 | 1-methyl-5-[2-(3-methyl-1,2,4-oxadiazol-5-yl)-1H-indol-5-yl]-N-[1-(thiophen-2-yl)ethyl]-1H-pyrazole-3-carboxamide |
| 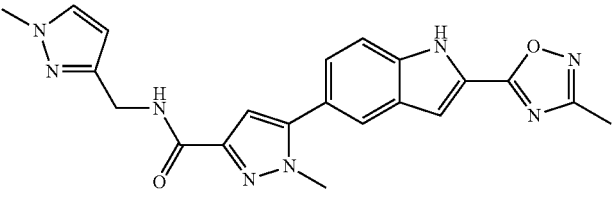 | 417.2 | 1-methyl-5-[2-(3-methyl-1,2,4-oxadiazol-5-yl)-1H-indol-5-yl]-N-[(1-methyl-1H-pyrazol-3-yl)methyl]-1H-pyrazole-3-carboxamide |
| 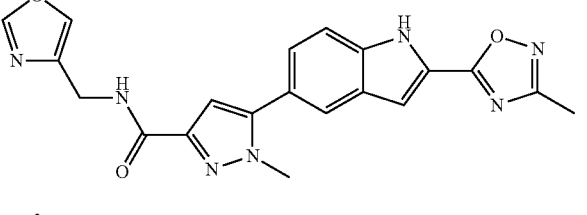 | 404.2 | 1-methyl-5-[2-(3-methyl-1,2,4-oxadiazol-5-yl)-1H-indol-5-yl]-N-(1,3-oxazol-4-ylmethyl)-1H-pyrazole-3-carboxamide |
| 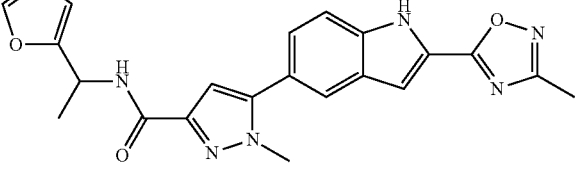 | 417.2 | N-[1-(furan-2-yl)ethyl]-1-methyl-5-[2-(3-methyl-1,2,4-oxadiazol-5-yl)-1H-indol-5-yl]-1H-pyrazole-3-carboxamide |

-continued

| Structure | LC/MS (M + H)+ | Name |
|---|---|---|
| 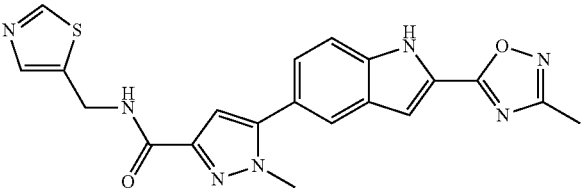 [SMILES: Cc1noc(-c2cc3cc(-c4cc(C(=O)NCc5cncs5)nn4C)ccc3[nH]2)n1] | 420.2 | 1-methyl-5-[2-(3-methyl-1,2,4-oxadiazol-5-yl)-1H-indol-5-yl]-N-(1,3-thiazol-5-ylmethyl)-1H-pyrazole-3-carboxamide |
| 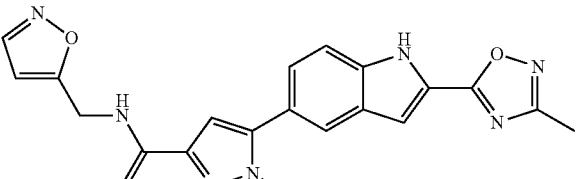 | 404.2 | N-(isoxazol-5-ylmethyl)-1-methyl-5-[2-(3-methyl-1,2,4-oxadiazol-5-yl)-1H-indol-5-yl]-1H-pyrazole-3-carboxamide |
| 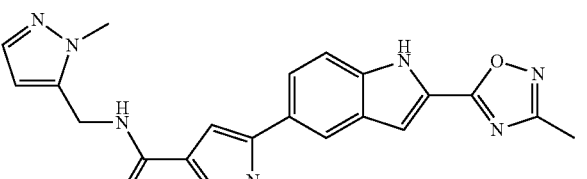 | 417.2 | 1-methyl-5-[2-(3-methyl-1,2,4-oxadiazol-5-yl)-1H-indol-5-yl]-N-[(1-methyl-1H-pyrazol-5-yl)methyl]-1H-pyrazole-3-carboxamide |
| 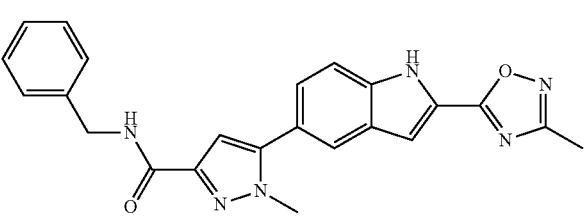 [SMILES: Cc1noc(-c2cc3cc(-c4cc(C(=O)NCc5ccccc5)nn4C)ccc3[nH]2)n1] | 413.2 | N-benzyl-1-methyl-5-[2-(3-methyl-1,2,4-oxadiazol-5-yl)-1H-indol-5-yl]-1H-pyrazole-3-carboxamide |
| 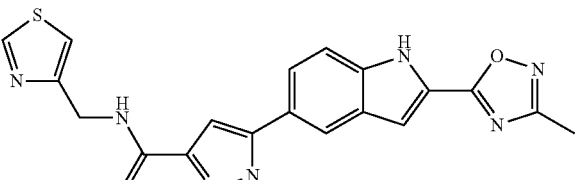 | 420.2 | 1-methyl-5-[2-(3-methyl-1,2,4-oxadiazol-5-yl)-1H-indol-5-yl]-N-(1,3-thiazol-4-ylmethyl)-1H-pyrazole-3-carboxamide |
| 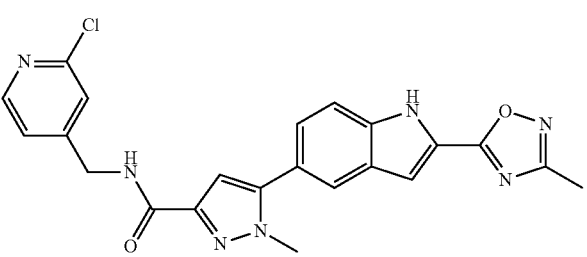 [SMILES: Cc1noc(-c2cc3cc(-c4cc(C(=O)NCc5ccnc(Cl)c5)nn4C)ccc3[nH]2)n1] | 448.2 | N-[(2-chloropyridin-4-yl)methyl]-1-methyl-5-[2-(3-methyl-1,2,4-oxadiazol-5-yl)-1H-indol-5-yl]-1H-pyrazole-3-carboxamide |
| 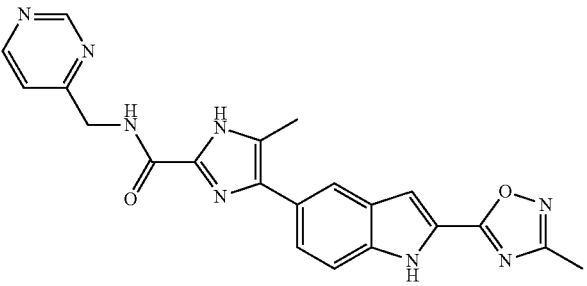 | 414.4 | 5-Methyl-4-[2-(3-methyl-1,2,4-oxadiazol-5-yl)-1H-indol-5-yl]-1-H-imidazole-2-carboxylic acid (pyrimidin-4-ylmethyl)-amide |

-continued

| Structure | LC/MS (M + H)+ | Name |
|---|---|---|
| 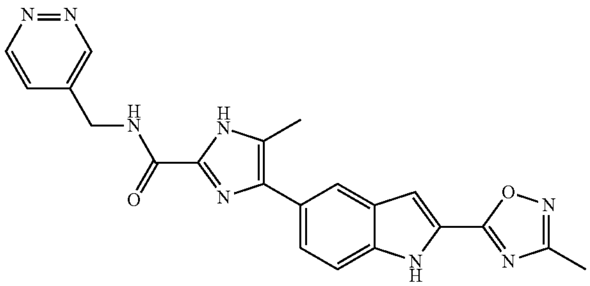 [SMILES: Cc1noc(-c2cc3cc(-c4nc(C(=O)NCc5ccncn5)[nH]c4C)ccc3[nH]2)n1] | 414.4 | 5-Methyl-4-[2-(3-methyl-1,2,4-oxadiazol-5-yl)-1H-indol-5-yl]-1H-imidazole-2-carboxylic acid (pyridazin-4-ylmethyl)-amide |
| 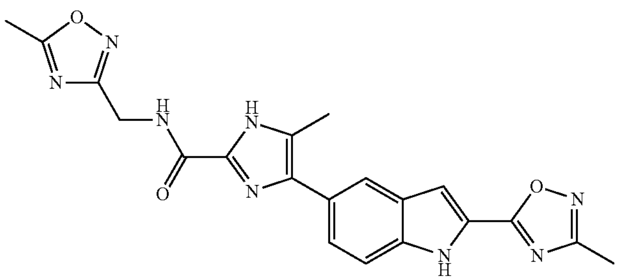 | 418.4 | 5-Methyl-4-[2-(3-methyl-1,2,4-oxadiazol-5-yl)-1H-indol-5-yl]-1H-imidazole-2-carboxylic acid (5-methyl-1,2,4-oxadiazol-3-ylmethyl)-amide |
| 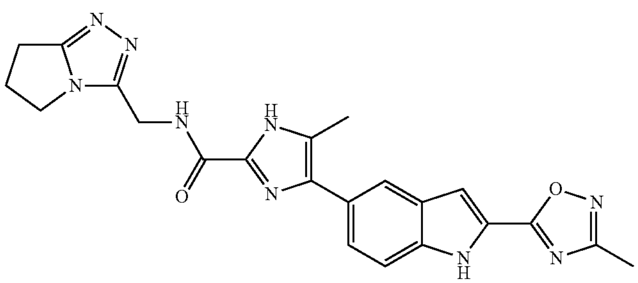 [SMILES: Cc1noc(-c2cc3cc(-c4nc(C(=O)NCc5nnc6n5CCC6)[nH]c4C)ccc3[nH]2)n1] | 443.5 | 5-Methyl-4-[2-(3-methyl-1,2,4-oxadiazol-5-yl)-1H-indol-5-yl]-1H-imidazole-2-carboxylic acid (6,7-dihydro-5H-pyrrolo[2,1-c]-1,2,4-triazol-3-ylmethyl)-amide |
| 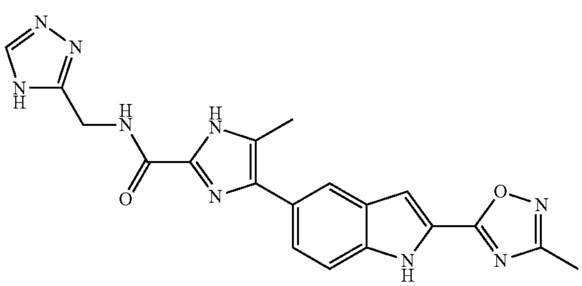 [SMILES: Cc1noc(-c2cc3cc(-c4nc(C(=O)NCc5nnc[nH]5)[nH]c4C)ccc3[nH]2)n1] | 403.4 | 5-Methyl-4-[2-(3-methyl-1,2,4-oxadiazol-5-yl)-1H-indol-5-yl]-1H-imidazole-2-carboxylic acid (4H-1,2,4-triazol-3-ylmethyl)-amide |
| 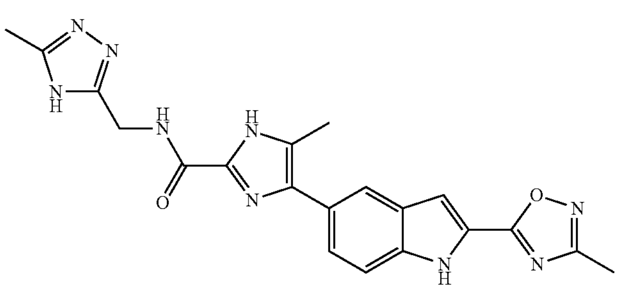 | 417.4 | 5-Methyl-4-[2-(3-methyl-1,2,4-oxadiazol-5-yl)-1H-indol-5-yl]-1H-imidazole-2-carboxylic acid (5-methyl-4H-1,2,4-triazol-3-ylmethyl)-amide |

Assessment of Biological Properties

The biological properties of the compounds of the formula I can be assessed using the assays described below in addition to other art recognized assays.

The EnzoLyte™ 520 Generic MMP Assay Kit (AnaSpec Inc.) can detect the activity of several MMPs including MMP-1, 2, 3, 7, 8, 9, 13, and 14. This kit uses a 5-FAM/QXL™ 520 fluorescence resonance energy transfer (FRET) peptide as an MMP substrate. In the intact FRET peptide, the fluorescence of 5-FAM is quenched by QXL™ 520. Upon cleavage into two separate fragments by MMPs, the fluorescence of 5-FAM is recovered, and can be monitored at excitation/emission wavelengths=490 nm/520 nm. The assays are performed in a convenient 96-well or 384-well microplate format.

Preferred compounds will have an IC50 of <500 nM.

Therapeutic Use

As can be demonstrated by the assays described above, the compounds of the invention are useful in inhibiting MMP-13. Compounds of the invention are therefore useful in the treatment of diseases including rheumatoid arthritis, osteoarthritis, osteoporosis, peridontitis, atherosclerosis, congestive heart failure, multiple sclerosis and tumor metastasis. They can be used in patients as drugs, particularly in the form of pharmaceutical compositions as set forth herein. As mentioned previously, MMP-13 are thought to play a major role on extracellular matrix degradation and cellular processes such as proliferation, migration (adhesion/dispersion), differentiation, angiogenesis, apoptosis and host defense, compounds of the invention are therefore also useful in the treatment of the following diseases: contact dermatitis, bone resorption diseases, reperfusion injury, asthma, Guillain-Barre syndrome, Crohn's disease, ulcerative colitis, psoriasis, graft versus host disease, systemic lupus erythematosus and insulin-dependent diabetes mellitus, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure.

As disclosed in the Background of the Invention, the compounds of the invention will be useful for treating tumor metastasis. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary,neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A compound of the formula (I):

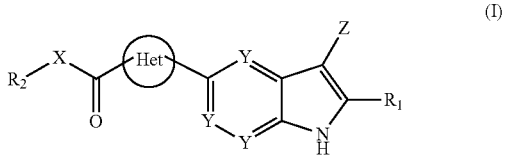

(I)

Het is a ring chosen from phenyl, oxazolyl, isoxazolyl, oxadiazolyl, thiazolyl, isothiazolyl, pyrazolyl, pyrrolyl, imidazolyl, pyridinyl, pyrimidinyl and pyridazinyl each optionally substituted by one to three $C_{1-5}$ alkyl, $C_{1-5}$ alkoxy, $C_{1-5}$ acyl, $C_{1-5}$ acylamino, amino, cyano, hydroxyl or halogen;

X is —N($R_3$)—;

Y is N or CH;

Z is H or F;

$R_1$ is chosen from $C_{1-5}$ alkoxy$C_{1-5}$ alkyl, $C_{1-5}$ alkoxycarbonyl-$(CH_2)_n$—, —C(O)N$R_4R_5$ and $Ar_1$;

$R_2$ is chosen from $Ar_2$—$(CH_2)_n$—, heterocycle and $C_{1-5}$ alkyl;

$R_3$ is chosen from hydrogen and $C_{1-5}$ alkyl;

each $R_4$ and $R_5$ is independently chosen from hydrogen, $C_{1-5}$ acyl, $C_{1-5}$ alkyl, $C_{1-5}$ alkoxy, hydroxyl, carbocycle-$(CH_2)_n$—, heteroaryl and heterocycle-$(CH_2)_n$—;

$Ar_1$ is chosen from carbocycle, heteroaryl and heterocycle wherein $Ar_1$ is optionally substituted by one to three $C_{1-5}$ alkyl, $C_{1-5}$ alkoxy, $C_{1-5}$ acyl, $C_{1-5}$ acylamino, amino, cyano, hydroxyl or halogen;

$Ar_2$ is chosen from carbocycle, heteroaryl and heterocycle wherein $Ar_2$ is optionally substituted by one to three heteroaryl, $C_{1-5}$ alkyl, $C_{1-5}$ alkoxy-$(CH_2)_n$—, $C_{1-5}$ alkoxycarbonyl-$(CH_2)_n$—, carboxy-$(CH_2)_n$—, $C_{1-5}$ acyl, $C_{1-5}$ acylamino, amino, cyano, hydroxyl, sulfonyl, sulfoxide, thio, oxo or halogen;

each n is independently 0-2;

or a pharmaceutically acceptable salt thereof.

2. The compound according to claim 1, wherein the compound is represented by formula (II)

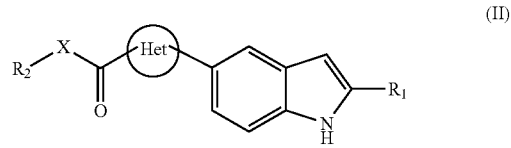

(II)

wherein $R_1$ is chosen from $C_{1-5}$ alkoxy $C_{1-5}$ alkyl, $C_{1-5}$ alkoxycarbonyl-$(CH_2)_n$— and $Ar_1$;

$R_2$ is chosen from $Ar_2$—$(CH_2)_n$—, heterocycle and $C_{1-5}$ alkyl;

$R_3$ is chosen from hydrogen and $C_{1-5}$ alkyl;

$Ar_1$ is chosen from phenyl, oxazolyl, 4,5-dihydro-oxazolyl, isoxazolyl, oxadiazolyl, thiazolyl, pyrazolyl, pyrrolyl, imidazolyl, pyridinyl, pyrimidinyl, pyridazinyl and pyrazinyl wherein $Ar_1$ is optionally substituted by one to three $C_{1-5}$ alkyl, $C_{1-5}$ alkoxy, $C_{1-5}$ acyl, $C_{1-5}$ acylamino, amino, cyano, hydroxyl or halogen;

$Ar_2$ is chosen from phenyl, oxazolyl, isoxazolyl, oxadiazolyl, furanyl, thiophenyl, triazolyl, thiadiazolyl, isothiazolyl, thiazolyl, pyrazolyl, pyrrolyl, imidazolyl, pyridinyl, pyrimidinyl, pyridazinyl and pyrazinyl wherein $Ar_2$ is optionally substituted by one to three $C_{1-5}$ alkyl, $C_{1-5}$ alkoxy-$(CH_2)_n$—, $C_{1-5}$ alkoxycarbonyl-$(CH_2)_n$—, carboxy-$(CH_2)_n$—, $C_{1-5}$ acyl, $C_{1-5}$ acylamino, amino, cyano, hydroxyl, oxo or halogen.

3. The compound according to claim 2 and wherein $R_2$ is chosen from $Ar_2$—$(CH_2)_n$—;

$Ar_2$ is chosen from phenyl, oxazolyl, isoxazolyl, oxadiazolyl, thiazolyl, pyrazolyl, pyrrolyl, imidazolyl, pyridinyl, pyrimidinyl, pyridazinyl and pyrazinyl wherein $Ar_2$ is optionally substituted by one to three $C_{1-5}$ alkyl, $C_{1-5}$ alkoxy-$(CH_2)_n$—, $C_{1-5}$ alkoxycarbonyl-$(CH_2)_n$—, carboxy-$(CH_2)_n$—, $C_{1-5}$ acyl, $C_{1-5}$ acylamino, amino, cyano, hydroxyl, oxo or halogen.

4. The compound according to claim 3 and wherein

Het is a ring chosen from pyrazolyl, imidazolyl and pyridinyl each optionally substituted by one to three $C_{1-5}$ alkyl, $C_{1-5}$ alkoxy, $C_{1-5}$ acyl, $C_{1-5}$ acylamino, amino, cyano, hydroxyl or halogen;

$Ar_1$ is chosen from phenyl, oxazolyl, 4,5-dihydro-oxazolyl, isoxazolyl, oxadiazolyl, pyrazolyl, imidazolyl, pyridinyl and pyrimidinyl wherein $Ar_1$ is optionally substituted by one to two $C_{1-5}$ alkyl or halogen;

$Ar_2$ is chosen from phenyl, pyridinyl, pyrimidinyl, pyridazinyl and pyrazinyl wherein $Ar_2$ is optionally substituted by one to three $C_{1-5}$ alkyl, $C_{1-5}$ alkoxy, $C_{1-5}$ alkoxycarbonyl, carboxy, or halogen.

5. The compound according to claim 3 and wherein

Het is a ring chosen from pyrazolyl, imidazolyl and pyridinyl each optionally substituted by $C_{1-5}$ alkyl, $C_{1-5}$ alkoxy or halogen;

$R_1$ is chosen from $C_{1-2}$ alkoxy$C_{1-2}$ alkyl, $C_{1-2}$ alkoxycarbonyl and $Ar_1$;

$R_2$ is chosen from $Ar_2$-$CH_2$—;

$Ar_1$ is chosen from phenyl, 4,5-dihydro-oxazolyl, oxadiazolyl, pyrazolyl, pyridinyl and pyrimidinyl wherein $Ar_1$ is optionally substituted by one to two $C_{1-3}$ alkyl or halogen;

$Ar_2$ is chosen from phenyl and pyridinyl wherein $Ar_2$ is optionally substituted by one to two $C_{1-5}$ alkyl, $C_{1-5}$ alkoxy, $C_{1-5}$ alkoxycarbonyl, hydroxyl, oxo, carboxy, or halogen.

6. The compound according to claim 1 and wherein
Y is CH;
Het is chosen from
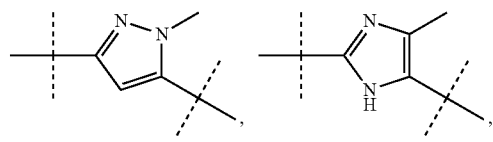
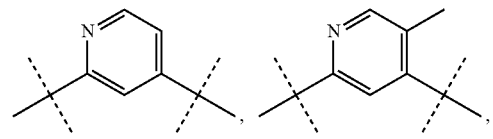
R₂ is chosen from
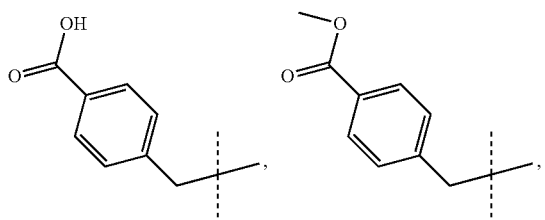
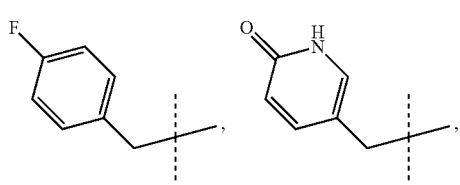
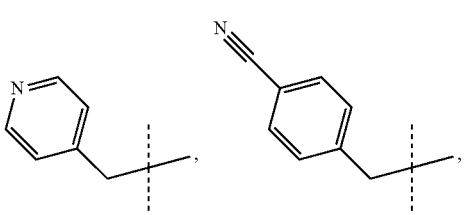
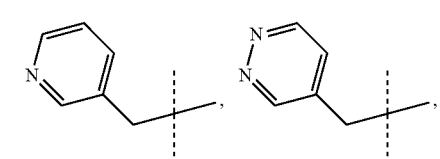
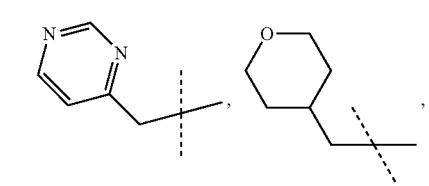
-continued
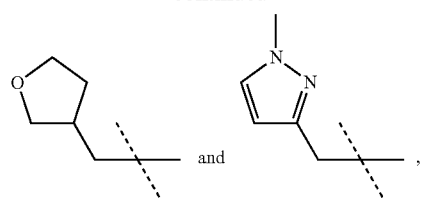
and
R₁ is chosen from
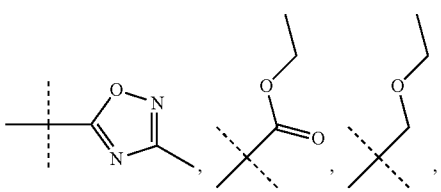
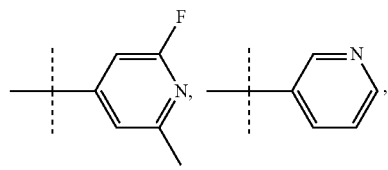
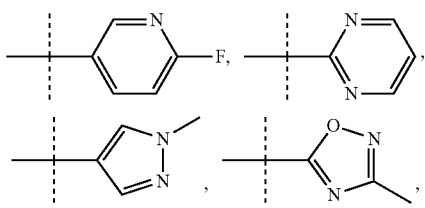
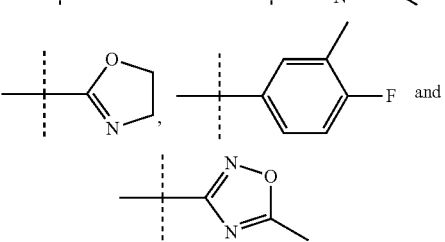
7. The compound according to claim 1 and wherein
R₂ is hydrogen or $C_{1-3}$ alkyl;
R₁ is chosen from $C_{1-5}$ alkoxy$C_{1-5}$ alkyl, $C_{1-5}$ alkoxycarbonyl- and
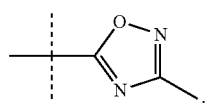
8. The compound according to claim 7 and wherein
R₁ is $C_{1-5}$ alkoxycarbonyl-.

9. A compound chosen from
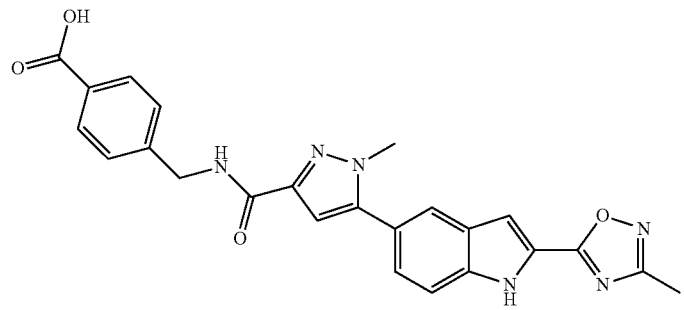
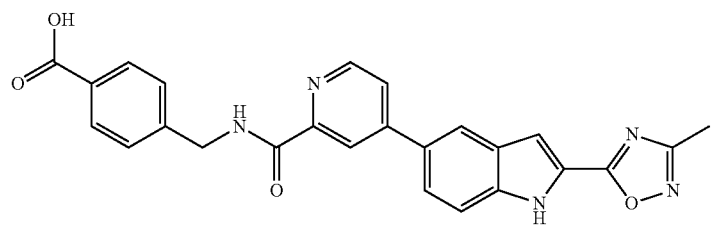
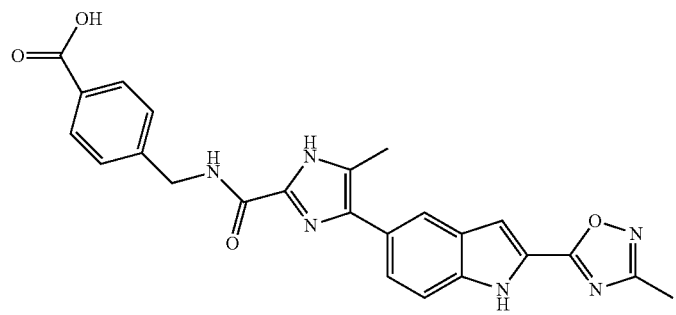
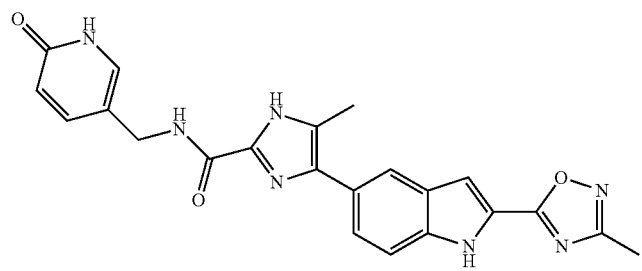
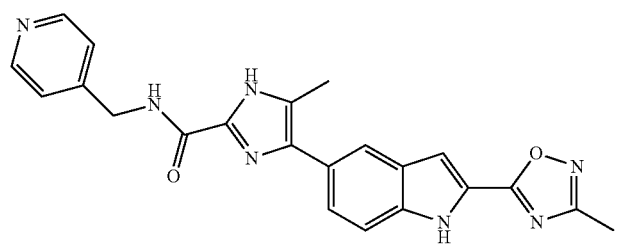
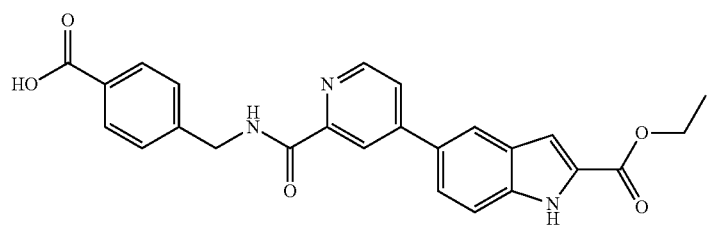

-continued
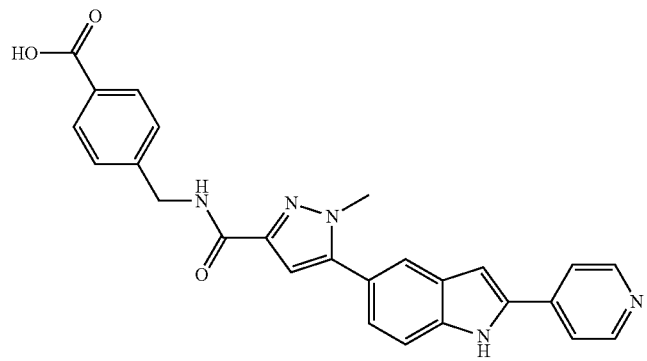
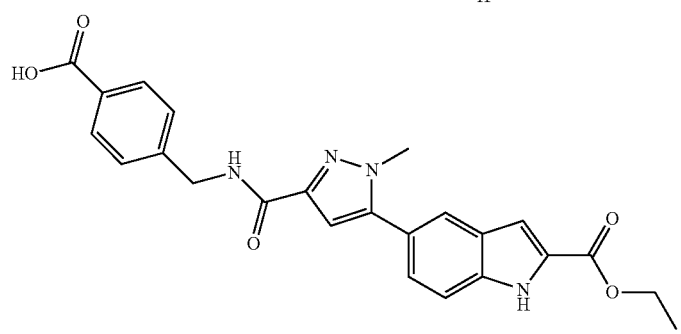
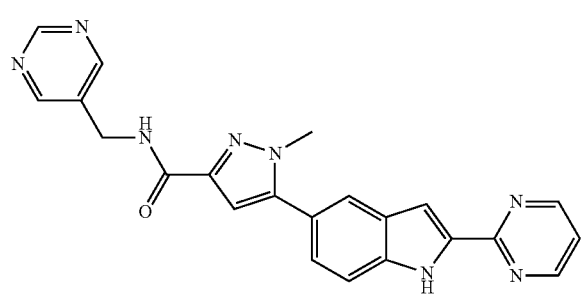
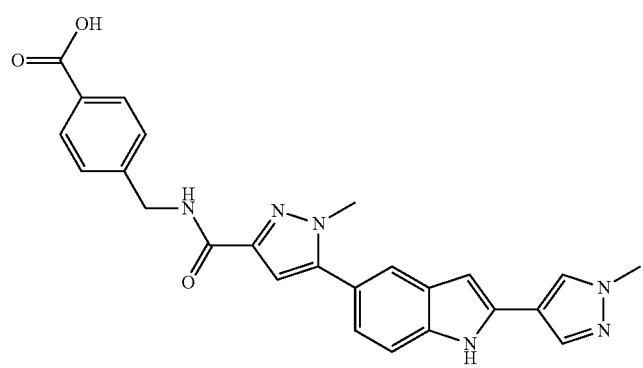
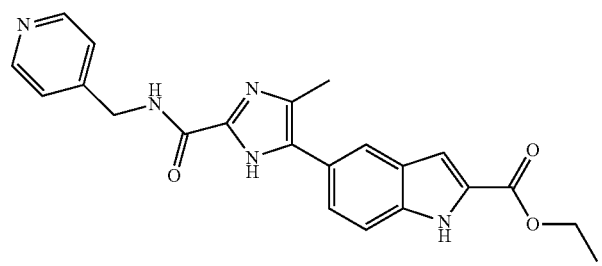

-continued
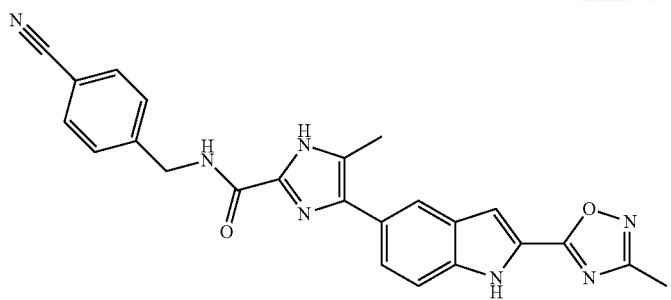
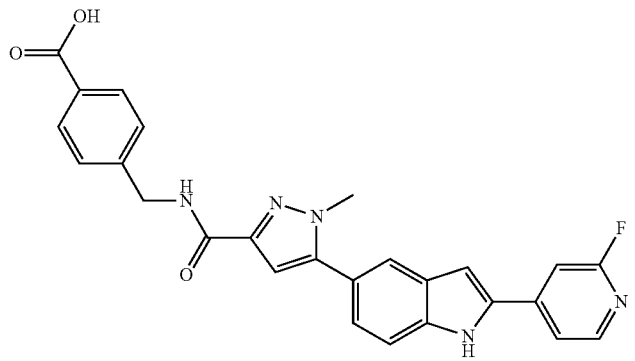
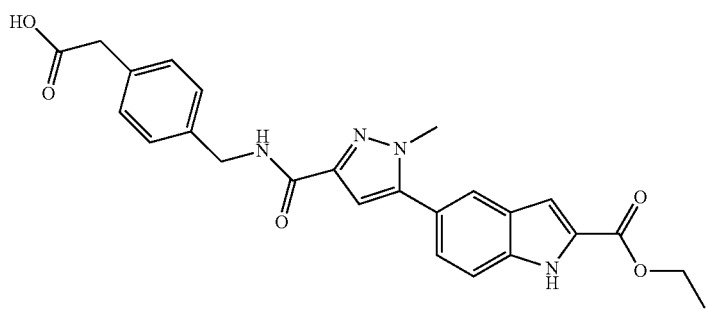
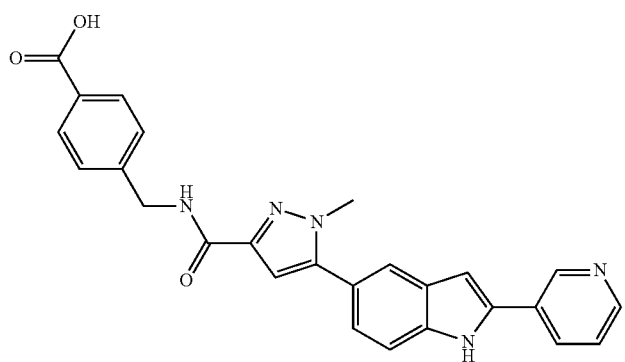
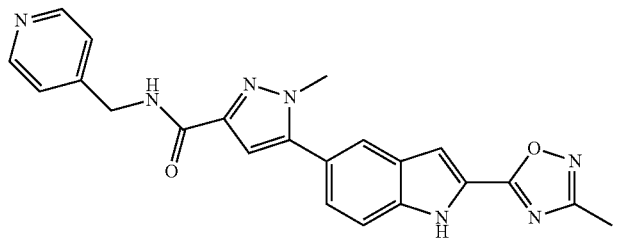

-continued
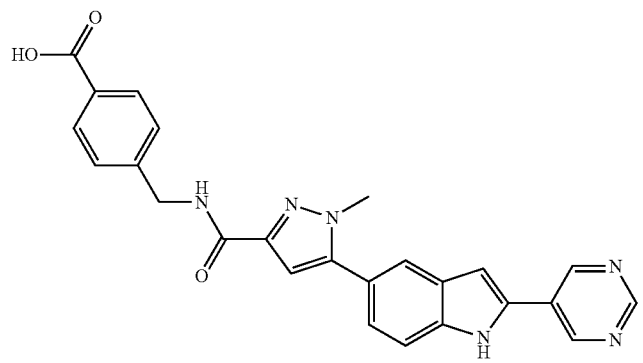
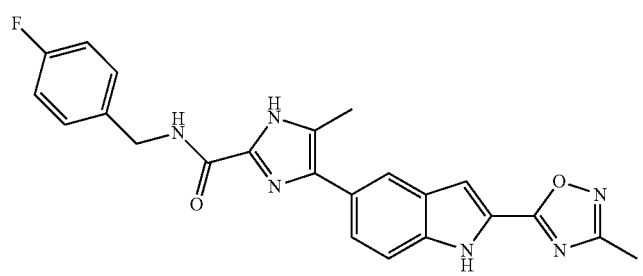
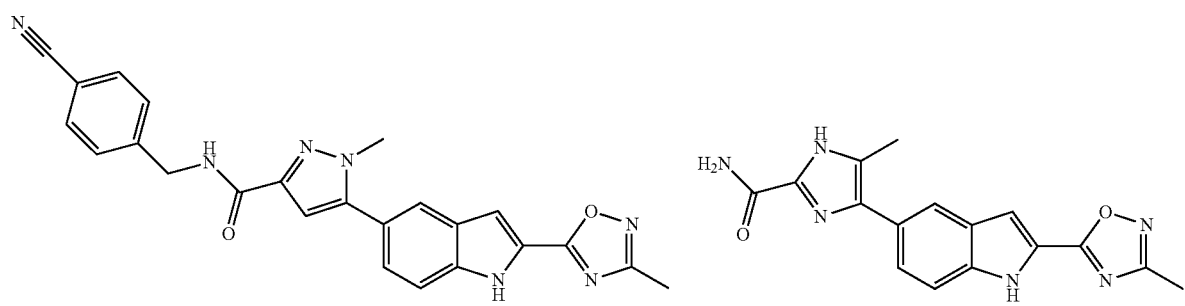 [SMILES: Cc1noc(-c2cc3cc(-c4cc(C(=O)NCc5ccc(C#N)cc5)nn4C)ccc3[nH]2)n1 ; Cc1noc(-c2cc3cc(-c4nc(C(N)=O)[nH]c4C)ccc3[nH]2)n1]
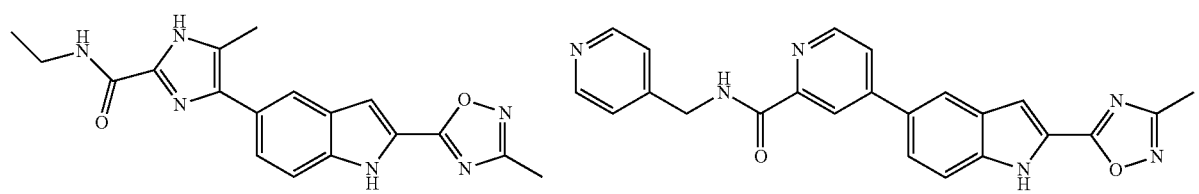
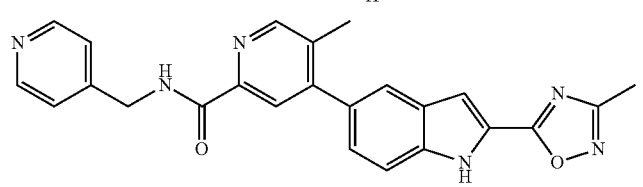
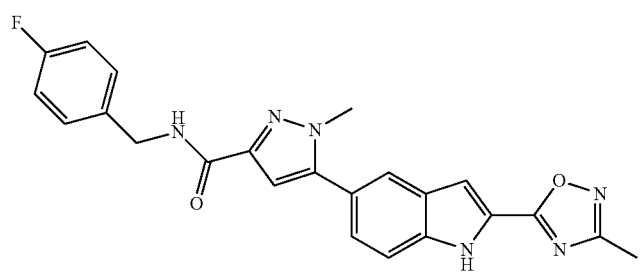

-continued
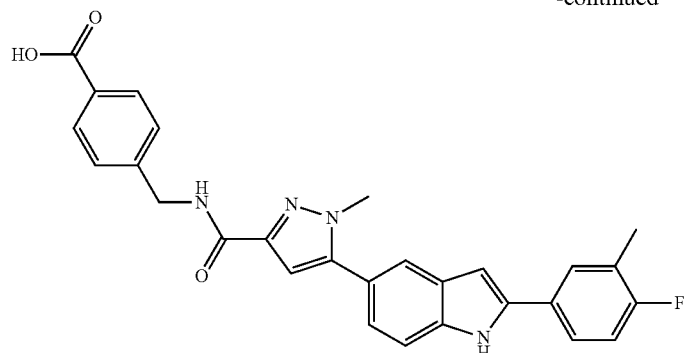
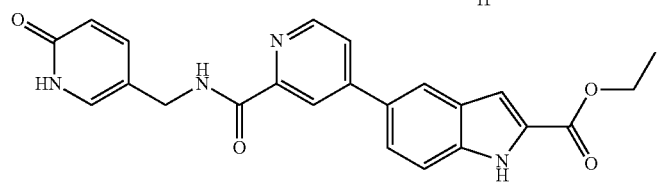
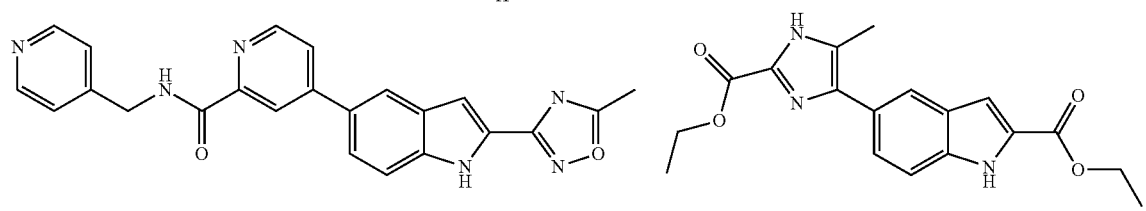
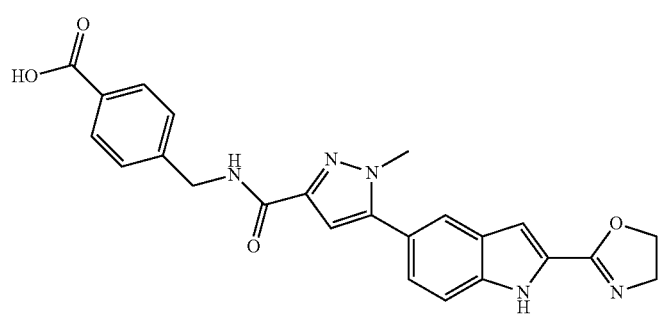
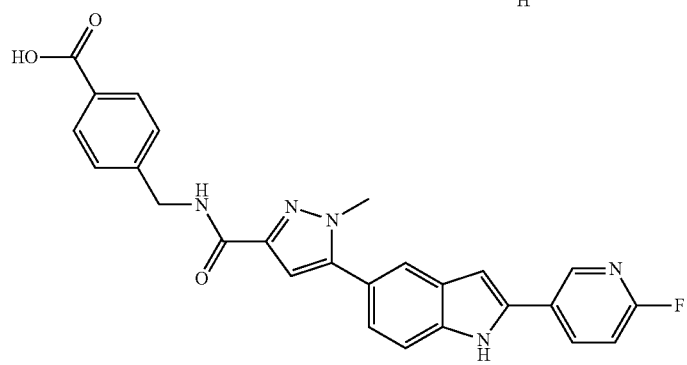
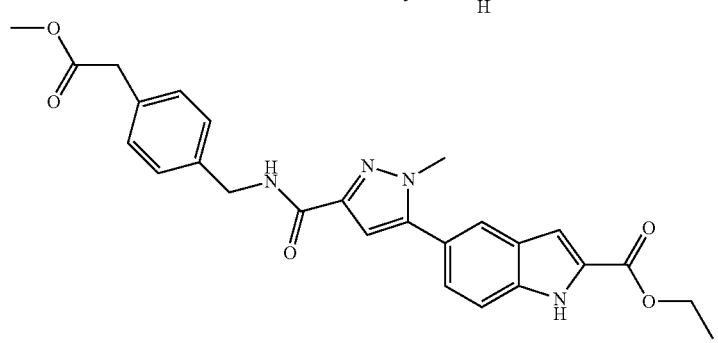

-continued
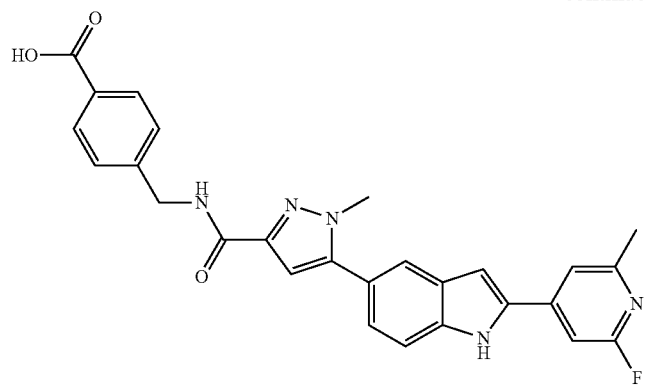
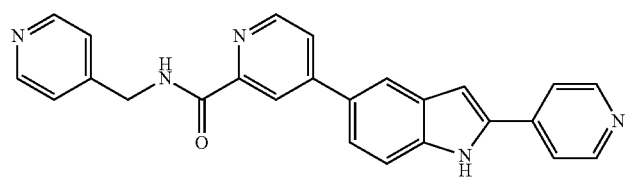
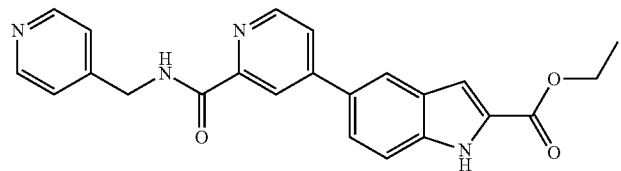
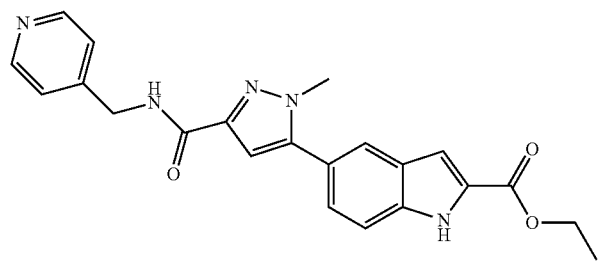
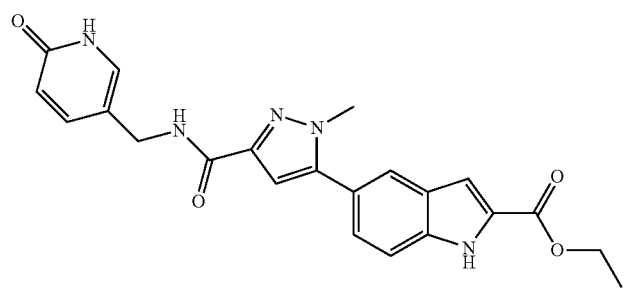
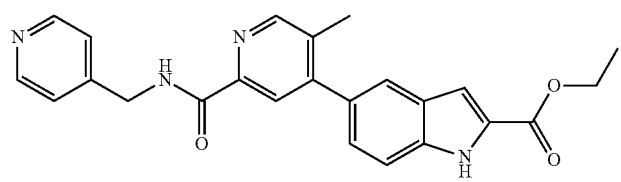
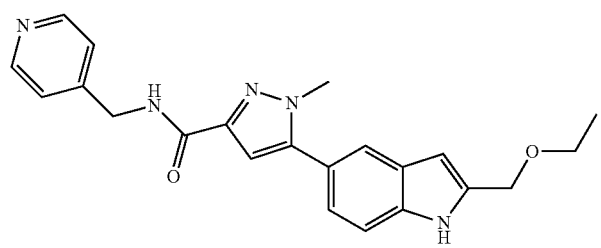

-continued
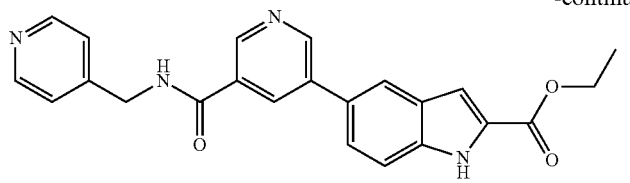
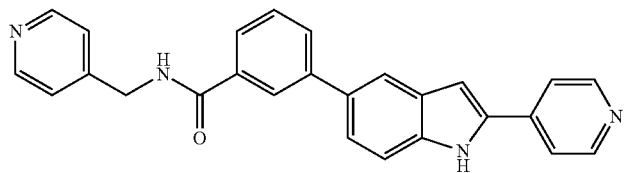
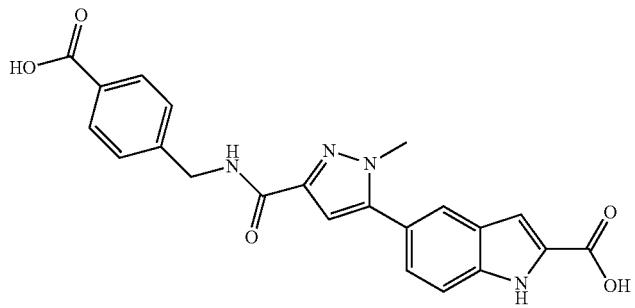
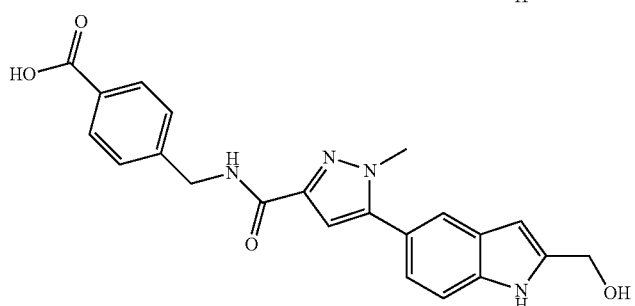
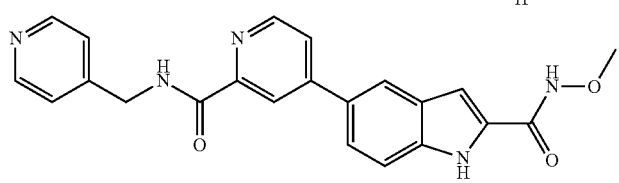
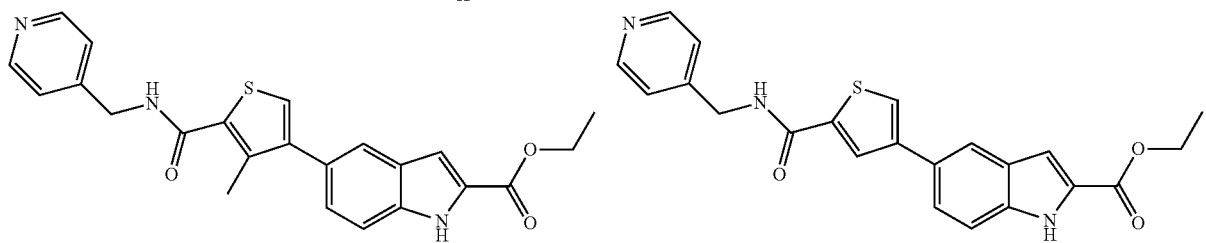
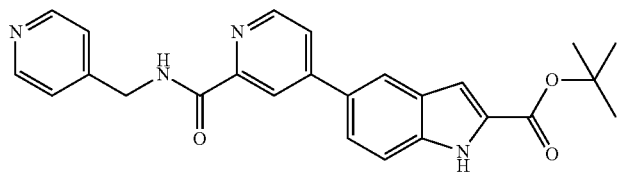
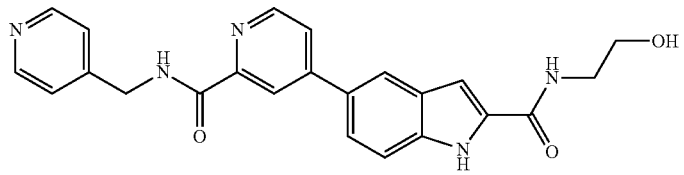

151 152
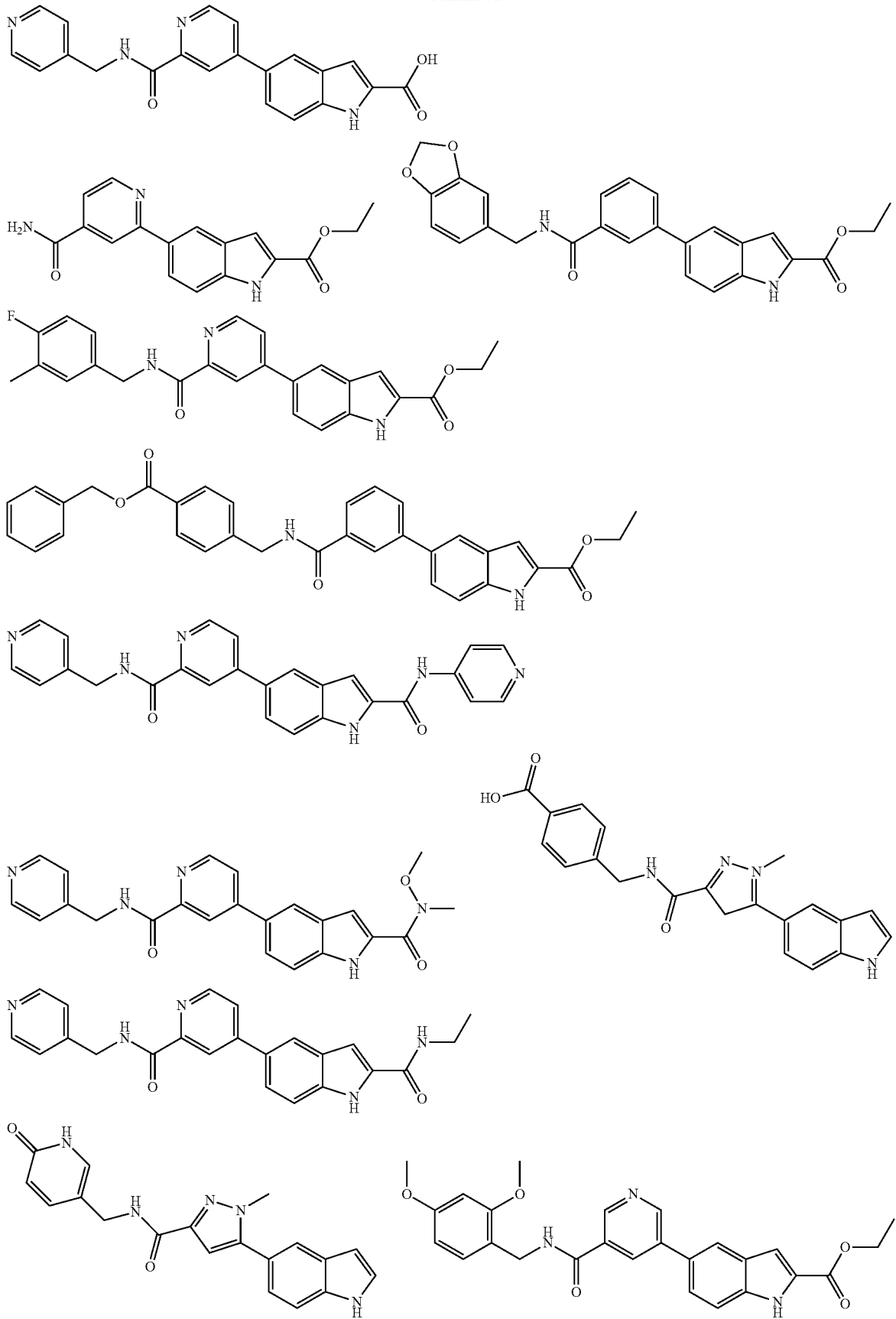
-continued

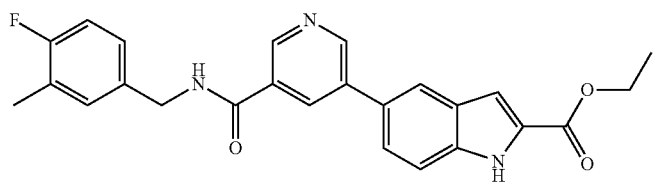
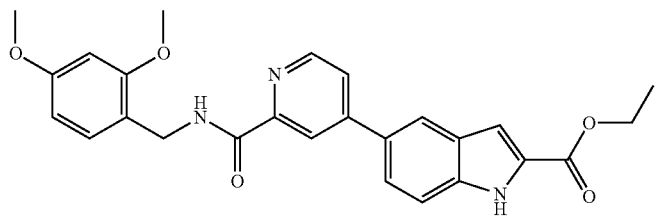
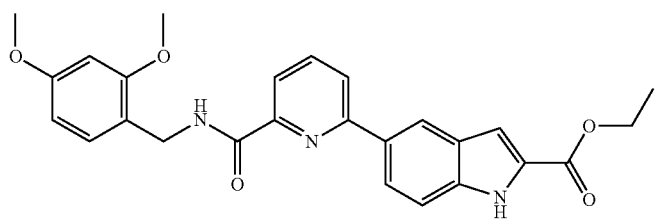
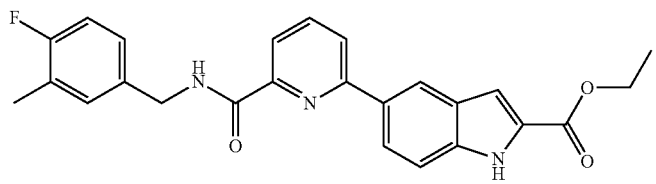
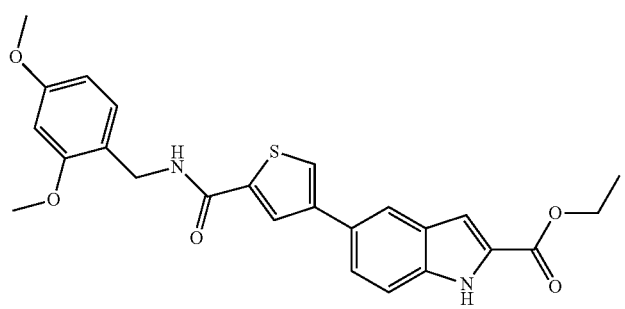
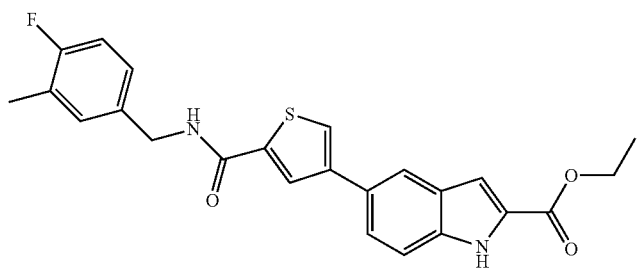
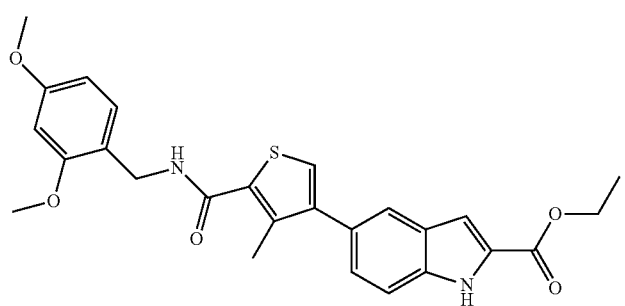

-continued
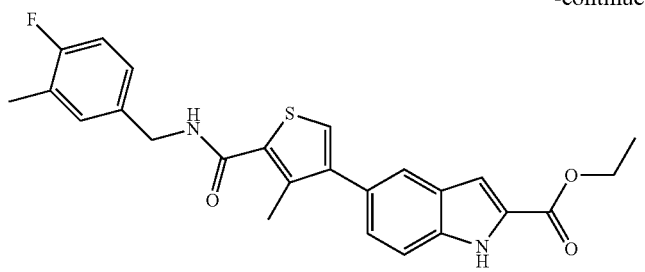
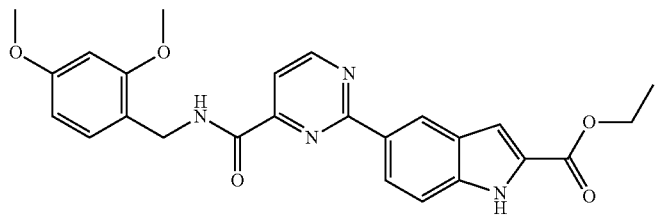
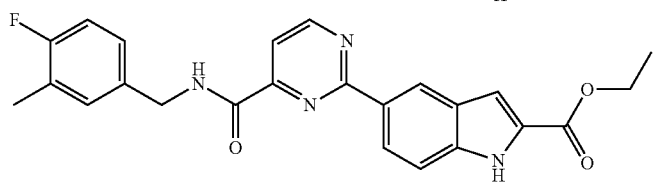
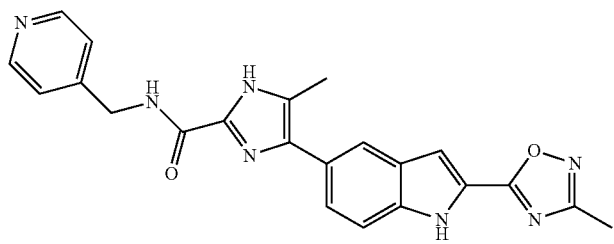
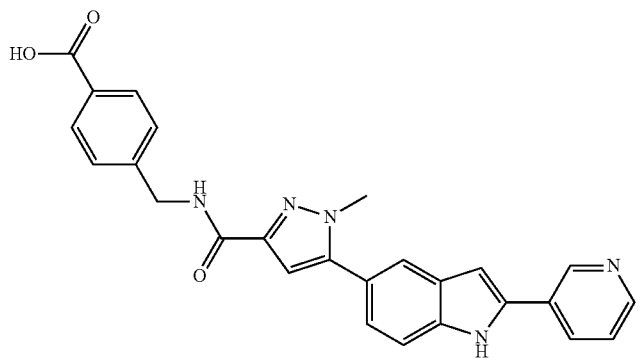
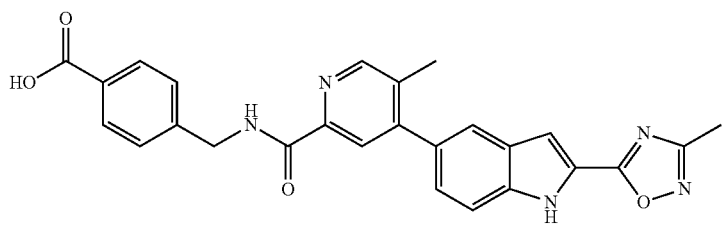
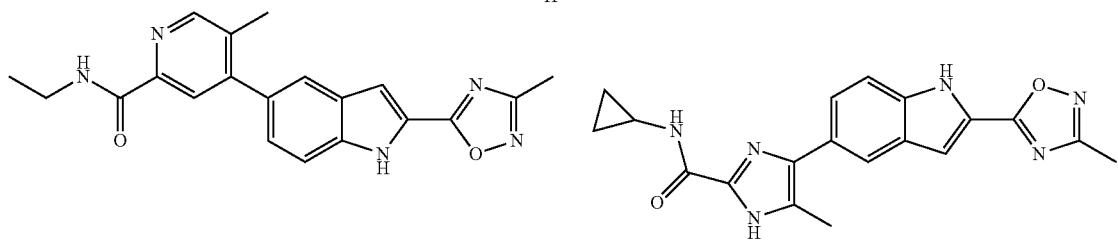

-continued
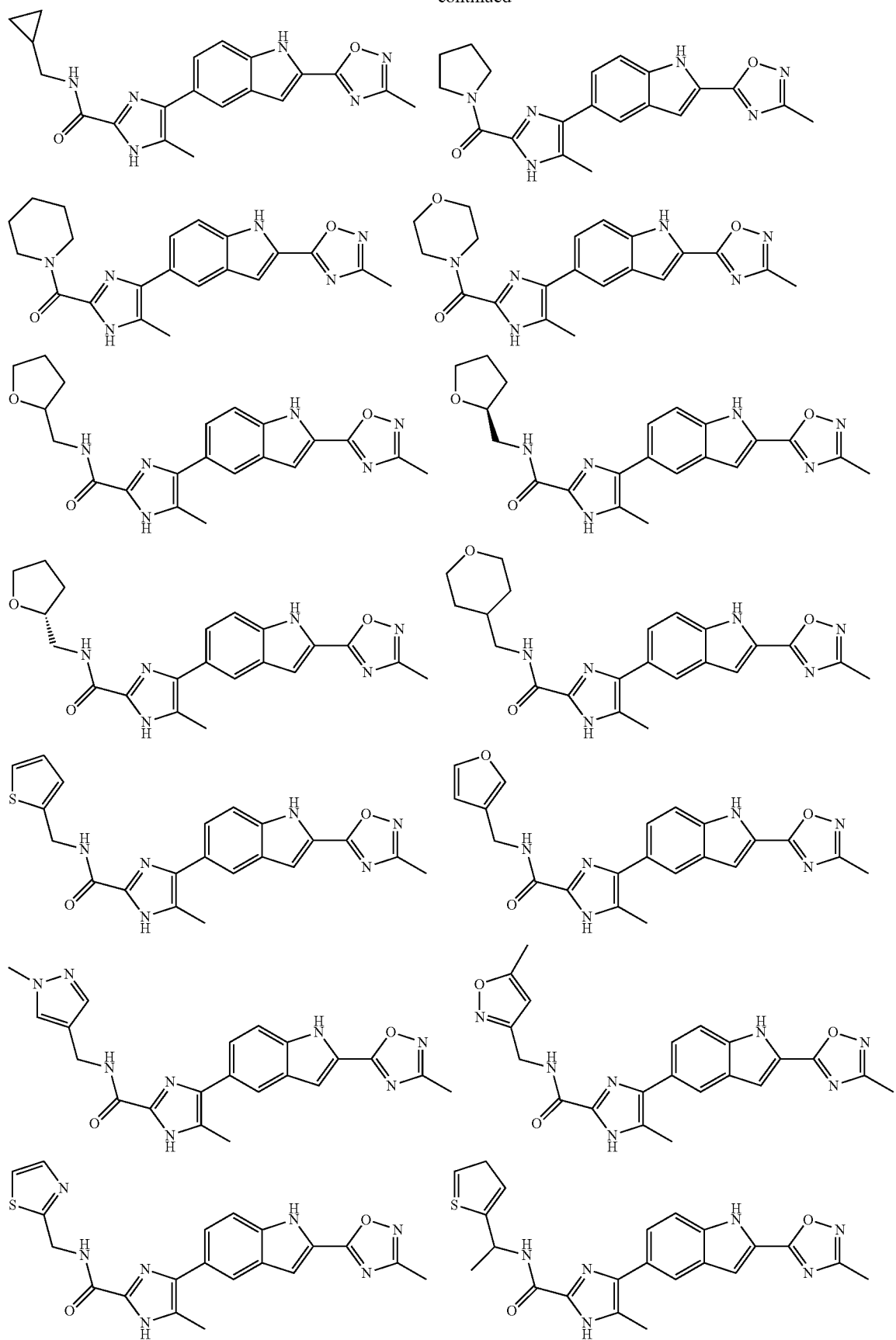

159
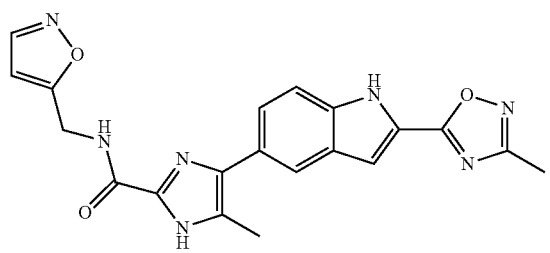
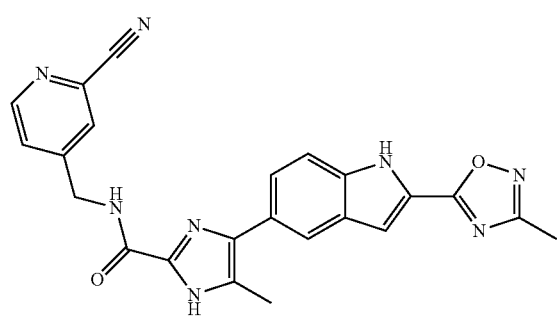
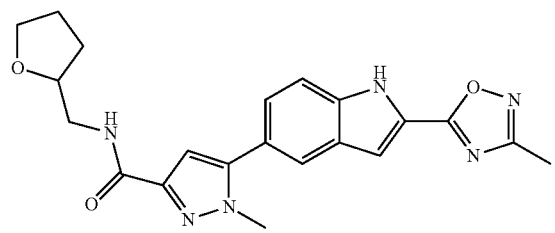
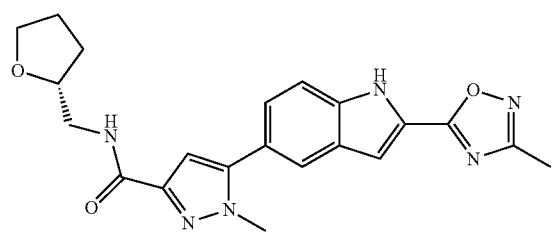
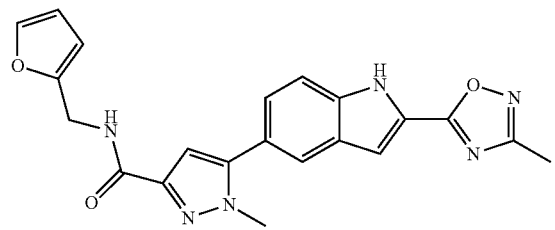
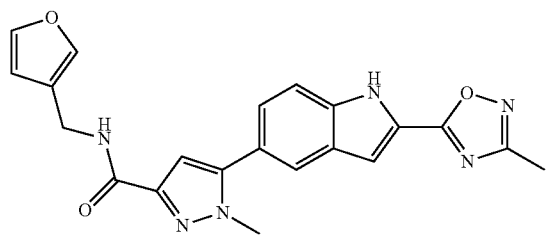
160
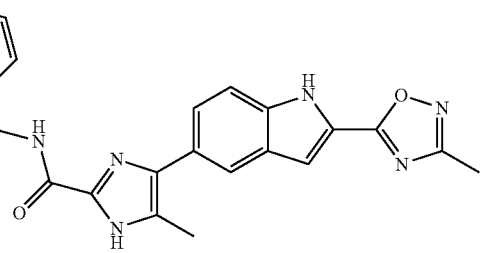
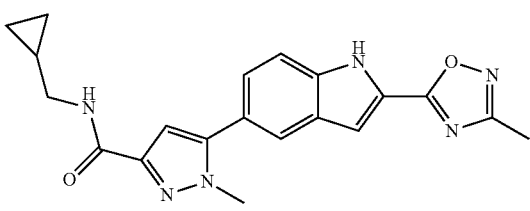
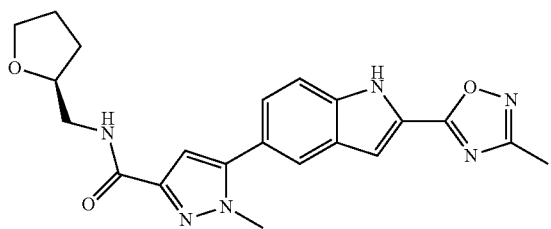
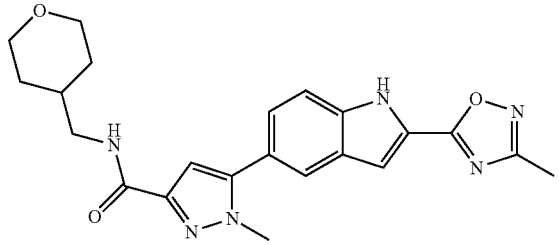
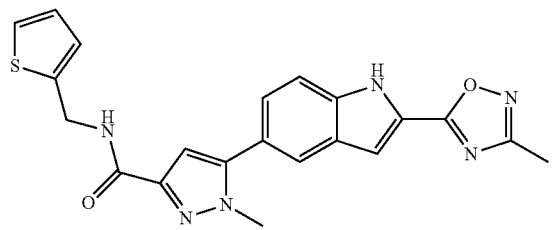
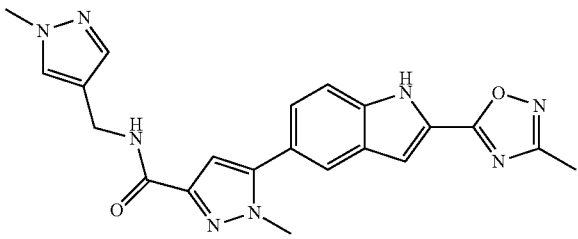

-continued
| 161 | 162 |
|---|---|
| 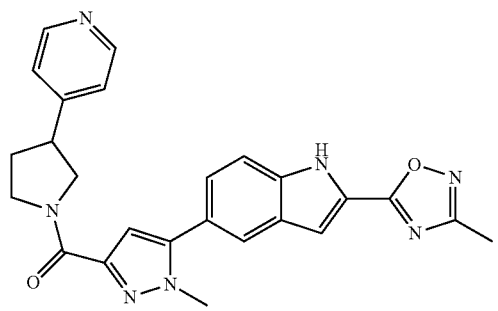 | 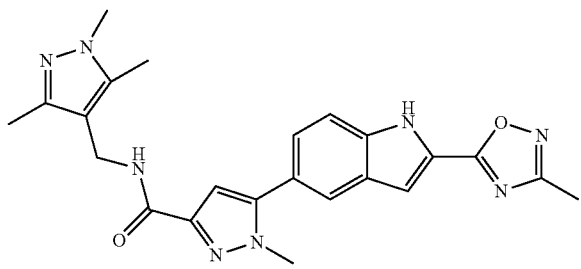 |
| 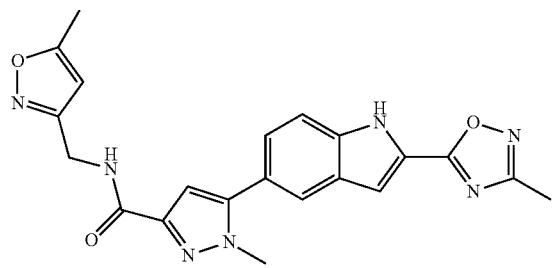 | 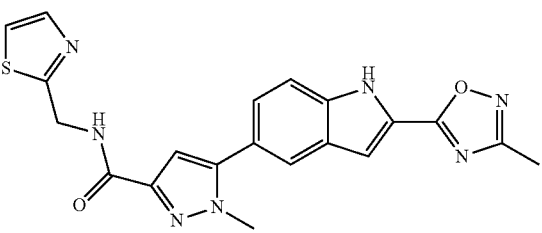 |
| 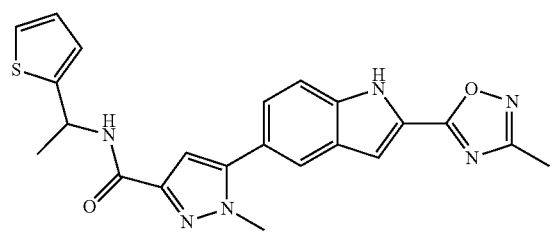 | 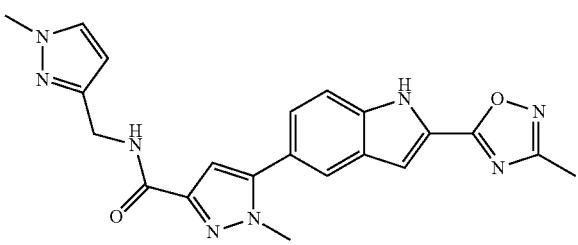 |
| 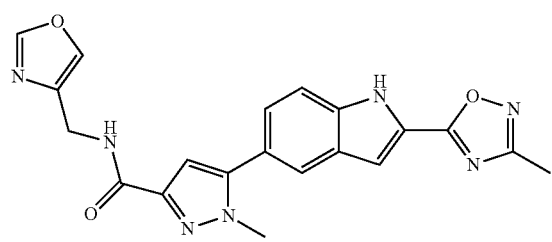 | 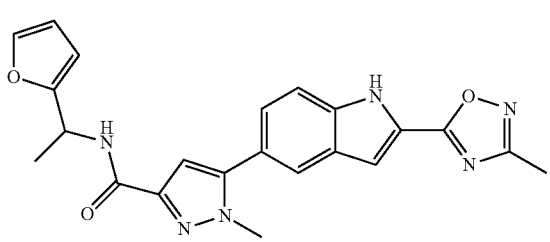 |
| 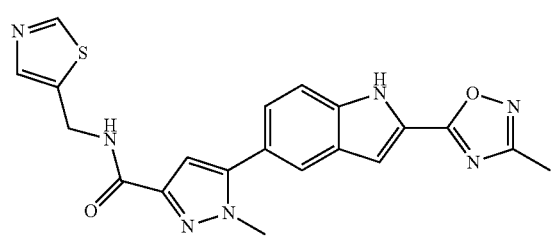 | 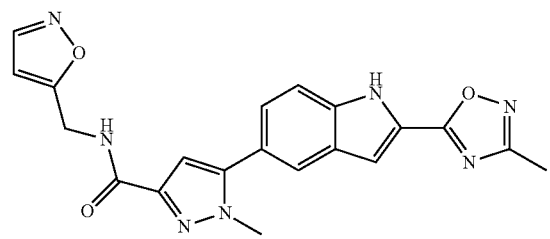 |
| 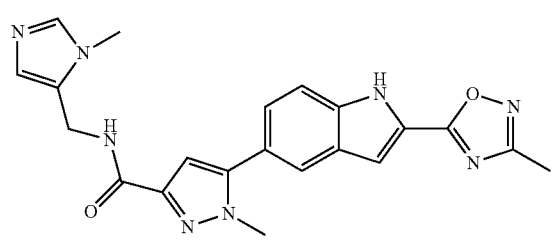 | 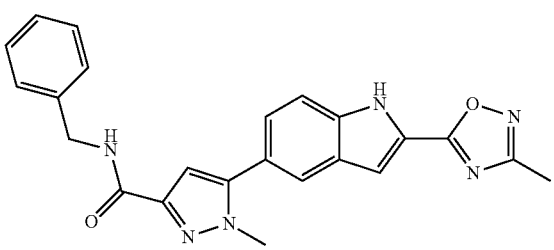 |

163
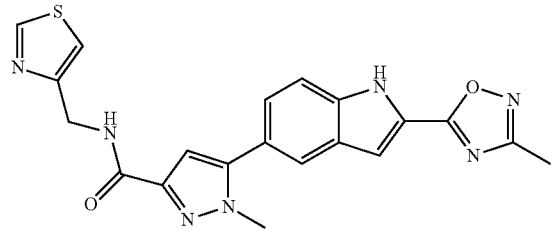
164
-continued
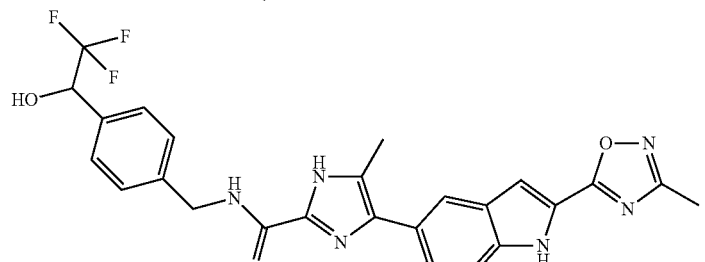
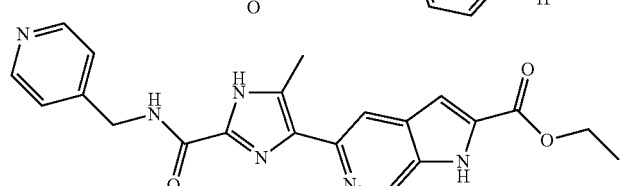
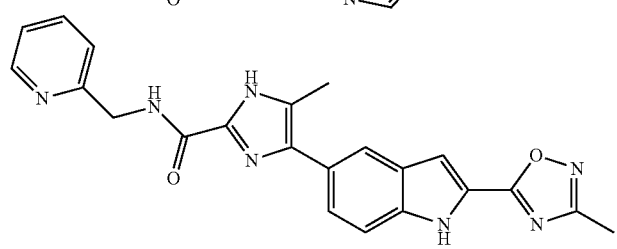
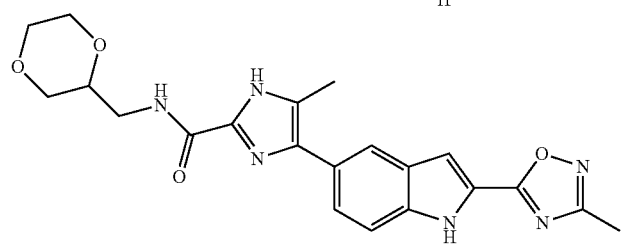
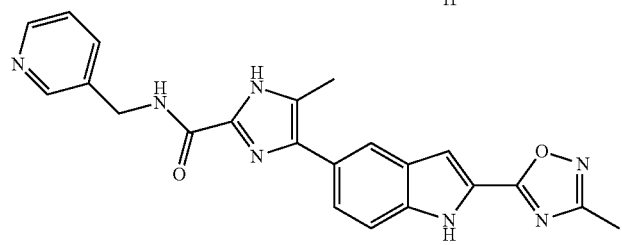
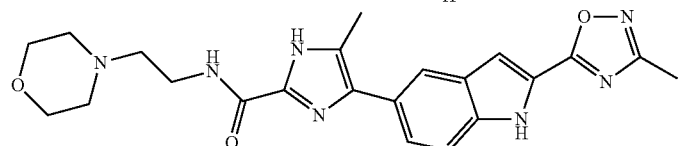
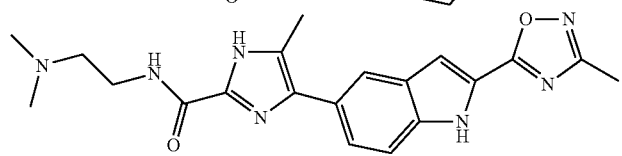

-continued
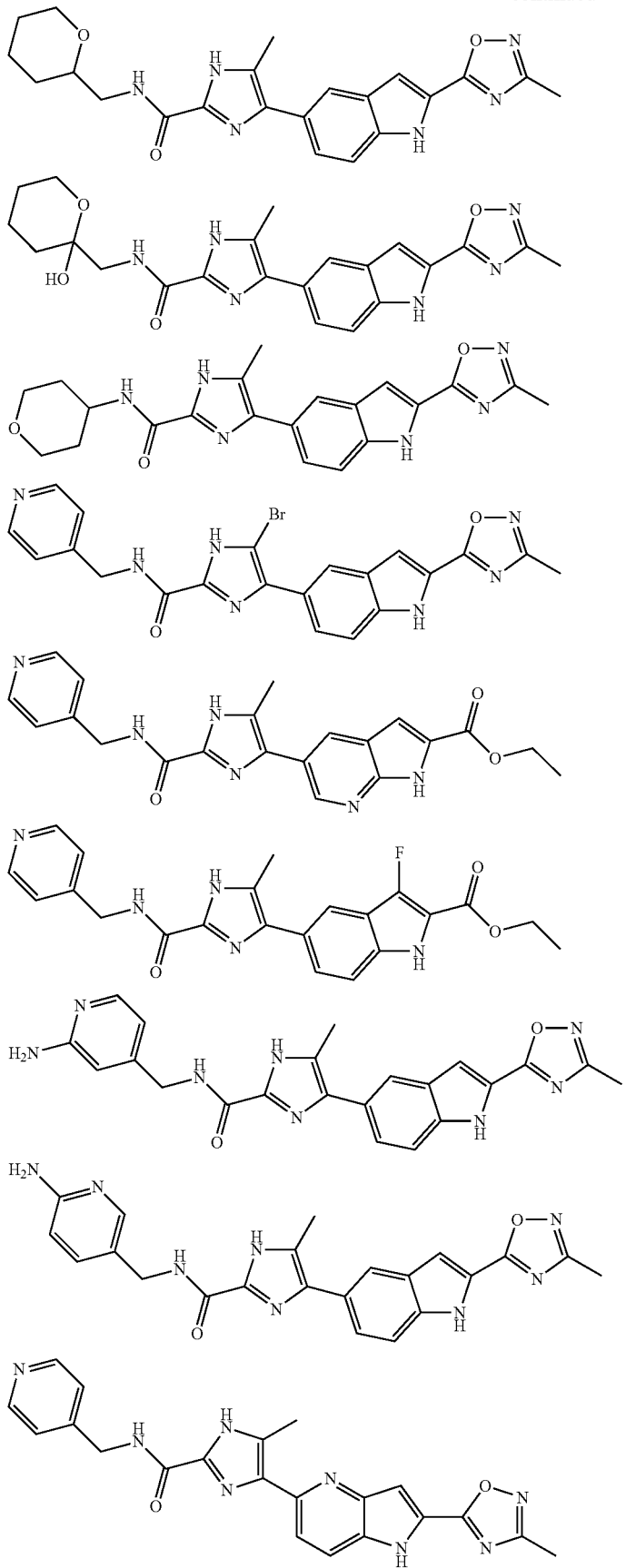

-continued
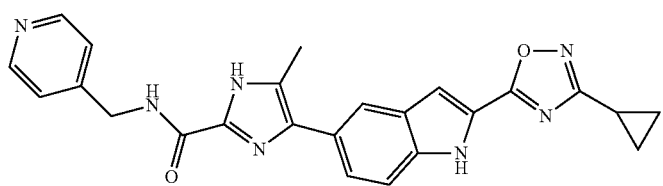
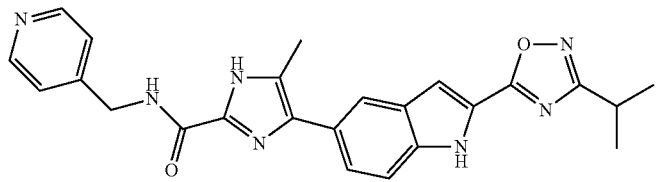
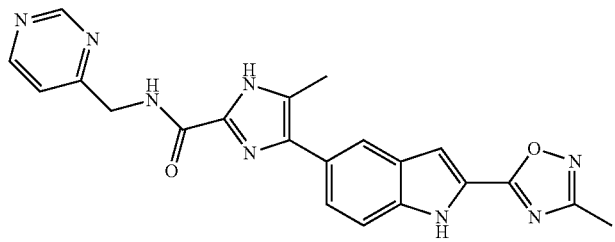
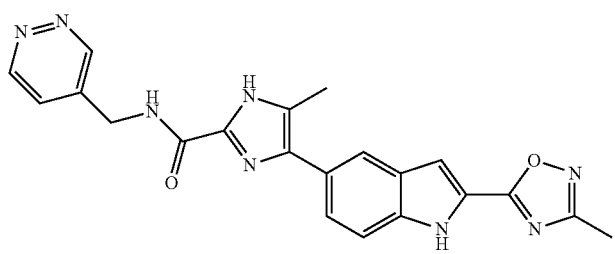
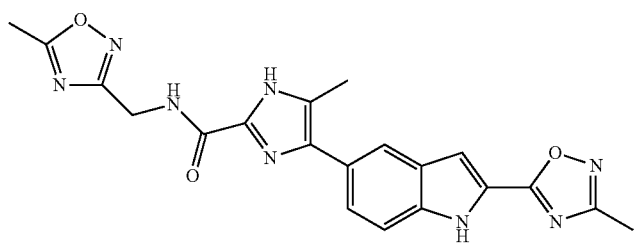
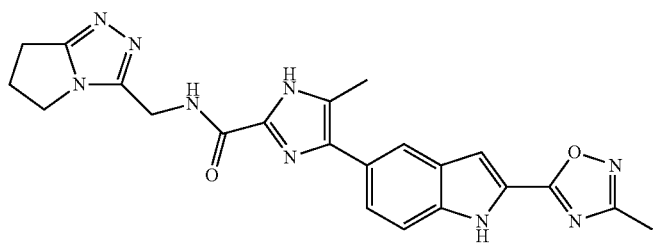
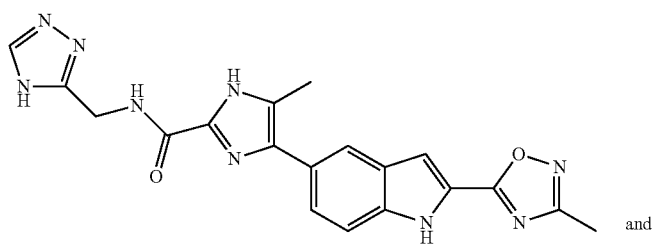
and -continued

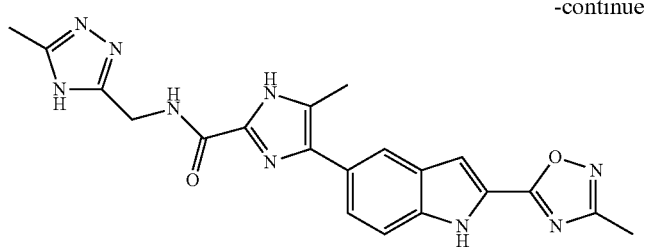

or a pharmaceutically acceptable salt thereof.

10. A pharmaceutical composition comprising a therapeutically effective amount of a compound according to claim 1 and one or more pharmaceutically acceptable carriers and/or adjuvants.

11. A method of treating a disease chosen from rheumatoid arthritis, osteoarthritis, osteoporosis, peridontitis, atherosclerosis, congestive heart failure and multiple sclerosis comprising administering a therapeutically effective amount of a compound according to claim 1 to a patient in need thereof.

* * * * *